US005648481A

United States Patent [19]
Parodos et al.

[11] Patent Number: 5,648,481
[45] Date of Patent: Jul. 15, 1997

[54] NUCLEIC ACID PROBES FOR THE DETECTION OF SHIGELLA

[75] Inventors: Kyriaki Parodos, Marlborough; Janice McCarty, Hyde Park, both of Mass.

[73] Assignee: Amoco Corporation, Chicago, Ill.

[21] Appl. No.: 375,241

[22] Filed: Jan. 19, 1995

Related U.S. Application Data

[63] Continuation of Ser. No. 150,764, Nov. 12, 1993, abandoned, which is a continuation of Ser. No. 738,800, Jul. 31, 1991, abandoned.

[51] Int. Cl.$^6$ .................................................. C07H 21/04
[52] U.S. Cl. .............................. 536/24.32; 536/24.33; 935/77; 935/78
[58] Field of Search ........................... 536/24.32, 24.33; 435/6, 91.2; 935/78, 77

[56] References Cited

U.S. PATENT DOCUMENTS

| | | | |
|---|---|---|---|
| 4,816,389 | 3/1989 | Sansonetti et al. | 435/6 |
| 4,992,364 | 2/1991 | Sansonetti et al. | 435/6 |
| 5,084,565 | 1/1992 | Parodos et al. | 536/24.32 |

FOREIGN PATENT DOCUMENTS

| | | |
|---|---|---|
| 0357306 | 3/1990 | European Pat. Off. . |
| 8706621 | 11/1987 | WIPO . |

OTHER PUBLICATIONS

Venkatesan, M. et al., "Development and Testing of Invasion–Associated DNA Probes for Detection of *Shigella* spp. and Enteroinvasive *Escherichia coli*" *J. Clin. Microbiol.*, 26(2): 261–266 (1988).
Venkatesan, M. et al., "Use of *Shigella flexneri ipa*C and *ipa*H Gene Sequences for the General Identification of *Shigella* spp. and Enteroinvasive *Escherichia coli*" *J. Clin. Microbiol.*, 27(12): 2687–2691 (1989).
Taylor, D.N. et al., "Clinical and Microbiologic Features of *Shigella* and Enteroinvasive *Escherichia coli* Infections Detected by DNA Hybridization" *J. Clin. Microbiol.*, 26(7): 1362–1366 (1988).
Frankel, G. et al., "Detection of *Shigella* in Feces Using DNA Amplification" *J. Infect. Dis.*, 161(6): 1252–1256 (Jun. 1990).
Boileau, C.R. et al., "DNA Hybridization Technique to Detect *Shigella* Species and Enteroinvasive *Escherichia coli*" *J. Clin. Microbiol.*, 20(5): 959–961 (1984).
Sethabutr, O. et al., "A Non–Radioactive DNA Probe to Identify *Shigella* and Enteroinvasive *Escherichia coli* in Stools of Children with Diarrhoea" *Lancet.*, ii, pp. 1095–1097, Nov. 16, 1985.
Sethabutr, O. et al., "DNA Hybridization in the Identification of Enteroinvasive *Escherichia coli* and *Shigella* in . . . " (1985), In: *Infection Diarrhoea in the Young*, S. Tzipoti et al., eds., (Elsevier Science Publishers, B.V.), pp. 350–356.
Gomes, T.A.T. et al., "DNA Probes for Identification of Enteroinvasive *Escherichia coli*", *J. Clin. Microbiol.*, 25(10): 2025–2027 (1987).

Small, P.L.C. and S. Falkow, "Development of a DNA Probe for the Virulence Plasmid of *Shigella* spp. and Enteroinvasive *Escherichia coli*." (1986) In: *Microbiology–1986*, Leive,L., ed. (Am. Soc. for Microbiol. Washington, D.C.) pp. 121–124.
Marich, J.E. et al., "The Detection of *Shigella* and Enteroinvasive *E. coli* (EIEC) Using Oligonucleotide DNA Probes" *Abstr. Ann. Mtg. Am. Soc. Microbiol.*, 89: 112, abstract No. D–179 (1989).
Braun, G. and S.T. Cole, "The Nucleotide Sequence Coding for Major Outer Membrane Protein OmpA of *Shigella dysenteriae*", *Nucl. Acids Res.*, 10(7): 2367–2378 (1982).
Buysse, J.M. et al., "Molecular Cloning of Invasion Plasmid Antigen (ipa) Genes from *Shigella flexneri*: Analysis of ipa Gene Products and Genetic Mapping", *J. Bacteriol.*, 169(6): 2561–2569.
Morrissey, D.V. et al., "Nucleic Acid Hybridization Assays Employing dA–Tailed Capture Probes; I. Multiple Capture Methods," *Analytical Biochemistry* 181: 345–359 (1989).
Hunsaker, W.R. et al., "Nucleic Acid Hybridization Assays Employing dA–Tailed Capture Probes; II. Advanced Multiple Capture Methods," *Analytical Biochemistry* 181: 360–370 (1989).
Lizardi, P.M. et al., "Exponential Amplification of Recombinant–RNA Hybridization Probes, " *Bio/Technology* 6: 1197–1202 (Oct. 1988).
Lomeli, H. et al., "Quantitative Assays Based on the Use of Replicatable Hybridization Probes," *Clin. Chem.* 35(9): 18261–1831 (1989).
Pritchard, C.G. and J.E. Stefano, "Amplified Detection of Viral Nucleic Acid at Subattomole Levels Using Q Beta Replicase," *Ann. Biol. Clin.* 48: 492–497 (1990).
Dale, D.C. and L.J. Mata, "Studies of Diarrheal Disease in Central America; XI. Intestinal Bacterial Flora in Malnourished Children with Shigellosis," *Am. J. of Tropical Medicine and Hygiene* 17(3): 397–403 (1968).
Thomson, S. "The Numbers of Pathogenic Bacilli in Faeces in Intestinal Diseases," *Journal of Hygiene* 53: 217–224 (1955).

(List continued on next page.)

*Primary Examiner*—Lisa B. Arthur
*Attorney, Agent, or Firm*—Norval B. Galloway

[57] ABSTRACT

The invention relates to methods of detection of bacteria of the genus Shigella and/or Enteroinvasive *E. coli* (EIEC) by use of a set of nucleic acid probes. The invention further relates to a set of Shigella specific chromosomal sequences and fragments and to probes derived from the Shigella specific fragments. Additionally, probes were derived from a sequence from the Shigella ompA gene. In particular, a series of probes, each approximately 40 nucleotides in length, were designed having specificity for Shigella or for Shigella and Enteroinvasive *E. coli*, and having utility in non-isotopic test formats which require amplification to achieve high sensitivity. Specific hybridization probe sets which are capable of detecting substantially all clinically significant serotypes of Shigella, as well as enteroinvasive strains of *E. coli*, are disclosed.

50 Claims, 15 Drawing Sheets

OTHER PUBLICATIONS

Matsutani, Sachiko et al. (1987) Journal of Molecular Biology, vol. 196, pp. 445–455.

Welcher, A.A. et al. (1986) Nucleic Acids Research, vol. 14, No. 24, pp. 10027–10044.

Cleuziat, P. et al. (1990) FEMS Microbiology Letters. Vol. 72, pp.315–322.

Wood, P.K. Journal of Clinical Microbiology, vol. 24, pp. 498–500, (1986).

FIGURE 2

```
                5'
NT6             aaTCCAACCGGCAGTAATAAACTGAATCCCTCGCATGGCTTGCAGCGCCTCTACTA
Probe 1500                                          TTGCAGCGCCTCTACTA NT6 cont'd      CCGGATACAGCCTCCATTCGGTAACNgCCTCCTTCAGGGCGGATTCCAGCCCGTTC
1500 cont'd     CCGGATACAGCCTCCATT
Probe 1501                                CCTCCTTCAGGGCGGATTCCAGCCCGTTC Sau3A
                              --
                              --
                                                                  3'
NT6 cont'd      ACATTGTGCCTGCCGATCTTCTATTGTACGACGGTGTTCGTCAAAAGCTAATTG
1501 cont'd     ACATTGT
Probe 1911             CCGATCTTCTATTGTACGACGGTGTTCGTCAAAAGCTAAT
```

FIGURE 3A

```
NT11-2               5'  CATCAGAAATCTAAGCAGAAGTCTTTCCGTGTTTCTCAGAAATGGGGGCAACGTGC
Probe 1683                                AGTCTTTCCGTGTTTCTCAGAAATGGGGGCAACGTGC NT11-2 cont'd            AAAACTTGCCCTTGCTGGTGAACAACGTCTTTACAAAGATGGTTCCTGGATGGATTG
1683 cont'd              AAAA
Probe 1682                                    CTGGTGAACAACGTCTTTACAAAGATGGTTCCTGGATGGATT NT11-2 cont'd            ACCCTGAGACTTTTAAACTCAATGAACACGCTGAGACTGTGAGATTGATATATTCAAA NT11-2 cont'd            CTGCTGCTAGATGGTGAAAGTCTGCATAACATTGCACGTCACCTTCAAAGCAACGG NT11-2 cont'd            TATAAAGTCGTTTAGTCGCCGTAAAGATGCTAATGGGTtCTCTGTTCACTCTGTAC NT11-2 cont'd            GCACATTCTAAGGTCAGAGCAACAATAGGCACGTTACCAGCATCACAACGTAATGA NT11-2 cont'd            CCGCCCCGCTATACCGAACTACTACGAAGGTGTTGTAGATATACCAACGTTCAATA NT11-2 cont'd            AAGCTCAAGAGATTCTCGACAAGAATCGTAAAGGCCGTACACCTGCAAGTGACAAC
```

FIGURE 3B

```
NT11-2 cont'd        CCACTAACGATTAACATCTTCAAAGgtCTGTGTTTAGGTGTCAGTGTGGGGCTAGTGT NT11-2 cont'd        CCATCCTACCGGAACAAAGAATAAGTATGCTGGGGTCTACAGGTGCAATAACCACT
Probe 1709                                      GCTGGGGTCTACAGGTGCAATAACCACT NT11-2 cont'd        TAGACGGTCGCTGTGATGTTCCACCGTTGAAGCGTAAACCGTTTGACCGATGGATG
1709 cont'd          TAGACGGT
Probe 1708                           CCACCGTTGAAGCGTAAACCGTTTGACCGATGGAT NT11-2 cont'd        ATTGATAATTTTCTGGGGATGATTGACGTGTGGGAATGATGGAGAATCAGAGAGAA NT11-2 cont'd        AGATTGCAGCCGTTACAGCATGAGGTTGAAATTGTCACAGCCAGAATCAAGAAACG NT11-2 cont'd        TACCGCCCTACTTCTTGAGATGGATGATATTGATGAACTAAAAATTCAGCTTAAG
                                                                             3'
NT11-2 cont'd        GAACTGAACCAGAAG
```

FIGURE 4A

```
5'
NT15    GATCTTTCTTCGAAGAAGAGAGGCGCCACCAATACCCGCCCACGAGAGAGCCCAG

NT15    ACCTGCGCCGATAGCCAGATTTGCCTGCGTTCGCCGGTGTAAGGGTTAGTT

NT15    GTGCAGCCAGATACCCGCCAGAGGCGCCACTCACTACGGAGGCAATAAGATAAACAC

NT15    GTTTGTTCATTGTTAATCCTTCCTAACCTTTTTATTCTTGCCACGGGTTCCGTG
E.c. 2                                                    TGTGG
S.f.                                                      AAAGC

NT15    GCGGGAGATTATGCCGCGTGAACATGAAGATGAGGTGTACTGGCAATAGCGGACA
E.c. 1                           AGTTGGACTATAGGTGTACTgGCAATA-CgGACA
E.c. 2  CATCAACAATGGTGCGACCGAGACGAGATGAGGTGTACTGGCAATAGCGGACA
S.f.    ACAGATTTTATAGCTAACTCGATGCTGGTGTGAGGTGTACTGGCAATAGCGGACA
                                    ***
                            Left end of repeat.

NT15    CTACCATTTGTTCTTTTTTTAAGCAGCCATCTGATGATATTTTCCCTGAAGGCT
E.c. 1  C-AcCAtTTGTTctttttTTTAAGCAG-CATCTGATGATAtttTTCCCTGAAGGCT
E.c. 2  CAAC---------------------------------------------------
S.f.    CTAC---------------------------------------------------
```

FIGURE 4B

```
NT15      GCCGGGGAGATATTCCCCAGACGAGAGTGACGACGCTGACGACGATTCTAGAAAATCTC
E.c. 1    GCCgggGAGATATTCCCCAGACGAGAGTGACGACGCTGACGACGATTCTAGAAAATCTC
E.c. 2    ------------------------------------------ATTGTAGAAAATCTC
S.f.      ------------------------------------------ATTGTAGAAAATCTC NT15      AATGTATTCCCGTATTACTGAGATGGCTTCATCCCGGTTATTAAAACGATAGTGGC
E.c. 1    AATGTAttCCCGTATTACTGAGATGGCTTCATCCCGGTTATTAAAACGATAGTGGC
E.c. 2    AATGTATtCCCGTATTACTGAGATGGCTTCATCCCGGTTATTAAAACGATAGTGGC
S.f.      AATGTATtCCCGtATTACTGAGATGGCTTCATCCCGGTTATTAAAACGATAGTGGC NT15      TCAGGCTCTCATTTTTCAGCGTTCCCCACAAGCTTTCCATCGGAGCGTTGTCGTAA
E.c. 1    TCAGGCTCTChATTTTTTCAGCGTTCCCCANAAGCTTTCCATCGGAGCGTTGTCGTAA
E.c. 2    TCAGGCTCTChATTTTTTCAGCGTTCCCCANAAGCTTTCCATCGGAGCGTTGTCGTAA
S.f.      TCAGGCTCTChATTTTTTCAGCGTTCCCCANAAGCTTTCCATCGGAGCGTTGTCGTAA NT15      CAGTTACCTTTACGCGACATTGATGTTTTCAGACCAGACTGCTCCTGTATGACCCGG
E.c. 1    CAGTTACCTTTACGCGACATTGATGTTTTCAGACCAGACTGCTCCTGTATGACCCGG
E.c. 2    CAGTTACCTTTACGCGACATTGATGTTTTCAGACCAAACTGCTCCTGTATGACCCGG
S.f.      CAGTTACCTTTACGCGACATTRATGTTTTCAGACCAGACTRCTCCTGTATGACCCGG
Probe 1864                                    3' AGTCTGGTCTGACGAGG 5'
```

FIGURE 4C

```
NT15    TAATCGTATGCGCAGTACTGTGAACCTCGATC
NT14                                   GATCAGAGAGTGGTGGATTAGCCCGGCAG-
E.c. 1  TAATCGTATGCGCAGTACTGTGAACCTCGATCAGAGAGTGGTGGATTAGCCCGGCAGG
E.c. 2  TAATCGTATGCGCAGTACTGTGAACCTCGATCAGAGAGTGGTGGATTAGCCCGGCAGG
S.f.    TAATCGTATGCGCAGTACTGTGAACCTCGATCAGAGAGTGGTGGATTAGCCCGGCAGG

NT14    TGGGCGCTGGCTCCTGAGCGCCATAAACAGGGCTTTACCTGTCAGCTCTTTTGTCA
E.c. 1  NGGGCGCTGGCTCCTGAGCGCCATAAACAGGGCTTTACCTGTCAGCTCTTTTGTCA
E.c. 2  NGGGCGCTGGCTCCTGAGCGCCATAAACAGGGCTTTACCTGTCAGCTCTTTTGTCA
S.f.    NGGGCGCTGGCTCCTGAGCGCCAAATCCTGTCAGCTCTWTTGTCA

NT14    TGCGCTCTCCCATGGCGTA--CGAC-AATTTCGCACGTATAAACATCTTTGATGCC
E.c. 1  TGCGCTCTCCCATG-CGTAGCCGAC-AATTTCGCACGTATAA-CATCTTTGATGCC
E.c. 2  TGCGCTCTCCCATG-CGTAGCCGAC-AATTTCGCACGTATAA-CATCTTTGATGCC
S.f.    TGCGCTCTCCCATG-CGTAGCCGACtAATTTCGCACGTATAA-CATCTTTGATGCC

NT14    AGCGAGGTACAACCATCCCTCCTGTGTGGCAACATACGTCAGTCCGCCACCCAGA
E.c. 1  AGCGAGGTACA-CCATCCCTCCTGTGTGGCAnCATACGTCAGTCCGCCACCCAGA
E.c. 2  AGCGAGGTACA-CCATCCCTCCTGTGTGGCAnCATACGTCAGTCCGCCACCCAGA
S.f.    AGCGAGGTACA-CCATCCCTCCTGTGTGGCAnCATACGTCAGTCCGCCACCCAGA
```

FIGURE 4D

```
NT14      CCTGATTTGGTGCTGTGTAGGAGCGAACGTCTGGTTCAGCAGATTTGGCGCAACTGGC
E.c. 1    CCTGaTTTGGTGCTGTGTAGGAGCGAACGTCTGGTTCAGCAGATTTGGGCGCAACTGGC
E.c. 2    CCTGaTTTGGTGCTGTGTAGGAGtGAACGTCTGGTTCAGCAGATTTGGCGCAACTGGC
S.f.      CCTGaTTTGGTGCTGTGTAGGAGtGAACGTCTGGTTCAGCAGATTTGGGCGCAACTGGC
          CCTGaTTTGGTGCTGTGTAGGAGCGAACGTCTGGTTCAGCAGATTTGGGCGCAACTGGC

NT14      AGATTGTGGTTCGAGTTCGTAGTCGCCTCTGAACTTGCGTT-CTGCTTACAGCGTAG
E.c. 1    AGATTGTGGTTCGGGTTCGTAGTCGCTCGCTCTGAaCTTGCGTTTCTGCTTACAGCGTAS
E.c. 2    AGATTGTGGTTCGGGTTCGTAGTCGCTCGCTCTGAaCTTGCGTTTCTGCTTACAGCGTAG
S.f.      AGATTGTGGTTCGAGTTCGTAGTCGCTCGCTCTGAaCTTGCGTTTCTGCTTACAGTGTAG

NT14      -CTTAGCTCCTTACGAAGACGTGCCAGTCGGTCACGACCAACGATGATGCCATTCT
E.c. 1    -CTTAGCTCCTTACGAAGACGTGCCAGTCGGTCACG-CCAACGATGATGCCATTCT
E.c. 2    -CTTAGCTCCTTACGAAGACGTGCCAGTCGGTCACG-CCAACGATGATGCCATTCT
S.f.      CCTTAGCTCCTTACGAAGACGTGCCAGTCGGTCACG-CCAACGATGATGCCATTCT
Probe 437                                           5' CGATGATGCCATTCT NT14      CTGCCAGCTCCGTCTCTGG-AGCCGCCGGGTT-CCATATGTTTCGGAGTGCGGATAT
E.c. 1    CTGCCAGCTCCGTCTCTGG-AGCCGCCGGGTT-CCATATGTTDCGCRAGTGCGGATAT
E.c. 2    CTGCCAGCTCCGTCTCTGG-AGCCGCCGGGTT-CCATATGTTDNGCRAGtGCGGATAT
S.f.      CTGCCAGCTCCGTCTCTGG-AGCCGCCGGGTT-CCATATGTTNCGCRAGTGCGGATAT
437 cont'd CTGCCAGCTCCGTCTCGGGAGCCGCCGGGTTTCC 3'
```

FIGURE 4E

```
NT14    GTGCCACCTTAATCTCCAGTTTTTAGCCGCTCATCACTTTGTTTTCTGTCTGAGGGT
E.c. 1  GTGCCACCTTAATCTCCAGTTTTTAGCCGCTCATCATCACTTTGTTTDTCTGTCTGAGGGT
E.c. 2  GTGCCACCTTAATCTCCAGTTTDAGCCGCTCATCACTTTGTTDTCTGTCTGAGGGt
S.f.    GTGCCACCTTAATCTCCAGTTTDAGCCGCTCATCACTTTGTTDTCTGTCTGAGGGT

NT14    TCATGCTGTACCCAGTTGTAATAACCGTCCTGGATACACCAAATAC-TGACACAT
E.c. 1  tCATGCTGTACCCAGTTGTAATAACCGTCCTGGATACACCAAATACCTGACACAT
E.c. 2  TCATGCTGTACCCAGTTGTAATAACCGTCCTGGATACACCAAATACCTGACACAT
S.f.    TCATGCTGTACCCAGTTGTAATAACCGTCCTGGATACACCAAATACCTGACACAT

NT14    CGCTTCAATGGGAAATTGTTGTCGCCATTGTTCGATTAACGCGTATTTTCAGCGA
E.c. 1  CGCTTSAATDDDAAATTGTTGTCGCCATTGTTCGATTAACGCG------CAGCGA
E.c. 2  CGCTTNAATGGAAATTGTTGTCGCCATTGTTCGATTAACGCGnATTTTCAGCGA
S.f.    CGCTTSAATGGGAAATTGTTrTCGCCATTGTTCGATTAACGCG---------A

NT14    CTCCTGTGCAAAATACGCTGTTGCTTTTTTAATATATCTCGCTCAAGGCGAGCTT
E.c. 1  CTCCTGTGCAAAATACGCTGTTGCTtTTTGCTtTTTtAATATATCTCGCTCaAGGCGAGCTT
E.c. 2  CTCCTGTGCAAAATACGCTGTTGCTTTTTTNATATATCTCGCTCAAGGCGAGCTT
S.f.    CTCCTGTGCAAAATACGCTGTTGTTGCTTTTTTTTTTNNATATATCTCGCTCaAGGCGAGCTT

NT14    CATTTAACGCCTTACGCAGTCGCAGAATTCAGATTCCAGTTCAGCCACCGTGCGG
E.c. 1  CATTTAACGCTTtACGCAGTTGCAGAATTCAGATTCCAGTTCAGCCACCGTGCGG
E.c. 2  CATTAACGCCTTACGCAGTTGCAGAATTCAGATTCCAGTTCAGCCACCGTGCGG
S.f.    CATTTAACGCCTTACGCAGTTGCAGAATTCAGATTCCAGTTCAGCCACCGTGCGG
```

FIGURE 4F

```
NT14        GAACCAGGAGTACCGAGCCCTTTTCTGGCGGCGGGTAACCCATTGTCCTAAAGTGCC
E.c.   1    GAaCCAGGAGTACCGAGCCCTTTTCTGGCGGCGGGTAaCCCATTGTCCTAAAGTGCC
E.c.   2    GAaCCAGGAGTACCGAGCCCTTTTCTGGCGGCGGGTAaCCCATTGTCCTAAAGTGCC
S.f.        GAaCCAGGAGTACCGAGCCCTTTTCTGGCGGCGGGTAaCCCATTGTCCTAAAGTGCC

NT14        TTCAGGAAGAGATAATCGGGAAGCGCCCTTCACTGATC
E.c.   1    TTCAGGAAGAGaTAATCGGGAAGCGCCCTTCGCTGATCGAAAGTTGATTTTCAAGAA
E.c.   2    TTCAGGAAGAGAGnTAATCGGGAAGCGCCCTTCGCTGATCGAAAGTTGATTTTCAAGAA
S.f.        TTCAGGAAGAGaTAATCGGGAAGCGCCCTTCACTGATCGAAAGTTGATTTTCAGGAA

E.c.   1    CCGTTCTGACAGCTTCGGCTTTGAACTCTGt
E.c.   2    CCGTTCTGACAGCTTCGGCTTTGAACTCTTTAGAGTAACGTTGGTTTTTCTGCTC
S.f.        CCGTTCTGaCAGCTTCGGCTTTGAACTCTTKAGAGTAACGTTGGGTTTTTCTGCTC

E.c.   2    ATTATTAGCTCCTTCTGATGCCATTCTATTTCAGGAAGGAGTGTCCGTTAAACTCA
S.f.        ATTATTAGCTCCTTCTGATGCCATTCTATTTCAGGAAGGAGTGTCCGTTAAACTCA

E.c.   2    GGCTACCTCAAGATAAAGTTATTAATTTCGAAGATCACATCTTCAATAGGTTTGCG
S.f.        GGCTACCTCAGTGTGATCGGCGATAAGCCCAGaACTCCGCTCCCAGACCCCCTGC
                                                      ***
                                   Right end of repeat.

E.c.   2    GTCCATTATTATC
S.f.        CAAAAGCAAAACCG
                          3'
```

FIGURE 5A

```
NT18-1a        5'
               ATCTCCTTATGTTATGGAGATTATTAAAAAGAATAACATTAGCGCTCTCGAACT
NT18-1a cont'd GCATCGTGCAATTGTTGAGTTGAGTAAAAATATGAAGTCGATTGATGATAATGC
NT18-1a cont'd CAGTAAGAAAAACGACAAGTCATCATTGTATGTATCATGGACTCTGAGTTTTAC
NT18-1a cont'd TGCTCCAACAAGTAAAAGAAGCTCACGATGTGTTGTCTGGGTATATTAATTATGT
NT18-1a cont'd TTCTTCCCTTGTTGTAAGGGATTTGATGGAAGATATAAGAAATAAACTAGAAGT
NT18-1a cont'd TAAAACTAATGTTGAAAAAGAAATTCTTGCACTGGATGAGATAAAAATTAGAAA
NT18-1a cont'd CCAGCTGAATGCAGATATTCGACNCCTCAATTATTCACTGGAGGTTGCTAATGC
NT18-1a cont'd GGCTGGAATAAAAAACCTGTATACAGCAATGGTCAGATTATGAAGGATGACCC
```

FIGURE 5B

NT18-1a cont'd  
Probe 1712
AGATTTTCCTGTGGCTCTCTCGGTTCTCTGATGGTATAGCAACTAAATTGAACATCAA
CCTGTGGCTCTCTCGGTTCTCTGATGGTATAGCAACTAAAT NT18-1a cont'd  
Probe 1713
AAAATCAATCAAGGATGTTTTCGGAATTGAGTGGGGAGTTGCCGAAATCGTCAATA
CAAGGATGTTTTCGGAATTGAGTGGGGAGTTGCGAAAT NT18-1a cont'd
TGTTGTGAATCAATTGGTTGTGGCGAAAGNGGGGANGNNGANNNNANGCMANN NT18-1a cont'd
NCAGNANCAANNGTGCCCAACGNNACCGGNCAgaAA
                                    3'

FIGURE 6A

NT19-2
5'
CCACCACATTGATTGTCTGCCTGAAATAACACGAAAGGCACTGCGTGAACGCTA

NT19-2 cont'd
TGTGGAACAGCTGGTGGCTACAGAGAACAATGTTTCTGAAGTGAAAGCTGTTAC

NT19-2 cont'd
Probe 1684
CAGAAAAACACGGCCAATCCTGACGCTGTCCAGGCAATCGAAGCATATCGCGGTTC
                              CAGGCAATCGAAGCATATCGCGGTTC NT19-2 cont'd
1684 cont'd
Probe 1685
TCCACAACTGATGGAAGAACGCCTGAATGCGCTGACCGAAAACCAGCGCTGGGT
TCCACAACT
                              TGAATGCGCTGACCGAAAACCAGCGCTGGGT NT19-2 cont'd
ATCTGAAGCAAGAGCTGCGCTGGTGGTGGAAGTGCTGAAGCTGGAAAGCGCCCGG 1685 cont'd
ATCT

FIGURE 6B

NT19-2 cont'd  TAACCCCGGGGCGACTGAAAGCCATTAACTTTCTTGTTGAAAAAGCCCCTAAAGG

NT19-2 cont'd  TGAGCTGCCGGAGCGCCTGCAACAGGCCGCAGTTAACGCCAATGCAAAACGTGG

NT19-2 cont'd  CGCTAATCGT
               3'

FIGURE 7

```
S.d. ompA      5' CTGACGACCTGGAGCGTGTACACTCGTCTGGGTGGGTATGGTTTGGCGTGCAGA
E.c. ompA         CTGACGACCTGGACATCTACACTCGTCTGGGTGGCATGGGTATGGCGTGCAGA S.d. ompA cont'd   CACCAAAGCTCACAACAATGTGACAGGTGAATCTGAGAAAAACCACGATACC
E.c. ompA cont'd   CACTAAATCC-----AACGTTTATGGT-------AAAA 5,648,481

1

NUCLEIC ACID PROBES FOR THE DETECTION OF SHIGELLA

This application is a continuation of application Ser. No. 08/150,764, filed Nov. 12, 1993, now abandoned, which is a File Wrapper Continuation of Ser. No. 07/738,800, filed Jul. 31, 1991, now abandoned.

BACKGROUND OF THE INVENTION

The genus Shigella includes four species (major serogroups): *S. dysenteriae* (Grp. A), *S. flexneri* (Grp. B), *S. boydii* (Grp. C) and *S. sonnei* (Grp. D) as classified in Bergey's Manual for Systematic Bacteriology (N. R. Krieg, ed., pp. 423-427 (1984)). These serogroups are further subdivided into serotypes (Table 1). The genera Shigella and Escherichia are phylogenetically closely related. Brenner and others have suggested that the two are more correctly considered sibling species based on DNA/DNA reassociation studies (D. J. Brenner, et al., *International J. Systematic Bacteriology*, 23:1-7 (1973)). These studies showed that Shigella species are on average 80-89% related to *E. coli* at the DNA level. Also, the degree of relatedness between Shigella species is on average 80-89%. *Shigella boydii* serotype 13 is atypical in that it is only 65% related to other Shigella serotypes and Escherichia.

The genus Shigella is pathogenic in humans; it causes dysentery at levels of infection of 10 to 100 organisms. By contrast, the majority of *E. coli* (9000 O:H serotypes) are not associated with diarrheal disease. Pathogenic *E. coli* serotypes are collectively referred to as Enterovirulent *E. coli* (EVEC) (J. R. Lupski, et al., *J. Infectious Diseases*, 157:1120-1123 (1988); M. M. Levine, *J. Infectious Diseases*, 155:377-389 (1987); M. A. Karmali, *Clinical Microbiology Reviews*, 2:15-38 (1989)). This group includes at least 5 subclasses of *E. coli*, each having a characteristic pathogenesis pathway resulting in diarrheal disease. The subclasses include Enterotoxigenic *E. coli* (ETEC), Verotoxin-Producing *E. coli* (VTEC), Enteropathogenic *E. coli* (EPEC), Enteroadherent *E. coli* (EAEC) and Enteroinvasive *E. coli* (EIEC). The VTEC include Enterohemorrhagic *E. coli* (EHEC) since these produce verotoxins.

The pathogenesis of Enteroinvasive *E. coli* is very similar to that of Shigella. In both, dysentery results from invasion of the colonic epithelial cells followed by intracellular multiplication which leads to bloody, mucous discharge with scanty diarrhea.

Thus, detection of Shigella and EIEC is important in various medical contexts. For example, the presence of either Shigella or EIEC in stool samples is indicative of gastroenteritis, and the ability to screen for their presence is useful in treating and controlling that disease. Detection of Shigella or EIEC in any possible transmission vehicle such as food is also important to avoid spread of gastroenteritis.

Currently, presence of Shigella in stool samples is detected by cultivating an appropriately prepared sample on microbiological media under conditions favorable for growth of those bacteria. The resulting colonies are then examined for microbiological and biochemical characteristics, a process that typically takes at least three days and does not permit processing large numbers of samples. However, hospitals do not test for the presence of EIEC in stool because of the difficulty of serotyping which is necessary to identify the EIEC among the numerous, non-pathogenic *E. coli* normally present in stool.

SUMMARY OF THE INVENTION

The present invention relates to methods of detection of bacteria of the genus Shigella and/or Enteroinvasive *E. coli* (EIEC) by use of a set of nucleic acid probes. The invention further relates to a set of Shigella specific chromosomal sequences and fragments, which were isolated by subtractive hybridization against non-Shigella DNA, and to probes derived from the Shigella specific fragments. Additionally, probes were derived from a sequence from the Shigella ompA gene. In particular, a series of probes, each approximately 40 nucleotides in length, were designed having specificity for Shigella or for Shigella and Enteroinvasive *E. coli*, and having utility in non-isotopic test formats which require amplification to achieve high sensitivity. In addition, specific hybridization probe sets were developed which are capable of detecting substantially all clinically significant serotypes of Shigella, including *S. sonnei*, *S. flexneri*, *S. boydii*, and *S. dysenteriae*, as well as enteroinvasive strains of *E. coli*.

Probes or probe sets of the present invention can be used in a number of hybridization formats for the detection of Shigella species and/or Enteroinvasive *E. coli*. For example, the presence of one or more Shigella species and/or one or more species of EIEC in a sample can be determined by lysing the cells in the sample, contacting the sample with a DNA probe set under conditions suitable for hybridization of the probes with Shigella and/or EIEC DNA, capturing the hybrids formed between the probes and the sample DNA, and detecting the hybrid complexes by a suitable method as an indication of the presence of Shigella or EIEC in the sample.

BRIEF DESCRIPTION OF THE FIGURES

FIG. 2 illustrates the nucleotide sequence (SEQ ID NO: 1) of Shigella specific fragment NT6 and some flanking sequence, and the locations and sequences of probes 1500 (SEQ ID NO: 14), 1501 (SEQ ID NO: 15), and 1911 (SEQ ID NO: 16) which are derived from these sequences.

FIGS. 3A-3B illustrates the nucleotide sequence of Shigella specific fragment NT11-2 (SEQ ID NO: 2), and the locations and sequences of probes 1682 (SEQ ID NO: 17), 1683 (SEQ ID NO: 18), 1708 (SEQ ID NO: 19), and 1709 (SEQ ID NO: 20) derived from the fragment.

FIGS. 4A-4F illustrates the nucleotide sequence of Shigella specific fragments NT14 (SEQ ID NO: 4) and NT15 (SEQ ID NO: 3), comprising a version of the Class III repeat isolated from *S. sonnei*, and the location and sequence of probes 1864 (SEQ ID NO: 22) and 437 (SEQ ID NO: 21), derived from these fragments. The sequences of three versions of the Class III repeat isolated from *E. coli* (E.c. 1; SEQ ID NO: 5; and E.c. 2; SEQ ID NO: 6 and SEQ ID NO: 7) and *S. flexneri* (S.f.; SEQ ID NO: 8 and SEQ ID NO: 9) are also shown.

FIGS. 5A-5B illustrates the sequence of Shigella specific fragment NT18-1a (SEQ ID NO: 10), and the location and sequence of probes 1712 (SEQ ID NO: 23) and 1713(SEQ ID NO: 24), derived from the fragment.

FIGS. 6A-6B illustrates the sequence of Shigella specific fragment NT19-2(SEQ ID NO: 11), and the location and sequence of probes 1684 (SEQ. ID NO: 25) and 1685 (SEQ ID NO: 26), derived from the fragment.

FIG. 7 illustrates a portion of the sequence of the *S. dysenteriae* (S.d.) ompA gene (SEQ ID NO: 12), and the location and sequence of probes 1706 (SEQ ID NO: 27) and 1707 (SEQ ID NO: 28), derived from the ompA gene sequence. The *E. coli* (E.c.) ompA gene sequence (SEQ ID NO: 13) corresponding to the same region is shown for comparison.

DETAILED DESCRIPTION OF THE INVENTION

Figure 1:
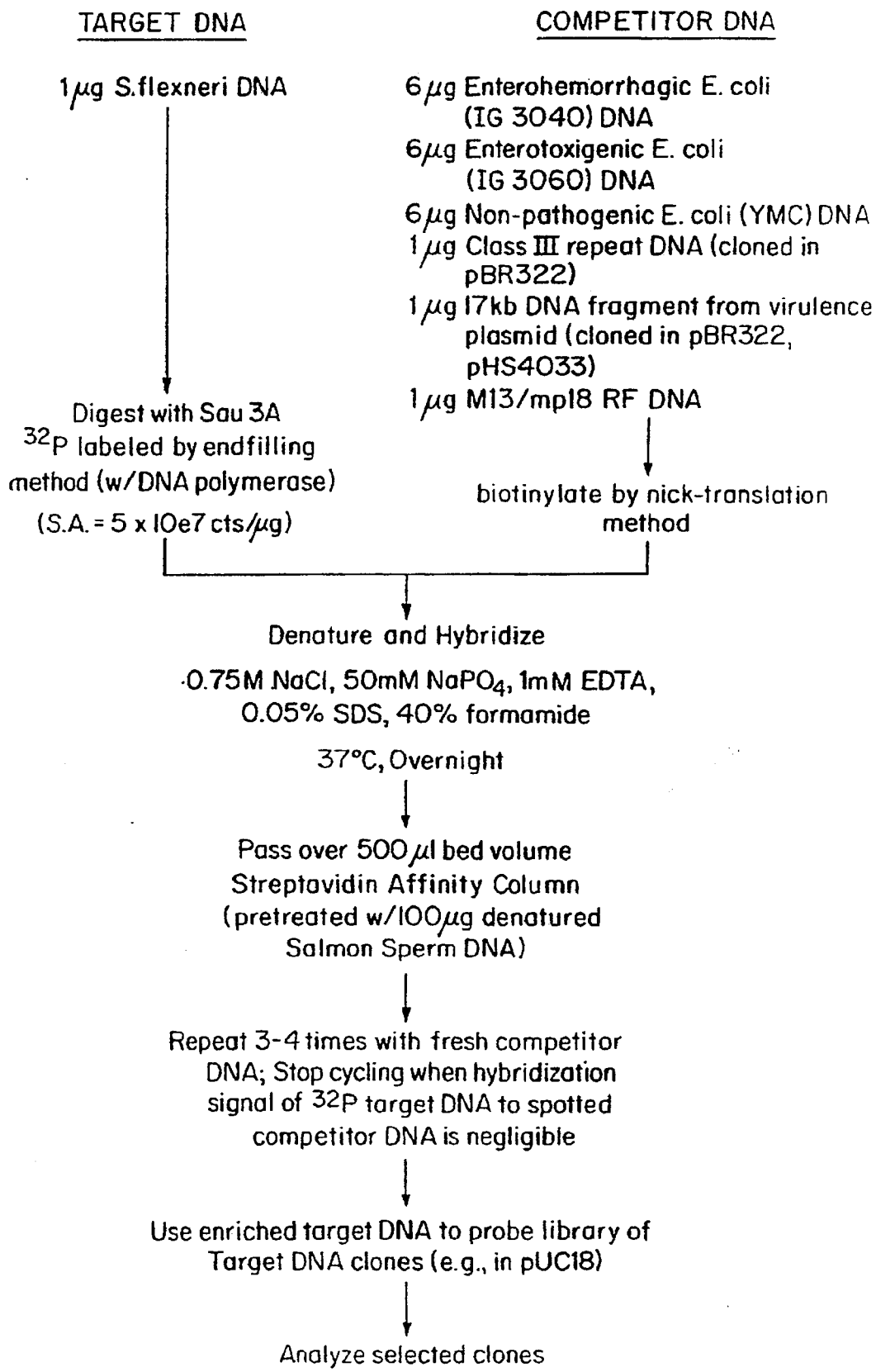
FIG. 1 is a flow chart illustrating a strategy for the isolation of Shigella specific DNA sequences from "target" DNA and of Shigella specific fragments from a library of target DNA clones.

Previous investigators interested in developing specific probes for Shigella have targeted the virulence plasmid. Both Shigella and EIEC harbor a single copy virulence plasmid approximately 140 MD (215 kilobasepairs) in size which is necessary for invasion (T. L. Hale, *Infection and Immunity*, 40:340–350 (1983)). For example, U.S. Pat. No. 4,816,389 (Sansonetti et al.) discloses a 27 kilobasepair (kb) region of the virulence plasmid proven necessary for invasion. These investigators have shown that the virulence plasmid, which exists as one copy per bacterium, is unstable; regions of the plasmid may be deleted. Shigella and EIEC strains, which have been stored or passaged in the laboratory, frequently are found to contain virulence plasmids of reduced size (C. Sasakawa, et al., *Infection and Immunity*, 51:470–475 (1986); A. T. Maurelli, et al., *Infection and Immunity*, 43:397–401)). The 27 kb region from which the probes of Sansonetti et al. have been derived has been shown to be one of the unstable segments (P. K. Wood, *J. Clinical Microbiology*, 24:498–500 (1986)). Strains of Shigella or EIEC which do not contain a portion of the 27 kb target region are not detected by the probe and are incorrectly identified as non-Shigella or non-EIEC.

Moreover, the 27 kb probe region contains insertion element 1 (IS1) which is ubiquitous among the Enterobacteriaceae (M. Venkatesan, et al., *J. Clinical Microbiology*, 26:261–266 (1988)). It also contains at least one copy of insertion element 600 (IS600; S. Matsutani, et al., *J. Molecular Biology*, 196:445–455 (1987)), which occurs frequently in both pathogenic and non-pathogenic representatives of *E. coli*, as well as in Shigella and EIEC (unpublished result). The presence of these broadly distributed insertion elements and the large size of the probes designed from the 27 kb region decrease the utility of these probes in non-isotopic test formats which require amplification in order to achieve high sensitivity.

In contrast, the present invention relates to probes and probe sets which are (1) developed from Shigella specific fragments derived from chromosomal sequences of Shigella and (2) moderate in size, each probe being approximately 40 bases in length. The increased stability of the chromosomal sequences detected by the probes compared to sequences of the virulence plasmid can result in increased reliability of detection. Furthermore, moderately sized probes have utility in non-isotopic test formats which require amplification to achieve high sensitivity. Both the Shigella specific fragments and the probes derived from them are also useful as hybridization probes in other formats. Some of the fragments derived from the Shigella chromosome are also present in an episomal location on the invasion plasmid or another plasmid.

In one embodiment, the invention features a nucleic acid probe set consisting essentially of nucleic acids with sequences that are:

a. derived from the chromosomal sequence of representative bacteria of the species *Shigella sonnei* (ATCC 29930, designated type strain) and *Shigella flexneri* type 2a (ATCC 29903, designated type strain) but are less than the entire chromosomal sequence of these bacteria;

b. capable of hybridizing to DNA of members of the four known Shigella species and to Enteroinvasive *E. coli* (EIEC);

c. not capable of hybridizing or only weakly hybridizing to DNA of bacteria that are in neither the genus Shigella nor the group EIEC.

As used herein, a sequence fragment or oligonucleotide that is "derived from a chromosomal sequence" is a natural, engineered or synthetic molecule having a sequence which is identical or complementary to a chromosomal sequence or is identical or complementary to a variant of the chromosomal sequence. A sequence fragment or oligonucleotide which is identical or complementary to a variant of a selected chromosomal sequence (i.e., the variant differs in sequence from the chromosomal sequence) is a homologue of the sequence or oligonucleotide which is identical or complementary, respectively, to the selected chromosomal sequence. This type of homologue will have a nucleotide sequence substantially similar to a chromosomal sequence and will retain the desired function (will be able to hybridize to substantially the same nucleic acids as the sequence fragment or oligonucleotide which is identical or complementary to that chromosomal sequence under similar hybridization conditions) of the fragment or oligonucleotide which is identical to the selected chromosomal sequence. A homologue may differ from the chromosomal sequence in sequence and/or may contain modified nucleotides or nucleotide analogs (e.g., phosphorothioates, methylphosphonates). A homologue must be able to hybridize to the same nucleic acid as the sequence fragment or oligonucleotide which is identical or complementary to that chromosomal sequence under similar hybridization conditions. It is well known to those skilled in the art that either strand of a double-stranded DNA sequence can serve as the target for a complementary probe. The complement of a given probe is expected to have a substantially similar hybridization pattern, under similar hybridization conditions. The probes may be DNA or RNA or modified DNA or RNA.

Nucleic acid fragments or oligonucleotides containing sequences derived from a chromosomal sequence, their homologues, and complements of all of the foregoing may be used as probes. For example, the Shigella specific fragments, portions thereof and oligonucleotides from the Shigella specific fragments may be used as hybridization probes.

In one embodiment, either of two probe sets of synthetically produced nucleic acid probes (each approximately 40 nucleotides long) will detect substantially all clinically significant serotypes of Shigella, including *S. sonnei*, *S. flexneri*, *S. boydii* and *S. dysenteriae*. Clinically significant serotypes or isolates are those which are human pathogens. In addition, these probe sets recognize some or all enteroinvasive strains of *E. coli*, exclusive of other enteric bacteria tested, with the exception of *Escherichia fergusonii*.

The invention further relates to methods of detecting Shigella species or EIEC in a sample. For example, one or more Shigella serotypes and/or EIEC present in a sample can be detected by lysing the cells in the sample; contacting the sample with a nucleic acid probe or probes of the present invention under conditions that allow the probes to hybridize to Shigella and EIEC DNA in the sample, thus forming hybrid nucleic acid complexes; isolating hybrid nucleic acid complexes formed between the probes and DNA in the sample, and detecting the hybrid nucleic acid complexes as an indication of Shigella or EIEC in the sample. For example, clinical (e.g., stool), environmental (e.g. water), or food specimens may be subjected to such a procedure to ascertain the presence of Shigella and/or EIEC species in the sample.

In preferred embodiments of the method, one or more pairs of probes are selected as a capture and detector probe pair for use in a dual probe liquid hybridization format. These probes can be produced synthetically by chemical or enzymatic synthesis methods. They may be produced as part of a larger molecule. For example, the capture probe can be tailed with 150–200 deoxyadenosine triphosphate (dATP) residues using the enzyme terminal deoxynucleotidyl transferase. The detector probe can be incorporated into an amplification/detection system, such as a biotin-streptavidin-alkaline phosphatase system. Both the capture and detector probes are then allowed to hybridize to the target nucleic acid in a background of competitor nucleic acid from the sample. The hybrid products can be captured out of the mixture by magnetic beads complexed with tails of deoxythymidine monophosphate generally 14 residues longer. The captured hybrids (i.e., those affixed to or captured on the magnetic beads) are detected by means of the amplification/detection system selected.

Isolation of Shigella-Specific Fragments

Shigella-specific genomic sequences were isolated by subtractive hybridization using biotin-streptavidin agarose affinity column chromatography methods described by Langer et al. (Langer, P. R. et al., *Proc. Natl. Acad. Sci. USA*, 78:6633–6637 (1981) and Welcher et al. (Welcher, A. A. et al., *Nucleic Acids Res.*, 14: 10027–10044 (1986)), each of which is incorporated herein by reference. The method is outlined in FIG. 1.

For example, a mixture of competing DNAs, such as the complex DNA competitor mix described in FIG. 1 can be used. In general, a complex DNA competitor mix will contain an excess of DNA (relative to the target DNA) from one or more Enterohemorrhagic *E. coli* isolates, one or more Enterotoxigenic *E. coli* isolates, and one or more non-pathogenic *E. coli* isolates. The mix may further contain specific sequences already recovered or sequences designed to eliminate non-specific sequences. For example a plasmid containing a 17 kb region of the Shigella virulence plasmid such as pHS4033, Class III repeat DNA, or M13mp18 RF DNA may be included.

The particular complex DNA competitor mix used contained a 6-fold excess by weight of DNA (relative to the target DNA) from each of Enterohemorrhagic *E. coli* isolate IG 3040, Enterotoxigenic *E. coli* isolate IG 3060, and non-pathogenic *E. coli* (YMC). The mix further contained DNA, in amounts equal to the target DNA by weight, from each of the following: a pBR322 clone containing a 17 kb region of the Shigella virulence plasmid (plasmid pHS4033, Boileau, C. R. et al., *J. Clin. Microbiol.* 20(5): 959–961 (1984)), M13mp18 RF DNA, and the sequence of the Class III repeat (Class IIIR-IG900) cloned into pBR322. (The 1.3 kb Class III repeat and adjacent chromosomal DNA was cloned into pBR322. The length of the insert was 3.5 kb.) The complete mixture was labelled with biotin-11-dUTP by the nick-translation method. The "target DNA" from which specific sequences were identified was isolated from a single Shigella species, digested with restriction endonuclease Sau3A, and end-labelled with $^{32}$P in an end-filling reaction with DNA polymerase I.

The two DNA pools were combined such that the competing DNAs were at a 20–40 fold molar excess relative to the Shigella DNA. The mixture was denatured and hybridized in liquid at low stringency overnight. The hybridization buffer contained 0.75M NaCl, 50 mM NaPO$_4$, 1 mM EDTA, 0.05% SDS and 40% formamide. The hybridization mixture then was passed over the streptavidin agarose column. Shigella DNA sequences that were sufficiently complementary to the competing DNAs to form hybrids under the conditions used were retained on the streptavidin agarose affinity column by virtue of the biotin incorporated into the competitor DNA. In contrast, sequences that were unable to form hybrids under those conditions were enriched in the nucleic acid fraction passing through the column. The latter sequences contain Shigella-specific sequences.

A small aliquot of the DNA enriched for Shigella-specific sequences (previously $^{32}$P-labelled) was used to probe Shigella and *E. coli* DNAs of interest (0.1 µg of each DNA was spotted in a 3 µl volume on nitrocellulose). Hybridization conditions were those described below in Example II for nick-translated fragments. Cross-hybridization to the competitor *E. coli* provided an indication that further enrichment of the Shigella "target" DNA was required. Typically, four cycles of competition hybridization versus the biotinylated *E. coli* competitor DNA were necessary to eliminate the cross-hybridization. This was accomplished by repeating the competition hybridization/affinity capture cycle, using the Shigella DNA which passed through the column during the previous cycle, as the starting material for the next cycle. In this way, the labeled Shigella target DNA was progressively enriched for Shigella-specific sequences in each cycle.

The nucleic acid which was enriched for Shigella-specific sequences was then used to probe a Sau3A library of the same Shigella isolate used as the "target DNA" in the subtractive hybridization; the library was constructed in the plasmid vector, pUC18. Inserts (fragments) from positive clones were purified from the vector, labelled with $^{32}$P by nick-translation and used to probe mini-cyto-dot panels of inclusivity and exclusivity organisms as described in Examples I and II. A probe shows inclusivity toward an organism if DNA from the organism hybridizes to the probe, and shows exclusivity toward an organism if the probe does not hybridize (or if hybridization is barely detectable) to DNA from that organism under the particular hybridization conditions used.

In most cases, hybridization to inclusivity organisms was much stronger than hybridization to competitors or exclusivity organisms. When necessary, subcloning was done to remove the sequences which cross-hybridized to competitors. At this point, the fragments were labelled with $^{32}$P by nick-translation and used to probe full inclusivity and exclusivity cyto-dot panels.

The inclusivity panels consisted of bacteria representing all known Shigella serotypes as well as Enteroinvasive *E. coli* which exhibit the same pathogenesis as Shigella. These organisms are listed in Tables 2 through 6. The exclusivity panels consisted of non-pathogenic *E. coli*, Enterotoxigenic *E. coli*, Enteropathogenic *E. coli*, Enterohemorrhagic *E. coli*, other Escherichia species and gram negative Enterobacteriaceae. The exclusivity organisms are listed in Tables 6 and 7a/7b.

In the Tables, under the conditions used, (–) indicates no signal, (±) or (±) was barely detectable, (+) indicates a weak but reproducible and readily detectable signal, (++) indicates a moderate signal, (+++) indicates a strong signal, and (++++) indicates a signal comparable to the positive control (DNA from the organism from which the fragment was isolated, or a known sequence identical to the probe being tested). The genomic (chromosomal) DNA fragments identified by the subtractive hybridization and refinement protocols described above are referred to as Shigella specific fragments.

1. Shigella specific fragments NT19-2 (SEQ ID NO: 11) and NT18-1a (SEQ ID NO: 10) were isolated from a library of *Shigella flexneri* (ATCC 29903) genomic clones by probing the library with Shigella specific sequences isolated from *S. flexneri* (ATCC 22903) ³²P-labeled "target" DNA, using the "complex DNA competitor mix" described above in the subtractive hybridization steps.

2. Shigella specific fragments NT 6 (see SEQ ID NO: 1), NT11-2 (SEQ ID NO: 2), NT14 (SEQ ID NO: 4) and NT15 (SEQ ID NO: 3) were isolated from a library of *Shigella sonnei* (ATCC 29930) genomic clones by probing the library with Shigella specific sequences isolated from *S. sonnei* (ATCC 29930) ³²P-labeled "target" DNA and using a single non-pathogenic *E. coli* (YMC) and 1 µg of pBR322 vector DNA as source of competitor DNA in the subtractive hybridization. In this case, avidin agarose rather than streptavidin agarose was used in the affinity column.

The hybridization results against inclusivity and exclusivity organisms for these Shigella-specific fragments are recorded in Tables 2–7. In addition, a set of ompA probes were developed from published data (G. Braun, et al., *Nucleic Acids Research*, 10:2367–2378 (1982)) by comparison of the outer membrane protein gene sequence (ompA) of *Shigella dysenteriae* (SEQ ID NO: 12) with that of *E. coli*. (SEQ ID NO: 13) The regions of ompA gene sequence which appeared most different between the two sequences were selected for the development of test probes. These were synthesized and assayed by hybridization analysis as described above.

Isolation of Shigella-Specific Oligonucleotides

The Shigella-specific fragments described above displayed the most marked specificity for inclusivity organisms of the Shigella DNA fragments analyzed. These fragments were sequenced and oligonucleotide probes useful as capture and detector probes were designed from these sequences. Oligonucleotide capture and detector probes were also designed from a fragment of the ompA sequence by comparative sequence analysis. Following synthesis, the oligonucleotides were end-labelled with ³²P and tested by cyto-dot hybridization analysis as described in Example I to ensure that they exhibited the desired inclusivity and exclusivity behavior or pattern. In several cases, an additional exclusivity panel was tested at this point (Table 8). This panel consisted of 4 µg DNA dots of gram positive and gram negative bacteria-including aerobic and anaerobic representatives commonly found in stool. The DNA was isolated by a protocol which makes use of glass beads to physically disrupt the cell wall of bacteria. Each DNA was spotted on nitro-cellulose filters in a 3 µl volume; the DNAs were denatured, neutralized and fixed as described in Example I for the preparation of cyto-dot panels.

Description of Probes and Hybridization Behavior With Respect to Inclusivity and Exclusivity Oligonucleotide probes were derived from the Shigella-specific fragments identified by affinity chromatography and from the ompA sequence. The sequence of each oligonucleotide probe and the Shigella-specific DNA fragment that each was derived from are listed in Table 9. The inclusivity and exclusivity hybridization behavior of the clones and subclones, and the oligonucleotides designed from these sequences are described below.

Fragment NT6 and Probes 1500, 1501, and 1911

NT6 (See SEQ ID NO: 1) is a 124 bp Sau3A Shigella specific fragment. The sequence is repeated 6 times in *Shigella sonnei* (ATCC 29930) chromosomal DNA. It is also found in one or two copies on the virulence plasmid of other Shigella isolates. The entire fragment was sequenced (FIG. 2). The first 124 bp of FIG. 2 are from NT6 (see SEQ ID NO: 1). The Sau3A site at the 3'-end of the NT-6 sequence is indicated. In this and other Figures, IUPAC conventions for referring to nucleotides and sequence ambiguities are used:

| | |
|---|---|
| Unambiguous bases: | A, C, G, and T (or U) |
| Two possible bases: | M (A or C) |
| | R (A or G) |
| | W (A or T) |
| | S (C or G) |
| | Y (C or T) |
| | K (G or T) |
| Three possible bases: | B (C, G or T) |
| | D (A, G or T) |
| | H (A, C or T) |
| | V (A, C or G) |
| Four possible bases: | N (A, C, G or T) |

Where there is a weak band on the sequencing gel, but no other band, the base is indicated by a lower case letter. Regions of ambiguous nucleotide order due to band compression are enclosed in parentheses.

Two oligonucleotides derived from NT6, each 35 bases long (1500, SEQ ID NO: 14) and 1501 SEQ ID NO: 15), were designed and can be used as capture and detection probes (Table 9). A third probe, 40 bases long (1911, SEQ. ID NO: 16), was designed from NT6 and from additional sequence adjacent to the Sau3A NT-6 fragment (38 bp; see SEQ ID NO: 1). This additional sequence was obtained from a clone isolated from an *S. sonnei* library using the NT-6 124 bp fragment as a probe. A sequencing primer internal to NT-6 was used for sequencing. Oligonucleotide 1911 was designed and tested. The hybridization pattern of 1911 was identical to that of NT6, suggesting it is part of the repeated element.

The individual oligonucleotides were tested for hybridization to inclusivity and exclusivity organisms. In cases where all three probes displayed the same hybridization pattern, the results are not listed separately. The individual oligonucleotides, like the parent fragment, hybridized (using a + signal as the lower limit of hybridization) to all *S. sonnei* isolates tested, many *S. dysenteriae* and *S. boydii*, *S. flexneri* serotypes, including *S. flexneri* type 6 (Tables 2 through 5 and summary Table 10). The oligonucleotide probes derived from NT6 hybridized to all Enteroinvasive *E. coli*, but not to other classes of pathogenic *E. coli*, non-pathogenic *E. coli* or other organisms commonly found in stool (Tables 6–8).

Fragment NT11-2 and Probes 1682, 1683, 1708 and 1709

NT11-2 (SEQ ID NO: 2) is a 796 bp Hha I subclone of an original Sau3A fragment (NT11) which was 3.5 kb in length. Fragment NT11-2 has been sequenced (FIGS. 3A–3B; SEQ ID NO: 2). Two sets of oligonucleotide probes, useful as a capture/detector probe pair were designed from opposite ends of the fragment. Probes 1682 (SEQ ID NO: 17) and 1683 (SEQ ID NO: 18) are 41 nucleotides long, (Table 9). Probes 1708 (SEQ ID NO: 19) and 1709 (SEQ ID NO: 20) are 35 and 36 nucleotides long, respectively. When used as capture/detector probes, each capture probe can be synthesized with an additional three nucleotides (TAT) at the 3' end to ensure efficient tailing by the enzyme terminal deoxynucleotidyl transferase. Tables 2 through 5 and summary Table 10 show that the two sets of oligonucleotides have different hybridization patterns. The cumulative hybridization pattern using the four probes together is the same as that of the parental fragment, NT 11-2, which hybridizes to all *S. sonnei* isolates, and to some *S. dysenteriae*, *S. flexneri* and *S. boydii* isolates. However, when used as capture/detector probe pairs (i.e., 1682 paired with 1683 or 1708 paired with 1709), certain serotypes would not be detected because one partner of each probe set does not hybridize to the isolate (e.g., *S. dysenteriae* types 9 and 10, *S. boydii* type 17). One of the four Enteroinvasive *E. coli* is detected strongly with 1708/1709 and weakly with 1682/1683. Two pathogenic *E. coli* isolates would be detected by 1708/1709 while only one of these isolates would be detected with 1682/1683. Apart from these pathogenic isolates, the oligonucleotides do not cross-hybridize to other non-pathogenic *E. coli* or other organisms commonly found in stool (Tables 6 and 7a).

Fragments NT14 and NT15, and Probes 437 and 1864

NT14 (SEQ ID NO: 4) and NT15 (SEQ ID NO: 3) are Sau3A fragments which are approximately 800 bp and 600 bp in size, respectively. The two fragments have been sequenced and are portions of a highly repeated element which is 1.3 kb in length. One representative repeat each from *S. sonnei* (ATCC 29930) and *S. flexneri* (ATCC 29903) and two repeats from *E. coli* (IG900) were cloned and sequenced (FIGS. 4A–4F; *S. sonnei* repeat, SEQ ID NO: 3 and SEQ ID NO: 4; *E. coli* repeat 1, SEQ ID NO: 5; *E. coli* repeat 2, SEQ ID NO: 6 and SEQ ID NO: 7; *S. flexneri* repeat, SEQ ID NO: 8 and SEQ ID NO: 9). The repeat is highly conserved and has characteristics of a transposable element. Over 20 copies of the repeat sequence are present in the chromosome and virulence plasmid of Shigella. The repeat occurs in 1 to 3 copies in some *E. coli* competitors, but not in other bacterial species.

There are only a few differences between the *E. coli* and *S. sonnei* sequences shown in FIGS. 4A–4F. A 17 base oligonucleotide probe (probe 1864, SEQ ID NO: 22) was designed such that a single mismatch is located eight bases from either end of the probe (Table 9). This probe hybridizes strongly to the majority of Shigella and EIEC tested and does not cross-hybridize to competitor bacteria (Tables 2–8 and summary Table 10). A companion detector probe can be designed within the boundaries of the Class III repeat on either side of the specific capture probe, 1864. One such example is the complement of probe 437 (49 bases) for which inclusivity and exclusivity is listed in Tables 2 through 8. This probe hybridizes strongly to all serotypes of Shigella except *S. boydii* serotype 13.

Probe 437 (SEQ ID NO: 21) hybridizes weakly to a number of non-pathogenic and pathogenic strains of *E. coli*, but does not hybridize to other Enterobacteriaceae tested. The hybridization signal with certain *E. coli* is due to the low copy number of the Class III repeat in this genus versus the high copy number of the repeat in the genus Shigella.

Two extra bases incorporated into the sequence of probe 437 as a result of sequencing errors in the *S. sonnei* sequence (a G and a T) have proved useful in decreasing the signal for *E. coli* isolates relative to Shigella strains. The 437 probe does not hybridize as well as expected to the positive control for *S. sonnei* or *S. flexneri*, suggesting that the two nucleotides in question are not present in the *S. sonnei* sequence. This observation also is likely to be related to copy number differences between the two genera.

Probe 1864 (SEQ ID NO: 22) hybridized to all isolates of *S. dysenteriae* tested except for one isolate of serotype 1 (IG 826). However, serology on this isolate was not confirmed.

Fragment NT18-1a and Probes 1712 and 1713

NT 18-1a (SEQ ID NO: 10) was subcloned from the original Sau3A fragment, NT18, in two steps. A PstI/SacI double digest of NT18 (1500 bp) yielded fragment NT18-1 (1250 bp), which was then restricted with HaeIII to generate NT18-1a (630 bp). Sequences related to fragment NT18 are also known to occur on a small multicopy plasmid which is distinct from the 215 kbp invasion plasmid. The sequence of NT18-1a is shown in FIGS. 5A–5B (SEQ ID NO: 10). Oligonucleotide probes 1712 (SEQ ID NO: 23) and 1713 (SEQ ID NO: 24), suitable as capture/detection probes, both 37 bases long, were designed from the sequence (FIGS. 5A–5B and Table 9). The hybridization pattern (isolates detected) of the oligonucleotide probes was identical to the parental Shigella specific fragment NT18-1a with the exception of one *S. flexneri* isolate (Tables 2–5, 7b). This strain (IG 711) was detected by oligonucleotide probe 1713, but not by probe 1712. In a liquid hybridization assay when the two probes would be used as a capture/detection probe pair this organism would not be detected. Under the conditions used, the probes hybridize to ⅝ type 1 *S. dysenteriae*, to all *S. flexneri* isolates with the exceptions of three type 6 isolates, the IG711 isolate mentioned above, IG872, IG741, and IG709 (Tables 2 through 5 and summary Table 10). The probes do not detect Enteroinvasive *E. coli*, but cross-hybridize to one pathogenic *E. coli* under the conditions used. They do not cross-hybridize to non-pathogenic *E. coli* or other bacteria commonly found in stool (Tables 6 through 8).

Fragment NT19-2 and Probes 1684 and 1685

Fragment NT19-2 (388; bp SEQ ID NO: 11) is an RsaI subclone of the original Sau3A fragment which was 1070 bp in length. NT19-2 was sequenced (FIGS. 6A–6B; SEQ ID NO: 11) and oligonucleotide probes 1684 (SEQ ID NO: 25) and 1685 (SEQ ID NO: 26), each 35 nucleotides long, were designed (Table 9). These probes are suitable as capture/detection probes. The hybridization patterns or spectrum of isolates detected by the individual oligonucleotides and the parental fragment are identical. Hybridization to some *S. boydii*, some *S. sonnei* and all *S. flexneri* except type 6 was observed (Tables 2–5, summary Table 10). The probes hybridize to one out of five Enteroinvasive *E. coli*, and do not cross-hybridize to other pathogenic *E. coli*, non-pathogenic *E. coli* or other bacteria commonly found in stool (Tables 6–8).

ompA Fragment and probes 1706 and 1707

Oligonucleotides 1706 (SEQ ID NO: 27) and 1707 (SEQ ID NO: 28) were designed from the published sequence of the outer membrane protein gene (ompA) of Shigella dysenteriae. FIG. 7 shows the *S. dysentaeriae* ompA gene sequence from nucleotide position 893 through 1076, according to the numbering of Braun et al. (*Nucl. Acids Res.* 10(7): 2367–2378 (1982) SEQ ID NO: 12). This region contains significant differences between the *E. coli* and *S. dysenteriae* ompA coding sequences. The sequence of the corresponding region of the *E. coli* ompA gene is shown for comparison (SEQ ID NO: 13), and the positions of probes 1706 (SEQ ID NO: 27) and 1707 (SEQ ID NO: 28) are indicated in FIG. 7.

Both oligonucleotides are 35 bases long (Table 9). Probe 1706 has 7 differences between the *E. coli* and the *S. dysenteriae* sequence. The region from which probe 1707 was designed is 15 bases shorter in *E. coli*. Additionally, there are numerous differences in that probe site between *E. coli* and *S. dysenteriae*. These probes hybridize with *S. dysenteriae* types 1 and 2 and many *S. boydii* serotypes (Tables 2–5, summary Table 10). When probe 1707 is used as the specific capture probe and 1706 is used as the detector probe in liquid hybridization, no hybridization is anticipated to Enteroinvasive *E. coli*, other pathogenic *E. coli*, non-pathogenic *E. coli* and other bacteria commonly found in stool with the exception of *Escherichia fergusonii* (Tables 6–8).

Description of Probe Sets

Probe Set I

A desired inclusivity/exclusivity pattern may be achieved by use of various combinations of probes. One possible strategy involves pooling one or more combinations of probe pairs to make a probe set. For example, capture/ detection oligonucleotides designed from fragments NT 6 (SEQ ID NO: 1), NT 19-2 (SEQ ID NO: 11) and the ompA gene (SEQ ID NO: 12) may be used together as a probe set or combination for detection of substantially all clinically significant Shigella serotypes. One possible probe set comprises three capture/detection probe pairs, including probe pairs 1684/1685, 1707/1706, and a pair selected from probes 1500/1911/1501. This substantially inclusive probe set detects all Shigella serotypes except for *S. dysenteriae* type 10 and *S. boydii* type 13 (using a + signal as a lower limit for hybridization). In addition, this probe set does not cross-hybridize under the conditions used to any of the competitors tested except for *Escherichia fergusonii*.

The two Shigella serotypes that are not detected by probe set I under these conditions, are rarely isolated in the United States, as indicated by records of the Center of Disease Control. For example, out of a total of 167,915 cases of Shigella infection reported by the Center for Disease Control for the years 1976 through 1987, only two cases were identified as *S. dysenteriae* type 10 and three cases as *S. boydii* type 13.

In a capture/detection assay format, the more specific oligonucleotide of a capture/detector pair is preferred as the capture probe. In the case of the 1684/1685 probe set, either oligonucleotide may serve as the capture probe with equivalent hybridization results. However, in the case of the 1707/1706 probe set, oligonucleotide 1707 is preferred as the capture probe since it does not cross-hybridize to competitors. (Probe 1706 has (±) hybridization signal with certain competitors and a strong signal with an *E. blattae* isolate (Tables 6, 7b)).

In the case of the 1500/1911/1501 oligonucleotide probes, it is best to use either 1500 or 1911 as the capture probe. Probe 1501 has a (±) hybridization signal with certain competitors (Table 8), but may be used as a detector probe with no adverse effects.

Probe Set II

An alternative probe set combines capture/detection oligonucleotide probe pairs from the Class III repeat (fragments 14 and 15; SEQ ID NO: 4 and SEQ ID NO: 3, respectively) and the ompA gene (SEQ ID NO: 12). This substantially inclusive probe set 1707/1706 and 1864/437-complement) hybridizes to all Shigella except *S. boydii* type 13 and cross-hybridizes weakly to *Escherichia fergusonii*.

In the case of the capture/detector pair 1864/437-complement, it is best to use oligonucleotide 1864 as the capture probe since it is the more specific probe of the pair. Oligonucleotide probes designed from sequences to the left or right (in the 5' or 3' direction and from the same strand) of the sequences from which probe 1864 was derived may also serve as detector probes. The complement of probe 437 is one such example, and is expected to substantially retain the hybridization pattern of probe 437.

Use of probe combination II requires only four oligonucleotides instead of six, yet gives the desired inclusivity and exclusivity (substantially inclusive, in this case). In addition, the target of probe 1864 is present in multiple copies (20–30 copies), and therefore, allows for increased sensitivity. However, carefully controlled hybridization conditions are necessary to maintain exclusivity with probe set II, since the specificity of probe 1864 depends on a single mismatch to differentiate between Shigella and *E. coli* which harbor the repetitive element (Class III repeat).

Table 12 lists the number of isolates expected to be detected by probe set I and probe set II in a capture/detection format using a (++) hybridization signal as the cut-off for detection. The results for probe sets I and II in a capture/detection format are expected to be the same when a (+) signal is used as the cut-off for detection.

Additional Probes

Other probes (double- or single-stranded nucleic acid fragments or oligonucleotides), probe sets or combinations may be derived from the Shigella specific fragments. These fragments or oligonucleotides (probes) "derived from the sequence of Shigella specific fragments", comprise nucleic acid sequences which are identical or complementary to a portion of the sequence of the Shigella specific fragments (and therefore to the Shigella chromosome). In some cases, only a portion of the probe may be identical to the sequence of the original Shigella specific fragment. Portions of a probe which are identical or complementary to the sequence of a Shigella specific fragment can be noncontiguous in the probe.

The preferred probes will retain features of the inclusivity, and if desired, the exclusivity of the Shigella specific fragments. A probe derived from a Shigella specific fragment which "substantially retains the inclusivity behavior of" a selected Shigella specific fragment hybridizes, under the same conditions, to at least one isolate of 90% or more of the (typed) serotypes to which the original fragment hybridizes. An original Shigella specific fragment which hybridizes to at least one isolate of one of the 35 serotypes listed in Table 1 is said to hybridize to that serotype. A probe which "moderately retains the inclusivity behavior of" a selected Shigella specific fragment hybridizes, under the same conditions, to at least one isolate of 83% or more, but less than 90%, of the serotypes to which the original fragment hybridizes. A probe which "partially retains the inclusivity behavior of" a selected Shigella specific fragment hybridizes, under the same conditions, to at least one isolate of 50% or more, but less than 83%, of the serotypes to which the original fragment hybridizes.

Exclusivity was determined using two sets of exclusivity organisms. The exclusivity organisms screened included 152 non-EIEC strains listed in Tables 6, 7A and 7B, and defined here as non-EIEC Enterobacteriaceae exclusivity organisms. In addition, the 91 strains listed in Table 8, comprise a second set of exclusivity organisms defined here as exclusivity organisms commonly found in stool.

A probe derived from a Shigella specific fragment which has "improved" exclusivity behavior for a given set of exclusivity organisms (e.g., non-EIEC Enterobacteriaceae) is one for which all of the exclusivity organisms of that set have been screened in the dot blot format, and which detects (hybridizes with a signal of (+) or better) fewer exclusivity organisms of that set than the Shigella specific fragment from which it is derived, under the same hybridization conditions. A probe derived from a Shigella specific fragment which, for a given set of exclusivity organisms, "substantially retains" the exclusivity behavior of the fragment from which it is derived, is one for which 90% or more of the exclusivity organisms of that set have been screened in the dot blot format, and which has substantially the same or identical exclusivity behavior under the same hybridization conditions. In particular, a probe which will detect no more than 13 strains of a set of exclusivity organisms which are not detected by the fragment from which it is derived, and which may or may not detect the exclusivity organisms which are detected by the original fragment, is defined as one which "substantially retains" the exclusivity behavior of that fragment. It will be appreciated that a probe for which exclusivity has been determined for 100% of a given set of exclusivity organisms, but which detects the same number of exclusivity strains or more (but not more than 13 additional strains) of the exclusivity organisms as the original fragment falls in this latter category.

Furthermore, a probe for which exclusivity has not been determined for 100% of the organisms may be shown to have "improved" exclusivity behavior. For example, probes 1684 (SEQ ID NO: 25) and 1685, (SEQ ID NO: 26), for which the exclusivity for 4 non-EIEC Enterobacteriaceae has not been determined, do not detect two strains in Table 6 which are detected by NT19-2 (SEQ ID NO: 11). If it is determined that these probes do not detect three or four of the strains not tested, then they will have improved exclusivity behavior, although they are presently classified as substantially retaining the exclusivity of NT19-2. Thus, the two classifications are not mutually exclusive.

Homologues of fragments and oligonucleotides derived from Shigella specific fragments, which hybridize to substantially the same serotypes as the fragments and oligonucleotides derived from Shigella specific fragments under the same hybridization conditions, can also be used. Homologues of a sequence fragment or oligonucleotide derived from a Shigella specific sequence will be identical or complementary to all or part of a variant of the sequence of a Shigella specific fragment.

For example, oligonucleotide probes, typically from about 10 nucleotides in length up to about 50 nucleotides in length, comprising sequences identical to a portion of a Shigella specific fragment can be designed. However, an oligonucleotide probe may be longer than 50 nucleotides. Larger fragments comprising a sequence identical to a portion of a full length fragment can be prepared by restriction digestion of an isolated clone, exonuclease digestion, by the polymerase chain reaction using selected primers, or other suitable methods, for example.

The additional probes derived from the Shigella specific fragments, complements or homologues thereof, can be screened using a dot blot format (such as the cyto-dot or DNA dot blot formats of the Examples). These additional fragments or oligonucleotide probes can be used alone or in various probe pairs or probe combinations, or in addition to a selected probe, probe pair or combination from Table 9. The additional probes can also be used as alternatives to the probes listed in Table 9. For example, another probe derived from Shigella specific fragment NT11-2 (SEQ ID NO: 2) could be used together with probe 1682 (SEQ ID NO: 17) in place of probe 1683 (SEQ ID NO: 18). For use in a capture/detection format, the probe would be derived from the same strand of the Shigella specific fragments as probe 1682. A probe which substantially retained the inclusivity pattern of NT11-2 could be selected, for example. Furthermore, probes of the present invention can be used in combination with other probes for Shigella, enteroinvasive E. coli, or other organisms (e.g., Salmonella, Campylobacter, etc.).

It will be appreciated that the signal for the recommended probe sets may be increased by using additional probes. Additional probes may be selected from the probes listed in Table 9, oligonucleotide probes derived from the large Shigella specific fragments disclosed, the homologues and complements of any of the foregoing, or other suitable probes. Although some probes are preferred as detection probes in a capture-detection probe format due to hybridization with exclusivity organisms, each probe may be used as either a capture or detection probe.

Inclusivity and Exclusivity Patterns

Different inclusivity and exclusivity patterns can be obtained using selected combinations of probes. Furthermore, inclusivity and exclusivity behavior may be modulated by hybridization conditions, and/or by taking a specific level of hybridization as the cut-off. For example, in Table 10, a (+) signal, which is a weak but reproducible and readily detectable signal, is used as the cut-off for inclusivity or detection in the dot blot format (cyto-dot or DNA dot format).

In Table 11, a (++) cut-off is used. In Table 11, the number of isolates of each serotype or untyped isolate to which the probes NT6, NT11-2, NT18-1a, NT19-2, hybridized with a signal of at least (++) is indicated. In addition, the expected number of isolates of each serotype or untyped isolates to which probe pairs selected from 1911/1500/1501, 1682/1683, 1708/1709, 1712/1713, 1684/1685, or 1706/1707 are expected to hybridize with a signal of at least (++) in a capture/detection format are also indicated. (ND indicates that hybridzation was not determined for a particular isolate.)

Unless indicated otherwise herein, a probe which "detects" or for "the detection" of an isolate or serotype is one which gives at least a (+) signal under the hybridization conditions used with the isolate or with an isolate of a specific serotype. An individual probe (fragments or oligonucleotides), probe pair or probe set (a combination of probes and/or probe pairs) which, under the conditions used in the dot blot format, detects (hybridizes with a signal of at least +) at least one isolate of 90% or more of the serotypes listed in Table 1 is defined as a "substantially inclusive" probe, probe pair, or probe set. Similarly, a probe, probe pair, or probe set which, under the conditions used in the dot blot format, detects at least one isolate of 83% or more, but less than 90%, of the serotypes listed in Table 1 is a moderately inclusive probe, probe pair or probe set. A probe, probe pair or probe set which, under the conditions used in the dot blot format, detects at least one isolate of 50% or more, but less than 83%, of the serotypes listed in Table 1 is a partially inclusive probe, probe pair or probe set.

For example, probe sets I and II described above are substantially inclusive probe sets. Based on the dot blot data (see summary Table 10), these combinations are expected to detect at least one member of 33 and 34 out of 35 serotypes, respectively in a capture/detection format (94.2% and 97.1%). In fact, each of these probe sets is expected to detect every isolate tested of the serotypes detected.

Individual probes such as oligonucleotides 1900, 1500 or 1501, which detect at least one member of 60% of the serotypes listed in Table 1, or fragment NT-6, which detects approximately 68% of the serotypes listed in Table 1 (see Table 10), would be considered partially inclusive probes. Probe 1864 is a substantially inclusive probe. Partially, moderately and substantially inclusive probes may be combined with each other or with other probes into appropriate pairs or sets to achieve a desired inclusivity pattern.

As stated above, the exclusivity organisms screened include the 152 non-EIEC strains listed in Tables 6, 7A and 7B, and defined here as non-EIEC Enterobacteriaceae exclusivity organisms. In addition, the 91 strains listed in Table 8, define a second set of exclusivity organisms defined here as exclusivity organisms commonly found in stool. An individual probe (fragments or oligonucleotides), probe pair or probe set (a combination of probes and/or probe pairs) which, under the conditions used in the dot blot format, does not detect (hybridizes with a signal less than +) any of the 152 non-EIEC strains listed in Tables 6, 7A and 7B is defined as an "exclusive" probe, probe pair or probe set with regard to the non-EIEC Enterobacteriaceae exclusivity organisms. A probe, probe pair, or probe set which, under the conditions used in the Tables, detects (hybridizes with a signal of (+) or better) 10% or less of the 152 non-EIEC strains listed in Tables 6 and 7A and B is defined as a "substantially exclusive" probe, probe pair or probe set with regard to these *E. coli* and Enterobacteriaciae exclusivity organisms, while a probe which detects 20% or less of the 152 non-EIEC strains listed in Tables 6 and 7A and B is defined as "moderately exclusive" of the non-EIEC Enterobacteriaceae exclusivity organisms. A probe which is "exclusive" also meets the criteria for a moderately or substantially exclusive probe.

A probe, probe pair or probe set which, under the conditions used in the dot blot format, does not detect (hybridizes with a signal less than +) any of the 91 strains commonly found in stool and listed in Table 8 is defined as an "exclusive" probe, probe pair or probe set with regard to the exclusivity organisms commonly found in stool. A probe, probe pair, or probe set which, under the conditions used in the Tables, detects (hybridizes with a signal of (+) or better) to 10% or less of the 91 strains listed in Table 8 is defined as "substantially exclusive" of the exclusivity organisms commonly found in stool. Thus, a probe that is exclusive of the organisms in Table 8 is also substantially exclusive of the same organisms.

For example, probes 1500, 1501 or 1911 are exclusive of the non-EIEC Enterobacteriaceae of Tables 6 and 7, as well as of the strains commonly found in stool. Probes 1684 and 1685 did not detect any of the non-EIEC tested; however, 4 organisms (2.6%) were not tested. Thus, 1684 and 1685 are known to be substantially exclusive. If none of these 4 organisms is detected, then these probes would be exclusive. Probe set I, when used in a capture/detection format, is expected to detect 2 of the strains from Table 7 (*Escherichia fergusonii*). However, four strains from Table 7 were not tested (ND). Therefore, probe set I detects at most 3.9% (6/152) of the non-EIEC Enterobacteriaceae, and is thus "substantially exclusive" of the non-EIEC Enterobacteriaceae exclusivity organisms. Probe set I is also exclusive of the exclusivity strains commonly found in stool (listed in Table 8).

Probe 437 detects about 9.9% (15) of the non-EIEC organisms; however, 19/152 of the non-EIEC Enterobacteriaceae were not screened. Thus, the exclusivity of this probe for the non-EIEC Enterobacteriaceae is between 16.4% (moderately exclusive) and 9.9% (substantially exclusive). However, in a capture/detection format, probe set II, which may use the complement of 437, is substantially exclusive of the non-EIEC Enterobacteriaceae exclusivity organisms and exclusive of the exlusivity strains commonly found in stool due to the behavior of probe 1864. The expected behaviour of probe pairs of probe sets I and II in a capture detection format with respect to EIEC, non-EIEC Enterobacteriaceae, and strains commonly found in stool is summarized in Table 13, in which a (+) signal is used as the cut-off for detection. (In Table 13, as in Tables 11 and 12, any pair selected from probes 1500, 1501 and 1911 displays the behavior indicated.)

Assay Formats for Probes

Probes, probe pairs, and probe sets can be used in a variety of hybridization assay formats. Such hybridization assays include solution hybridization assays in which the sequences to be detected and the probes are free in solution, or assays in which one of the sequence or probe is fixed to a solid support. Shigella specific fragments, portions thereof, oligonucleotide probes derived from the fragments, complements, or homologues can be used in dot blot formats or other appropriate hybridization-based assay formats. For example, the large fragments or portions thereof can be prepared as probes by nick translation or other suitable methods for filter hybridization (see e.g., U.S. Pat. No. 4,358,535, Falkow et al.).

The probes can be used in suitable capture detection assay formats (see e.g., D. V. Morrissey, et al., *Analytical Biochemistry*, 181:345-359 (1989); W. R. Hunsaker, et al., *Analytical Biochemistry*, 181:360-370 (1989); H. Lomeli, et al., *Clinical Chemistry*, 35:1826-1831 (1989); Pritchard, C. G. and J. E. Stefano, *Ann. Biol. clin.* 48:492-497 (1990)). In a capture/detector format, the probe pairs are preferably selected from non-overlapping portions of the same strand (a selected strand) of a Shigella specific fragment or a variant of a Shigella specific fragment. The probes can be separated by a distance consistent with activity in the selected assay. Thus, in a standard capture/detection format, the probes should be close enough that sample preparation does not separate the complementary sequences to the extent that the desired sensitivity of detection is compromised.

RNA probes may also be prepared. For example, probe nucleotide sequences can be incorporated into a fal-st MDV cDNA construct, and transcribed from linearized plasmid using T7 RNA polymerase. A detection probe prepared in this way can be used with one or more capture probes and amplified in Qβ replicase system (Pritchard, C. G. and J. E. Stefano, *Ann. Biol. Clin.* 48:492-497 (1990)).

The oligonucleotide probes described or others based on the sequence of the Shigella specific fragments can be used in the polymerase chain reaction. A second oligonucleotide can be prepared from the opposite strand.

The present invention will now be illustrated by the following examples, which are not intended to be limiting in any way.

EXAMPLES

Example 1 Cyto-dot Panels

All cyto-dot panels were prepared by spotting approximately $1 \times 10^8$ cells of each bacterial isolate in a 5 µl volume onto nitrocellulose. The bacteria were lysed and the DNA was denatured by placing the nitrocellulose filters on 3 MM paper wetted with 0.5M NaOH and 1.5M NaCl for 10 minutes. Following this treatment, the nitrocellulose filters were neutralized by placing them on 3 MM paper wetted with 1M Tris pH 7.5 and 1.5M NaCl for 10 minutes. The latter neutralization step was repeated, and the DNA was fixed to the filters by baking under vacuum for 1-1.5 hours at 80° C.

Example 2 Hybridization Conditions

The hybridization conditions for all nick-translated fragments were as follows: Prehybridization—was in 10X Denhardt's, 5X SET, 0.1M phosphate buffer pH 7, 0.1% sodium pyrophosphate, 0.1% SDS for 3 hours at 65° C. (Note that 20X SET is 3M NaCl, 0.4M Tris-HCl pH 7.5 and 20 mM EDTA). Hybridization—was in 2X Denhardt's, 5X SET, 0.1M phosphate buffer pH 7, 0.1% sodium pyrophosphate, 0.1% SDS and $1 \times 10^6$ counts of nick-translated probe per ml of hybridization solution. Hybridizations occurred overnight at 65° C. The autoradiographs were exposed for 15 hours.

The hybridization conditions for all kinased oligonucleotides (except probe 1864, a 17 base (b) oligonucleotide) were as follows:

Prehybridization—was in 5X Denhardt's, 6X SET, 0.1M phosphate buffer pH 7, 0.1% sodium pyrophosphate, 0.1%

SDS for 3 hours at 60° C. Hybridization—was in 1X Denhardt's, 6X SET, 0.1M phosphate buffer pH 7, 0.1% sodium pyrophosphate, 0.1% SDS and 1×10$^6$ counts per minute of kinased oligonucleotide probe per ml of hybridization solution. Hybridizations occurred overnight at 60° C. The autoradiographs were exposed for 15 hours or 7 days. The data recorded in Tables 2–8 are from 7 day exposures. The results of the two exposures were similar. The hybridization conditions for probe 1864 (17 b) were identical to those above except that the prehybridization, hybridization and wash temperatures were 50° C. rather than 60° C.

TABLE 1

SIMPLIFIED OUTLINE OF SHIGELLA CLASSIFICATION

| SPECIES | SEROLOGICAL SUBGROUP | SEROLOGICAL TYPE(S) |
|---|---|---|
| S. dysenteriae | A | 1 through 10 |
| S. flexneri | B | 1 through 6 |
| S. boydii | C | 1 through 18 |
| S. sonnei | D | 1 |

TABLE 2

HYBRIDIZATION RESULTS FOR SHIGELLA DYSENTERIAE SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | ompA 1706 | CR3 437 | CR3 1864 |
|---|---|---|---|---|---|---|---|---|---|---|---|---|---|---|---|---|
| Shigella dysenteriae | | | | | | | | | | | | | | | | |
| RF970, 1 | − | − | − | − | − | − | − | − | − | − | +/− | − | ++++ | ++++ | ++++ | +++ |
| RF952, 1 | − | − | − | − | − | − | − | − | − | − | +/− | − | ++++ | ++++ | ++++ | +++ |
| IG703, 1 | − | − | − | − | − | − | − | ++++ | ++++ | ++++ | +/− | − | ++++ | ++++ | ++++ | +++ |
| IG704, 1 | − | − | − | − | − | − | − | ++++ | ++++ | ++++ | +/− | − | ++++ | ++++ | ++++ | +++ |
| IG705, 1 | − | − | − | − | − | − | − | ++++ | ++++ | ++++ | +/− | − | ++++ | ++++ | ++++ | +++ |
| IG710, 1 | − | − | − | − | − | − | − | ++++ | ++++ | ++++ | +/− | − | ++++ | ++++ | ++++ | +++ |
| IG826, 1 | − | − | − | − | − | − | − | ++++ | ++++ | ++++ | +/− | − | ++++ | ++++ | ++++ | −/+ |
| IG828, 1 | − | − | − | − | − | − | − | ++++ | ++++ | ++++ | +/− | − | ++++ | ++++ | ++++ | +++ |
| IG774, 2 | − | − | +++ | +++ | ++++ | − | − | − | − | − | +/− | − | ++++ | ++++ | ++++ | +++ |
| IG725, 2 | ++ | +++ | +++ | +++ | ++++ | − | − | − | − | − | +/− | − | ++++ | ++++ | ++++ | ++++ |
| IG861, 3 | ++++ | ++++ | − | − | − | − | − | − | − | − | +/− | − | − | − | ++++ | ++++ |
| IG940, 3 | ++++ | ++++ | − | − | − | − | − | − | − | − | +/− | − | − | − | ++++ | ++++ |
| IG941, 3 | ++++ | ++++ | − | − | − | − | − | − | − | − | +/− | − | − | − | ++++ | ++++ |
| IG942, 4 | ++++ | ++++ | − | − | − | − | − | − | − | − | +/− | − | − | − | ++++ | ++++ |
| IG824, 4 | ++++ | ++++ | − | − | − | − | − | − | − | − | +/− | − | − | − | ++++ | ++++ |
| IG862, 4 | ++++ | ++++ | − | − | − | − | − | − | − | − | +/− | − | − | − | ++++ | ++++ |
| IG863, 5 | ++++ | ++++ | − | − | − | − | − | − | − | − | +/− | − | − | − | ++++ | ++++ |
| IG864, 6 | ++++ | ++++ | − | − | − | − | − | − | − | − | +/− | − | − | − | ++++ | ++++ |
| IG865, 7 | +++ | ++++ | − | − | − | − | − | − | − | − | +/− | − | − | − | ++++ | ++++ |
| IG866, 8a | +++ | ++++ | − | − | − | − | − | − | − | − | +/− | − | − | − | ++++ | ++++ |
| IG867, 9a | ++++ | ++++ | ++++ | +++ | +/− | ++ | − | − | − | − | +/− | − | − | − | ++++ | ++++ |
| IG943, 9 | ++++ | ++++ | +++ | +++ | +/− | − | − | − | − | − | +/− | − | − | − | ++++ | ++++ |
| IG944, 9 | ++++ | ++++ | − | − | − | − | − | − | − | − | +/− | − | − | − | ++++ | ++++ |
| IG868, 10 | − | − | +++ | +++ | +/− | ++ | − | − | − | − | +/− | − | − | − | ++++ | ++++ |
| IG706 | ++++ | ++++ | − | − | − | − | − | − | − | − | +/− | − | − | − | ++++ | ++++ |

TABLE 3

HYBRIDIZATION RESULTS FOR SHIGELLA FLEXNERI SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | ompA 1706 | CR3 437 | CR3 1864 |
|---|---|---|---|---|---|---|---|---|---|---|---|---|---|---|---|---|
| Shigella flexneri | | | | | | | | | | | | | | | | |
| IG879, 1a | − | − | − | − | − | − | − | ++++ | ++++ | ++++ | +++ | +++ | − | − | ++++ | +++ |
| IG945, 1a | − | − | − | − | − | − | − | +++ | ++++ | ++++ | +++ | +++ | − | − | ++++ | +++ |
| IG946, 1b | − | − | − | − | − | − | − | ++++ | ++++ | ++++ | +++ | +++ | − | − | ++++ | +++ |
| IG878, 1b | − | − | − | − | − | − | − | ++++ | +++ | +++ | +++ | ++ | − | − | ++++ | ++ |
| IG818, 1b | − | − | − | − | − | − | − | ++++ | ++++ | ++++ | +++ | +++ | − | − | ++++ | +++ |

TABLE 3-continued

HYBRIDIZATION RESULTS FOR *SHIGELLA FLEXNERI* SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|
| RF973, 2a | − | − | − | − | − | − | − | ++++ | ++++ | ++++ | +++ | ++++ | − | − | ++++ | ++++ |
| IG716, 2b | + | − | − | − | − | − | − | ++++ | ++++ | ++++ | +++ | ++++ | − | − | ++++ | ++++ |
| IG877, 3a | ++ | ++ | − | − | − | − | − | ++++ | ++++ | ++++ | ++++ | ++++ | − | − | ++++ | +++ |
| IG947, 3a | − | − | +++ | − | ++ | ++ | +++ | ++++ | ++++ | ++++ | +++ | +++ | − | − | ++++ | +++ |
| IG876, 3b | − | − | +++ | − | ++ | ++ | +++ | ++++ | ++++ | ++++ | +++ | ++++ | − | − | ++++ | +++ |
| IG875, 3c | − | − | ++++ | − | + | ++ | +++ | ++++ | ++++ | ++++ | ++++ | +++ | − | − | ++++ | +++ |
| IG825, 3 | ++++ | ++ | − | − | − | − | − | ++++ | ++++ | ++++ | ++++ | ++++ | − | − | ++++ | ++++ |
| IG874, 4a | − | − | − | − | − | − | − | ++++ | ++++ | ++++ | +++ | ++++ | − | − | ++++ | +++ |
| IG948, 4a | − | − | − | − | − | − | − | +++ | ++++ | ++++ | ++++ | +++ | − | − | ++++ | +++ |
| IG873, 4b | − | − | − | − | − | − | − | ++++ | ++++ | ++++ | +++ | ++++ | − | − | ++++ | ++++ |
| IG838, 4 | − | − | − | − | − | − | − | ++++ | ++++ | ++++ | +++ | +++ | − | − | ++++ | +++ |
| IG872, 5 | − | − | − | − | − | − | − | − | − | − | +++ | ++++ | − | − | ++++ | ++++ |
| IG949, 5 | ++ | ++ | − | − | − | − | − | ++++ | ++++ | ++++ | ++++ | ++++ | − | − | ++++ | +++ |
| IG823, 6 | ++ | ++++ | − | − | − | − | − | − | − | − | +/− | − | − | − | ++++ | ++++ |
| IG871, 6 | ++++ | ++++ | − | − | − | − | − | − | − | − | +/− | − | − | − | ++++ | ++++ |
| IG950, 5 | +++ | ++++ | − | − | − | − | − | − | − | − | +/− | − | − | − | ++++ | ++++ |
| RF951 | ++ | ++ | ++++ | + | − | ++ | +++ | ++++ | ++++ | ++++ | ++++ | ++++ | − | − | ++++ | +++ |
| RF944 | ++ | ++ | ++++ | + | − | ++ | +++ | ++++ | ++++ | ++++ | ++++ | ++++ | − | − | ++++ | +++ |
| RF947 | − | − | − | − | − | − | − | ++++ | ++++ | ++++ | +++ | +++ | − | − | ++++ | +++ |
| RF947 | ++ | ++ | ++++ | + | − | ++ | +++ | ++++ | ++++ | ++++ | ++++ | ++++ | − | − | ++++ | +++ |
| RF950 | − | − | − | − | − | − | − | ++++ | ++++ | ++++ | +++ | +++ | − | − | ++++ | +++ |
| IG763 | ++ | ++ | ++++ | + | − | ++ | +++ | ++++ | ++++ | ++++ | ++++ | ++++ | − | − | ++++ | +++ |
| IG764 | ++ | ++ | ++++ | + | − | ++ | +++ | ++++ | ++++ | ++++ | ++++ | ++++ | − | − | ++++ | +++ |
| IG765 | ++ | ++ | ++++ | + | − | ++ | +++ | ++++ | ++++ | ++++ | ++++ | ++++ | − | − | ++++ | +++ |
| IG766 | ++ | ++ | ++++ | + | − | ++ | +++ | ++++ | ++++ | ++++ | ++++ | ++++ | − | − | ++++ | +++ |
| IG767 | ++ | ++ | ++++ | + | − | ++ | +++ | ++++ | ++++ | ++++ | ++++ | ++++ | − | − | ++++ | +++ |
| IG768 | ++ | ++ | ++++ | + | − | ++ | +++ | ++++ | ++++ | ++++ | ++++ | ++++ | − | − | ++++ | +++ |
| IG770 | ++ | ++ | ++++ | + | − | ++ | +++ | ++++ | ++++ | ++++ | ++++ | ++++ | − | − | ++++ | +++ |
| IG771 | ++ | ++ | ++++ | + | − | ++ | +++ | ++++ | ++++ | ++++ | ++++ | ++++ | − | − | ++++ | +++ |
| IG772 | ++ | ++ | ++++ | + | − | ++ | +++ | ++++ | ++++ | ++++ | ++++ | ++++ | − | − | ++++ | +++ |
| IG773 | ++ | ++ | ++++ | + | − | ++ | +++ | ++++ | ++++ | ++++ | ++++ | ++++ | − | − | ++++ | +++ |
| IG775 | − | − | − | − | − | − | − | ++++ | ++++ | ++++ | ++++ | +++ | − | − | ++++ | ++++ |
| IG777 | ++ | ++ | ++++ | + | − | ++ | +++ | ++++ | ++++ | ++++ | ++++ | ++++ | − | − | ++++ | +++ |
| IG778 | ++ | ++ | ++++ | + | − | ++ | +++ | ++++ | ++++ | ++++ | ++++ | ++++ | − | − | ++++ | +++ |
| IG782 | − | − | − | − | − | − | − | +++ | ++++ | ++++ | +++ | +++ | − | − | ++++ | ++++ |
| IG724 | − | − | ++++ | − | ++ | ++ | +++ | +++ | ++++ | ++++ | +++ | +++ | − | − | ++++ | +++ |
| IG743 | − | − | ++++ | − | − | ++ | +++ | +++ | ++++ | ++++ | +++ | +++ | − | − | ++++ | +++ |
| IG744 | − | − | − | − | − | − | − | ++++ | ++++ | ++++ | +++ | +++ | − | − | ++++ | ++++ |
| IG737 | − | − | − | − | − | − | − | ++++ | ++++ | ++++ | +++ | +++ | − | − | ++++ | ++++ |
| IG735 | − | − | − | − | − | − | − | ++++ | ++++ | ++++ | +++ | +++ | − | − | ++++ | ++++ |
| IG738 | − | − | − | − | − | − | − | ++++ | ++++ | ++++ | +++ | +++ | − | − | ++++ | ++++ |
| IG736 | − | − | +++ | − | ++ | +++ | ++++ | ++++ | ++++ | ++++ | +++ | +++ | − | − | ++++ | +++ |
| IG741 | − | − | − | − | − | − | − | − | − | − | +++ | ++ | − | − | ++++ | +++ |
| IG740 | − | − | − | − | − | − | − | ++++ | ++++ | ++++ | +++ | +++ | − | − | ++++ | ++++ |
| IG739 | − | − | − | − | − | − | − | ++++ | ++++ | ++++ | +++ | +++ | − | − | ++++ | +++ |
| IG742 | − | − | ++++ | − | ++ | ++ | +++ | +++ | ++++ | ++++ | +++ | +++ | − | − | ++++ | +++ |
| IG817 | − | − | − | − | − | − | − | +++ | ++++ | ++++ | +++ | +++ | − | − | ++++ | +++ |
| IG820 | − | − | − | − | − | − | − | ++++ | ++++ | ++++ | +++ | ++ | − | − | ++++ | +++ |
| IG822 | − | − | − | − | − | − | − | +++ | ++++ | ++++ | +++ | +++ | − | − | ++++ | +++ |
| IG709 | − | − | − | − | − | − | − | − | − | − | +++ | ++++ | − | − | ++++ | ++++ |
| IG711 | − | − | − | − | − | − | − | ++++ | − | ++++ | +++ | ++++ | − | − | ++++ | ++++ |
| IG726 | ++ | ++ | ++++ | ++ | +/− | +++ | +++ | ++++ | ++++ | ++++ | ++++ | ++++ | − | − | ++++ | ++++ |

TABLE 4

HYBRIDIZATION RESULTS FOR *SHIGELLA BOYDII* SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|
| *Shigella boydii* | | | | | | | | | | | | | | | | |
| IG832, 1 | +++ | ++++ | − | − | − | − | − | − | − | − | +/− | − | − | − | ++++ | ++++ |
| RF971, 2 | ++++ | ++++ | − | ND | ND | ND | ND | − | ND | ND | +/− | ND | ND | ND | ++++ | ++++ |
| IG880, 3 | ++++ | ++++ | − | − | − | − | − | − | − | − | − | − | − | − | ++++ | +++ |
| IG935, 4 | ++++ | ++++ | − | − | − | − | − | − | − | − | +/− | − | − | − | ++++ | ++++ |
| IG882, 5 | − | − | +++ | +++ | ++++ | ++ | +++ | − | − | − | ++++ | ++++ | ++++ | ++++ | ++++ | ++++ |

TABLE 4-continued

HYBRIDIZATION RESULTS FOR *SHIGELLA BOYDII* SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|
| IG936, 5 | − | − | +++ | +++ | ++++ | ++ | +++ | − | − | − | ++++ | +++ | ++++ | ++++ | ++++ | +++ |
| IG883, 6 | ++++ | ++++ | − | − | − | − | − | − | − | − | +/− | − | − | − | ++++ | ++++ |
| IG884, 7 | + | − | ++++ | +++ | ++++ | ++ | +++ | − | − | − | ++++ | ++++ | ++++ | ++++ | ++++ | −/+ |
| IG885, 8 | ++++ | ++++ | − | − | − | − | − | − | − | − | + | − | − | − | ++++ | ++++ |
| IG829, 9 | − | − | +++ | +++ | ++++ | ++ | − | − | − | − | +++ | − | ++++ | ++++ | ++++ | +++ |
| IG886, 9 | − | − | − | − | − | − | − | − | − | − | +++ | ++++ | ++++ | ++++ | ++++ | +/− |
| IG887, 10 | ++++ | ++++ | − | − | − | − | − | − | − | − | +/− | − | − | − | ++++ | ++++ |
| IG937, 10 | ++++ | ++++ | − | − | − | − | − | − | − | − | +/− | − | − | − | ++++ | ++++ |
| IG3231, 10 | ++++ | ++++ | − | − | − | − | − | − | − | − | +/− | − | − | − | ++++ | ++++ |
| IG938, 11 | − | − | ++++ | +++ | ++++ | ++ | +++ | − | − | − | +++ | ++++ | ++++ | ++++ | ++++ | +++ |
| IG888, 11 | − | − | ++++ | +++ | ++++ | ++ | +++ | − | − | − | ++++ | ++++ | ++++ | ++++ | ++++ | +/− |
| IG889, 12 | + | − | ++++ | +++ | ++++ | − | − | − | − | − | +/− | − | ++++ | ++++ | ++++ | +++ |
| RF974, 13 | − | − | − | − | − | − | − | − | − | − | +/− | − | − | − | − | −/+ |
| IG890, 13 | − | − | − | − | − | − | − | − | − | − | +/− | − | − | − | − | − |
| IG891, 14 | ++++ | ++++ | − | − | − | − | − | − | − | − | +/− | − | − | − | ++++ | ++++ |
| IG939, 14 | +++ | ++++ | − | − | − | − | − | − | − | − | +/− | − | − | − | ++++ | ++++ |
| IG892, 15 | − | − | − | − | − | − | − | − | − | − | +/− | − | ++++ | ++++ | ++++ | +/− |
| IG700, 16 | − | − | +++ | +++ | ++++ | ++ | +++ | − | − | − | ++++ | ++++ | ++++ | ++++ | ++++ | +++ |
| IG701, 17 | − | − | ++++ | + | +++ | +/− | ++++ | − | − | − | ++++ | ++++ | ++ | +++ | ++++ | +++ |
| IG702, 18 | ++++ | ++++ | − | − | − | − | − | − | − | − | +/− | − | − | − | ++++ | ++++ |
| RF948 | ++++ | ++++ | − | − | − | − | − | − | − | − | +/− | − | − | − | ++++ | ++++ |
| IG718 | +++ | ++++ | − | − | − | − | − | − | − | − | +/− | − | − | − | ++++ | +++ |

TABLE 5

HYBRIDIZATION RESULTS FOR *SHIGELLA SONNEI* SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|
| *S. sonnei* | | | | | | | | | | | | | | | | |
| IG827 | ++++ | ++++ | +++ | +++ | ++++ | ++ | +++ | − | − | − | +/− | − | − | − | ++++ | ++++ |
| IG821 | ++++ | ++++ | +++ | +++ | +++ | ++ | +++ | − | − | − | +/− | − | − | − | ++++ | ++++ |
| IG869 | ++++ | ++++ | +++ | +++ | +++ | ++ | +++ | − | − | − | +/− | − | − | − | ++++ | ++++ |
| IG870 | ++++ | ++++ | +++ | ++ | +++ | ++ | +++ | − | − | − | +/− | − | − | − | ++++ | ++++ |
| IG929 | ++++ | ++++ | +++ | +++ | ++++ | ++ | +++ | − | − | − | +++ | ++++ | − | − | ++++ | ++++ |
| IG930 | ++++ | ++++ | +++ | +++ | ++++ | ++ | +++ | − | − | − | +/− | − | − | − | ++++ | ++++ |
| IG931 | ++++ | ++++ | +++ | +++ | ++++ | ++ | +++ | − | − | − | +/− | − | − | − | ++++ | ++++ |
| IG932 | ++++ | ++++ | +++ | +++ | ++++ | ++ | +++ | − | − | − | +/− | − | − | − | ++++ | ++++ |
| IG933 | ++++ | ++++ | +++ | +++ | ++++ | ++ | +++ | − | − | − | +/− | − | − | − | ++++ | ++++ |
| IG934 | ++++ | ++++ | +++ | +++ | ++++ | ++ | +++ | − | − | − | +/− | − | − | − | ++++ | ++++ |
| IG951 | ++++ | ++++ | ++++ | +++ | ++++ | ++ | +++ | − | − | − | +++ | +++ | − | − | ++++ | ++++ |
| IG952 | ++++ | ++++ | +++ | +++ | ++++ | ++ | +++ | − | − | − | +++ | +++ | − | − | ++++ | ++++ |
| IG953 | ++++ | ++++ | +++ | +++ | ++++ | ++ | +++ | − | − | − | +++ | +++ | − | − | ++++ | ++++ |
| IG954 | ++++ | ++++ | +++ | +++ | ++++ | ++ | +++ | − | − | − | +++ | ++++ | − | − | ++++ | ++++ |
| IG955 | ++++ | ++++ | +++ | +++ | ++++ | ++ | +++ | − | − | − | +++ | ++++ | − | − | ++++ | ++++ |
| IG956 | ++++ | ++++ | ++++ | ++++ | ++++ | +++ | ++++ | − | − | − | +++ | ++++ | − | − | ++++ | ++++ |
| IG957 | ++++ | ++++ | +++ | +++ | ++++ | ++ | +++ | − | − | − | +++ | ++++ | − | − | ++++ | ++++ |
| IG958 | ++++ | ++++ | +++ | +++ | ++++ | ++ | +++ | − | − | − | +++ | +++ | − | − | ++++ | ++++ |
| IG959 | ++++ | ++++ | +++ | +++ | ++++ | ++ | +++ | − | − | − | +++ | +++ | − | − | ++++ | ++++ |
| IG960 | ++++ | ++++ | +++ | +++ | ++++ | ++ | +++ | − | − | − | +++ | +++ | − | − | ++++ | ++++ |
| IG961 | ++++ | ++++ | +++ | +++ | ++++ | ++ | +++ | − | − | − | +++ | +++ | − | − | ++++ | ++++ |
| IG962 | ++++ | ++++ | +++ | +++ | ++++ | ++ | +++ | − | − | − | ++++ | ++++ | − | − | ++++ | ++++ |
| IG963 | ++++ | ++++ | +++ | +++ | ++++ | ++ | +++ | − | − | − | +++ | ++++ | − | − | ++++ | ++++ |
| IG964 | ++++ | ++++ | +++ | ++ | ++++ | ++ | +++ | − | − | − | +++ | ++++ | − | − | ++++ | ++++ |
| IG965 | ++++ | ++++ | ++++ | ++++ | ++++ | +++ | ++++ | − | − | − | +++ | ++++ | − | − | ++++ | ++++ |
| RF968 | ++++ | ++++ | +++ | +++ | +++ | ++ | +++ | − | − | − | +++ | +++ | − | − | ++++ | ++++ |
| RF943 | ++++ | ++++ | +++ | +++ | ++++ | ++ | +++ | − | − | − | +/− | − | − | − | ++++ | ++++ |
| RF949 | ++++ | ++++ | +++ | +++ | ++++ | ++ | +++ | − | − | − | +/− | − | − | − | ++++ | ++++ |
| IG781 | ++++ | ++++ | ++++ | +++ | ++++ | ++ | +++ | − | − | − | +/− | − | − | − | ++++ | ++++ |
| IG723 | ++++ | ++++ | ++++ | ++++ | ++++ | +++ | ++++ | − | − | − | +/− | − | − | − | ++++ | ++++ |
| IG717 | ++++ | ++++ | +++ | +++ | ++++ | ++ | +++ | − | − | − | +/− | − | − | − | ++++ | ++++ |
| IG713 | ++++ | ++++ | ++++ | + | +++ | ++ | +++ | − | − | − | +/− | − | − | − | ++++ | ++++ |
| IG714 | ++++ | ++++ | +++ | +++ | ++++ | ++ | +++ | − | − | − | +/− | − | − | − | ++++ | ++++ |
| IG720 | +++ | +++ | +++ | +++ | ++++ | ++ | +++ | − | − | − | +/− | − | − | − | ++++ | ++++ |
| IG719 | ++++ | ++++ | +++ | +++ | ++++ | ++ | +++ | − | − | − | +/− | − | − | − | ++++ | ++++ |

TABLE 5-continued

HYBRIDIZATION RESULTS FOR SHIGELLA SONNEI SEROTYPES

| Genus species Strain ID, serotype | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|
| IG721 | ++++ | ++++ | ++++ | +++ | ++++ | +++ | +++ | − | − | − | +/− | − | − | − | ++++ | ++++ |
| IG712 | ++++ | ++++ | ++++ | + | +++ | ++ | +++ | − | − | − | +/− | − | − | − | ++++ | ++++ |
| IG707 | ++++ | ++++ | +++ | +++ | +++ | ++ | +++ | − | − | − | +/− | − | − | − | ++++ | ++++ |
| IG708 | ++++ | ++++ | ++++ | +++ | ++++ | ++ | +++ | − | − | − | +/− | − | − | − | ++++ | ++++ |
| IG715 | ++++ | ++++ | +++ | +++ | ++++ | +++ | +++ | − | − | − | +/− | − | − | − | ++++ | ++++ |
| IG831 | ++++ | ++++ | +++ | +++ | ++++ | ++ | +++ | − | − | − | +/− | − | − | − | ++++ | ++++ |
| IG830 | ++++ | ++++ | +++ | +++ | ++++ | ++ | +++ | − | − | − | +/− | − | − | − | ++++ | ++++ |
| IG731 | ++++ | ++++ | +++ | +++ | ++++ | ++ | +++ | − | − | − | +/− | − | − | − | ++++ | ++++ |
| IG730 | ++++ | ++++ | +++ | +++ | ++++ | ++ | +++ | − | − | − | +/− | − | − | − | ++++ | ++++ |
| IG733 | ++++ | ++++ | +++ | +++ | ++++ | ++ | +++ | − | − | − | +/− | − | − | − | ++++ | ++++ |
| IG728 | ++++ | ++++ | ++++ | +++ | ++++ | ++ | +++ | − | − | − | +++ | ++++ | − | − | ++++ | ++++ |
| IG732 | ++++ | ++++ | +++ | +++ | ++++ | +++ | +++ | − | − | − | +++ | ++++ | − | − | ++++ | ++++ |
| IG729 | ++++ | ++++ | +++ | +++ | ++++ | +++ | +++ | − | − | − | +/− | − | − | − | ++++ | ++++ |
| IG734 | ++++ | ++++ | +++ | +++ | ++++ | ++ | +++ | − | − | − | +/− | − | − | − | ++++ | ++++ |
| IG727 | ++++ | ++++ | ++++ | +++ | ++++ | ++ | +++ | − | − | − | +/− | − | − | − | ++++ | ++++ |
| IG966 | ++++ | ++++ | ++++ | ++ | +++ | ++ | +++ | − | − | − | +++ | +++ | − | − | ++++ | ++++ |
| IG967 | ++++ | ++++ | +++ | ++ | +++ | ++ | +++ | − | − | − | +++ | +++ | − | − | ++++ | ++++ |
| IG968 | ++++ | ++++ | ++++ | +++ | ++++ | +++ | ++++ | − | − | − | +++ | ++++ | − | − | ++++ | ++++ |
| IG969 | ++++ | ++++ | +++ | +++ | ++++ | ++ | +++ | − | − | − | +++ | +++ | − | − | ++++ | ++++ |
| IG970 | ++++ | ++++ | ++++ | ++++ | ++++ | +++ | ++++ | − | − | − | +++ | +++ | − | − | ++++ | ++++ |
| IG971 | ++++ | ++++ | ++++ | ++++ | ++++ | +++ | ++++ | − | − | − | +++ | ++++ | − | − | ++++ | ++++ |
| IG972 | ++++ | ++++ | +++ | +++ | ++++ | ++ | +++ | − | − | − | +++ | ++++ | − | − | ++++ | ++++ |
| IG974 | ++++ | ++++ | ++++ | ++++ | ++++ | +++ | ++++ | − | − | − | +++ | ++++ | − | − | ++++ | ++++ |
| IG975 | ++++ | ++++ | +++ | ++ | +++ | ++ | +++ | − | − | − | +++ | +++ | − | − | ++++ | ++++ |
| IG976 | ++++ | ++++ | ++++ | ++++ | ++++ | +++ | ++++ | − | − | − | +++ | +++ | − | − | ++++ | ++++ |
| IG979 | ++++ | ++++ | +++ | +++ | +++ | ++ | +++ | − | − | − | +++ | ++++ | − | − | ++++ | ++++ |
| IG980A | ++++ | ++++ | +++ | +++ | ++++ | ++ | +++ | − | − | − | +++ | +++ | − | − | ++++ | ++++ |
| IG980B | ++++ | ++++ | +++ | +++ | ++++ | ++ | +++ | − | − | − | +++ | ++++ | − | − | ++++ | ++++ |
| IG982 | ++++ | ++++ | +++ | +++ | ++++ | ++ | +++ | − | − | − | +++ | ++++ | − | − | ++++ | ++++ |

TABLE 6

HYBRIDIZATION OF SHIGELLA PROBES TO E. COLI

| Genus species | Strain ID | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|---|
| Enteroinvasive | | | | | | | | | | | | | | | | | |
| E. coli | 3138 | ++++ | ++++ | − | − | − | − | − | − | − | − | +/− | − | − | − | − | +++ |
| " | 3145 | ++++ | ++++ | +++ | + | +/− | +++ | ++++ | − | − | − | +/− | − | − | − | + | +++ |
| " | 3146 | ++ | ++++ | − | − | − | − | − | − | − | − | ++++ | ++++ | − | − | + | +++ |
| " | 3157 | ++++ | ++++ | − | − | − | − | − | − | − | − | +/− | − | − | − | ++ | +++ |
| " | 3037 | ++++ | ++++ | − | − | − | − | − | − | − | − | +/− | − | − | − | ++ | −/+ |
| Enterotoxigenic | | | | | | | | | | | | | | | | | |
| E. coli | 3118 | − | − | − | − | − | − | − | − | − | − | +/− | − | − | − | − | − |
| " | 3119 | − | − | − | − | − | − | − | − | − | − | +/− | − | − | − | − | − |
| " | 3120 | − | − | − | − | − | − | − | − | − | − | +/− | − | − | −/+ | − | −/+ |
| " | 3123 | − | − | − | − | − | − | − | − | − | − | +/− | − | − | −/+ | − | − |
| " | 3127 | − | − | − | − | − | − | − | − | − | − | +/− | − | − | −/+ | − | − |
| " | 3129 | − | − | − | − | − | − | − | − | − | − | +/− | − | − | −/+ | ++ | −/+ |
| " | 3132 | − | − | − | − | − | − | − | − | − | − | +/− | − | − | − | + | − |
| " | 3134 | − | − | − | − | − | − | − | − | − | − | +/− | − | − | − | − | − |
| " | 3136 | + | − | − | − | − | − | − | − | − | − | +/− | − | − | − | + | − |
| " | 3142 | − | − | − | − | − | − | − | − | − | − | +/− | − | − | − | − | − |
| " | 3147 | − | − | − | − | − | − | − | − | − | − | +/− | − | − | −/+ | − | − |
| " | 3151 | − | − | − | − | − | − | − | − | − | − | +/− | − | − | − | − | − |
| " | 3154 | − | − | − | ND | − | − | − | − | ND | ND | +/− | − | − | − | − | − |
| " | 3156 | − | − | − | − | − | − | − | − | − | − | +/− | − | − | − | ++ | −/+ |
| " | 3158 | + | − | − | − | − | − | − | − | − | − | + | − | − | − | ++ | ND |
| " | 3160 | − | − | − | − | − | − | − | − | − | − | +/− | − | − | − | + | − |
| Enteropathogenic | | | | | | | | | | | | | | | | | |
| E. coli-0157 serotype | 3137 | − | − | − | − | − | − | − | − | − | − | +/− | − | − | − | − | − |
| " | 3140 | − | − | − | − | − | − | − | − | − | − | +/− | − | − | − | − | − |
| " | 3143 | − | − | − | − | − | − | − | − | − | − | +/− | − | − | − | − | − |

TABLE 6-continued

HYBRIDIZATION OF SHIGELLA PROBES TO *E. COLI*

| Genus species | Strain ID | NT 6 | 1911 1500 1501 | NT 11-2 | 1682 | 1683 | 1708 | 1709 | NT 18-1a | 1712 | 1713 | NT 19-2 | 1684 1685 | ompA 1707 | 1706 | CR3 437 | 1864 |
|---|---|---|---|---|---|---|---|---|---|---|---|---|---|---|---|---|---|
| " | 3144 | − | − | − | − | − | − | − | − | − | − | +/− | − | − | − | − | − |
| " | 3152 | − | − | − | − | − | − | − | − | − | − | +/− | − | − | − | − | − |
| " | 3155 | − | − | − | − | − | − | − | − | − | ND | +/− | − | − | − | − | − |
| " | 3162 | − | − | − | − | − | − | − | − | − | − | +/− | − | − | − | − | − |
| " | 3163 | − | − | − | − | − | − | − | − | − | − | +/− | − | − | − | − | − |
| " | 3164 | − | − | − | − | − | − | − | − | − | − | +/− | − | − | − | − | − |
| " | 3165 | − | − | − | − | − | − | − | − | − | − | +/− | − | − | − | − | − |
| " | 3040 | − | − | − | − | − | − | − | − | − | − | +/− | − | − | − | − | − |
| | | | | | | Enteropathogenic | | | | | | | | | | | |
| *E. coli*-non 0157 serotypes | 3038 | + | − | +++ | + | +++ | ++ | +++ | − | − | − | +/− | − | − | − | − | − |
| *E. coli*-non 0157 serotypes | 3039 | + | − | − | − | − | − | − | +++ | ++++ | ++++ | +/− | − | − | − | + | − |
| *E. coli*-non 0157 serotypes | 3041 | + | − | − | − | − | − | − | − | − | − | + | − | − | − | ++ | ND |
| *E. coli*-non 0157 serotypes | 3042 | − | − | − | − | − | − | − | − | − | − | +/− | − | − | − | − | − |
| *E. coli*-non 0157 serotypes | 3043 | − | − | − | − | − | − | − | − | − | − | +/− | − | − | − | − | − |
| *E. coli*-non 0157 serotypes | 839 | − | − | − | − | − | − | − | − | − | − | +/− | − | − | − | − | − |
| *E. coli*-non 0157 serotypes | 840 | + | − | − | − | − | − | − | − | − | − | +/− | − | − | − | ++ | − |
| *E. coli*-non 0157 serotypes | 841 | − | − | − | − | − | − | − | − | − | − | +/− | − | − | − | − | − |
| *E. coli*-non 0157 serotypes | 842 | − | − | − | − | − | − | − | − | − | − | +/− | − | − | −/+ | − | − |
| *E. coli*-non 0157 serotypes | 843 | − | − | +++ | − | − | ++ | +++ | − | − | − | +/− | − | − | − | − | − |
| *E. coli*-non 0157 serotypes | 844 | − | − | − | − | − | − | − | − | − | − | +/− | − | − | − | − | −/+ |
| *E. coli*-non 0157 serotypes | 845 | − | − | − | − | − | − | − | − | − | − | +/− | − | − | − | + | − |
| *E. coli*-non 0157 serotypes | 846 | ++++ | − | − | − | − | − | − | − | − | − | +/− | − | − | − | − | − |
| *E. coli*-non 0157 serotypes | 847 | − | − | − | − | − | − | − | − | − | − | +/− | − | − | − | − | − |
| *E. coli*-non 0157 serotypes | 848 | − | − | − | − | − | − | − | − | − | − | +/− | − | − | − | − | − |
| *E. coli*-non 0157 serotypes | 3149 | − | − | − | − | − | − | − | − | − | − | +/− | − | − | − | − | − |
| | | | | | | Non-pathogenic | | | | | | | | | | | |
| E. coli | 3116 | − | − | − | − | − | − | − | − | − | − | +/− | − | − | − | ++ | − |
| " | 3117 | − | − | − | − | − | − | − | − | − | − | +/− | − | − | − | − | − |
| " | 3121 | − | − | − | − | − | − | − | − | − | − | +/− | − | − | − | − | − |
| " | 3122 | − | − | − | − | − | − | − | − | − | − | +/− | − | − | − | − | − |
| " | 3124 | − | − | − | − | − | − | − | − | − | − | +/− | − | − | − | − | − |
| " | 3125 | − | − | − | − | − | − | − | − | − | − | +/− | − | − | − | − | − |
| " | 3126 | − | − | − | − | − | − | − | − | − | − | +/− | − | − | − | − | − |
| " | 3128 | − | − | − | − | − | − | − | − | − | − | +/− | − | − | − | + | −/+ |
| " | 3130 | − | − | − | − | − | − | − | − | − | − | +/− | − | − | − | − | − |
| " | 3131 | − | − | − | − | − | − | − | − | − | − | +/− | − | − | −/+ | − | − |
| " | 3133 | − | − | − | − | − | − | − | − | − | − | +/− | − | − | − | − | − |
| " | 3135 | − | − | − | − | − | − | − | − | − | − | +/− | − | − | − | − | − |
| " | 3139 | − | − | − | − | − | − | − | − | − | − | +/− | − | − | −/+ | − | − |
| " | 3148 | − | − | − | − | − | − | − | − | − | − | +/− | − | − | − | − | − |
| " | 3150 | − | − | − | − | − | − | − | − | − | − | +/− | − | − | − | + | − |
| " | 3153 | − | − | − | − | − | − | − | − | − | − | +/− | − | − | −/+ | − | − |
| " | 3158 | − | − | − | − | − | − | − | − | ND | ND | +/− | − | − | − | + | ND |
| " | 3161 | − | − | − | − | − | − | − | − | − | − | +/− | − | − | −/+ | + | ND |

TABLE 7A

HYBRIDIZATION OF SHIGELLA PROBES TO MISC. ENTEROBACTERIACEAE

| Genus species | GT # | ATCC # | NT 6 | 1911 1500 1501 | NT 11-2 | 1682 | 1683 | 1708 | 1709 |
|---|---|---|---|---|---|---|---|---|---|
| Alteromonas putrefaciens | 1495 | 8071 | – | – | – | – | – | – | – |
| Acinetobacter calcoaceticus | 1972 | | – | – | – | ND | ND | ND | ND |
| Citrobacter diversus | 1608 | | – | – | – | – | – | – | – |
| Citrobacter diversus | 1475 | 27156 | – | – | – | – | – | – | – |
| Citrobacter amalonaticus | 1607 | | – | – | – | – | – | – | – |
| Citrobacter amalonaticus | 0689 | 25406 | – | – | – | – | – | – | – |
| Citrobacter amalonaticus | 0690 | 25405 | – | – | – | – | – | – | – |
| Citrobacter freundii | 0041 | | – | – | – | – | – | – | – |
| Citrobacter freundii | 0031 | | – | – | – | – | – | – | – |
| Citrobacter freundii | 1597 | | – | – | – | – | – | – | – |
| Citrobacter freundii | 1476 | 29935 | – | – | – | – | – | – | – |
| Citrobacter freundii | 1477 | 33128 | – | – | – | – | – | – | – |
| Citrobacter freundii | 1491 | 8090 | – | – | – | – | – | – | – |
| Citrobacter freundii | 1591 | | – | – | – | – | – | – | – |
| Citrobacter freundii | 1595 | | – | – | – | – | – | – | – |
| Citrobacter freundii | 1599 | | – | – | – | – | – | – | – |
| Citrobacter freundii | 0685 | | – | – | – | – | – | – | – |
| Citrobacter freundii | 3241 | | – | – | – | – | – | – | – |
| Citrobacter freundii | 0038 | | – | – | – | – | – | – | – |
| Citrobacter freundii | 0036 | | – | – | – | ND | ND | ND | ND |
| Citrobacter freundii | 0035 | | – | – | – | – | – | – | – |
| Citrobacter freundii | 0034 | | – | – | – | – | – | – | – |
| Citrobacter freundii | 0033 | | – | – | – | – | – | – | – |
| Citrobacter freundii | 0032 | | – | – | – | – | – | – | – |
| Citrobacter freundii | 0037 | | – | – | – | – | – | – | – |
| Citrobacter freundii | 0039 | | – | – | – | ND | – | – | – |
| Citrobacter freundii | 0040 | | – | – | – | – | – | – | – |
| Enterobacter aerogenes | 1487 | 29940 | – | – | – | – | – | – | – |
| Enterobacter aerogenes | 0047 | 13048 | – | – | – | – | – | – | – |
| Enterobacter agglomerans | 0048 | | – | – | – | – | – | – | – |
| Enterobacter agglomerans | 0049 | | – | – | – | – | – | – | – |
| Enterobacter agglomerans | 1467 | 29917 | – | – | – | – | – | – | – |
| Enterobacter agglomerans | 1468 | 29918 | – | – | – | – | – | – | – |
| Enterobacter agglomerans | 1469 | 29919 | – | – | – | – | – | – | – |
| Enterobacter agglomerans | 1470 | 29920 | – | – | – | – | – | – | – |
| Enterobacter agglomerans | 1471 | 29921 | – | – | – | – | – | – | – |
| Enterobacter agglomerans | 1472 | 29922 | – | – | – | – | – | – | – |
| Enterobacter agglomerans | 1473 | 29923 | – | – | – | – | – | – | – |
| Enterobacter agglomerans | 1488 | 29904 | – | – | – | – | – | – | – |
| Enterobacter agglomerans | 1489 | 29915 | – | – | – | – | – | – | – |
| Enterobacter agglomerans | 1490 | 29916 | – | – | – | – | – | – | – |
| Enterobacter agglomerans | 1474 | 27998 | – | – | – | – | – | – | – |
| Enterobacter amnigenus | 1482 | 33072 | – | – | – | – | – | – | – |
| Enterobacter cloacae | 0052 | | – | – | – | – | – | – | – |
| Enterobacter cloacae | 3042 | | – | – | – | – | – | – | – |
| Enterobacter cloacae | 0050 | | – | – | – | – | – | – | – |
| Enterobacter cloacae | 3041 | | – | – | – | – | – | – | – |
| Enterobacter cloacae | 1159 | | – | – | – | – | – | – | – |
| Enterobacter cloacae | 1337 | | – | – | – | – | – | – | – |
| Enterobacter cloacae | 1481 | 29941 | – | – | – | – | – | – | – |
| Enterobacter cloacae | 1492 | 13047 | – | – | – | – | – | – | – |
| Enterobacter cloacae | 3043 | | – | – | – | – | – | – | – |
| Enterobacter gergoviae | 1486 | 33028 | – | – | – | – | – | – | – |
| Enterobacter intermedium | 0677 | 33110 | – | – | – | – | – | – | – |
| Enterobacter sakazakii | 0063 | | – | – | – | – | – | – | – |
| Enterobacter sakazakii | 1483 | 29544 | – | – | – | – | – | – | – |
| Enterobacter taylorae | 1497 | 35317 | – | – | – | – | – | – | – |
| Enterobacter taylorae | 0065 | | – | – | – | – | – | – | – |
| Escherichia blattae | 1460 | | – | – | – | – | – | – | – |
| Escherichia fergusonii | 1453 | | – | – | – | – | – | – | – |
| Escherichia fergusonii | 1459 | | – | – | – | – | – | – | – |
| Escherichia hermanii | 1216 | 33650 | – | – | – | – | – | – | – |
| Escherichia vulneri | 1456 | | – | – | – | – | – | – | – |
| Escherichia vulneri | 12217 | 33821 | – | – | – | – | – | – | – |
| Hafnia alvei | 0241 | 29927 | – | – | – | – | – | – | – |
| Hafnia alvei | 1153 | | – | – | – | – | – | – | – |
| Klebsiella oxytoca | 1606 | | – | – | – | – | – | – | – |
| Klebsiella oxytoca | 1605 | | – | – | – | – | – | – | – |
| Klebsiella oxytoca | 1503 | 13182 | – | – | – | – | – | – | – |
| Klebsiella ozaenae | 1499 | 11296 | – | – | – | – | – | – | – |
| Klebsiella planticola | 1478 | 33531 | – | – | – | – | – | – | – |
| Klebsiella pneumoniae | 1150 | | – | – | – | – | – | – | – |
| Klebsiella pneumoniae | 1500 | 13883 | + | – | – | – | – | – | – |

TABLE 7A-continued

HYBRIDIZATION OF SHIGELLA PROBES TO MISC. ENTEROBACTERIACEAE

| Genus species | GT # | ATCC # | NT 6 | 1911 1500 1501 | NT 11-2 | 1682 | 1683 | 1708 | 1709 |
|---|---|---|---|---|---|---|---|---|---|
| Klebsiella penumoniae | 1502 | 29939 | − | − | − | − | − | − | − |
| Klebsiella pneumoniae | 0252 | | − | − | − | − | − | − | − |
| Klebsiella pneumoniae | 1177 | | − | − | − | − | − | − | − |
| Klebsiella terrigena | 1479 | 33257 | − | − | − | − | − | − | − |
| Morganella morganii | 1147 | | − | − | − | − | − | − | − |
| Proteus mirabilis | 1148 | | − | − | − | ND | − | − | ND |
| Proteus mirabilis | 1208 | | − | − | − | − | − | − | − |
| Proteus mirabilis | 1493 | 25933 | − | − | − | ND | ND | ND | ND |
| Proteus mirabilis | 1496 | 29906 | − | − | − | − | − | − | − |
| Proteus mirabilis | 1501 | 7002 | − | − | − | − | − | − | − |
| Proteus vulgaris | 0.370 | | − | − | − | − | − | − | − |
| Providencia stuartii | 3044 | | − | − | − | − | − | − | − |
| Psuedomonas aeruginosa | 3045 | | − | − | − | − | − | − | − |
| Salmonella typhimurium | 0389 | 23566 | − | − | − | ND | ND | ND | ND |
| Serratia marcescens | 0392 | 29937 | − | − | ND | − | − | − | − |
| Serratia marcescens | 1151 | | − | − | − | − | − | − | − |
| Yersinia enterocolitica | 0424 | | − | − | − | − | − | − | − |
| Yersinia enterocolitica | 3219 | | − | − | − | − | − | − | − |

TABLE 7B

HYBRIDIZATION OF SHIGELLA PROBES TO MISC. ENTEROBACTERIACEAE

| Genus species | GT # | ATCC # | NT 18-1a | 1712 | 1713 | NT 19-2 | 1685 | 1684 ompA 1707 | 1706 | CR3 437 | 1864 |
|---|---|---|---|---|---|---|---|---|---|---|---|
| Alteromonas putrefaciens | 1495 | 8071 | − | − | − | +/− | − | − | − | − | − |
| Acinetobacter calcoaceticus | 1972 | | − | ND | ND | +/− | ND | ND | ND | − | − |
| Citrobacter diversus | 1608 | | − | − | − | +/− | − | − | −/+ | − | − |
| Citrobacter diversus | 1475 | 27156 | − | − | − | +/− | − | − | −/+ | − | − |
| Citrobacter amalonaticus | 1607 | | − | − | − | +/− | − | − | −/+ | − | − |
| Citrobacter amalonaticus | 0689 | 25406 | − | − | − | +/− | − | − | −/+ | − | − |
| Citrobacter amalonaticus | 0690 | 25405 | − | − | − | +/− | − | − | −/+ | − | − |
| Citrobacter freundii | 0041 | | − | − | − | +/− | − | − | − | − | − |
| Citrobacter freundii | 0031 | | − | − | − | +/− | − | − | − | − | − |
| Citrobacter freundii | 1597 | | − | ND | ND | +/− | − | − | − | − | − |
| Citrobacter freundii | 1476 | 29935 | − | − | − | +/− | − | − | − | − | − |
| Citrobacter freundii | 1477 | 33128 | − | − | − | +/− | − | − | − | − | − |
| Citrobacter freundii | 1491 | 8090 | − | − | − | +/− | − | − | − | − | − |
| Citrobacter freundii | 1591 | | − | − | − | +/− | − | − | − | − | − |
| Citrobacter freundii | 1595 | | − | − | − | +/− | − | − | − | − | − |
| Citrobacter freundii | 1599 | | − | − | − | +/− | − | − | − | − | − |
| Citrobacter freundii | 0685 | | − | − | − | +/− | − | − | − | − | − |
| Citrobacter freundii | 3241 | | − | − | − | +/− | − | − | −/+ | − | − |
| Citrobacter freundii | 0038 | | − | − | − | +/− | − | − | − | ND | − |
| Citrobacter freundii | 0036 | | − | ND | ND | +/− | ND | ND | ND | ND | − |
| Citrobacter freundii | 0035 | | − | − | − | +/− | − | − | − | ND | − |
| Citrobacter freundii | 0034 | | − | − | − | +/− | − | − | − | ND | − |
| Citrobacter freundii | 0033 | | − | − | − | +/− | − | − | − | ND | − |
| Citrobacter freundii | 0032 | | − | − | − | +/− | − | − | − | ND | − |
| Citrobacter freundii | 0037 | | − | − | − | +/− | − | − | − | ND | − |
| Citrobacter freundii | 0039 | | − | ND | ND | +/− | − | − | − | ND | − |
| Citrobacter freundii | 0040 | | − | − | − | +/− | − | − | − | ND | − |
| Enterobacter aerogenes | 1487 | 29940 | − | − | − | +/− | − | − | − | − | − |
| Enterobacter aerogenes | 0047 | 13048 | − | − | − | +/− | − | − | − | − | − |
| Enterobacter agglomerans | 0048 | | − | − | − | +/− | − | − | − | − | − |
| Enterobacter agglomerans | 1467 | 29917 | − | − | − | +/− | − | − | − | − | − |
| Enterobacter agglomerans | 1468 | 29918 | − | − | − | +/− | − | − | − | − | − |
| Enterobacter agglomerans | 1469 | 29919 | − | − | − | +/− | − | − | − | − | − |
| Enterobacter agglomerans | 1470 | 29920 | − | − | − | +/− | − | − | − | − | − |
| Enterobacter agglomerans | 1471 | 29921 | − | − | − | +/− | − | − | − | − | − |
| Enterobacter agglomerans | 1472 | 29922 | − | − | − | +/− | − | − | − | − | − |
| Enterobacter agglomerans | 1473 | 29923 | − | − | − | +/− | − | − | − | − | − |
| Enterobacter agglomerans | 1488 | 29904 | − | − | − | +/− | − | − | − | − | − |
| Enterobacter agglomerans | 1489 | 29915 | − | − | − | +/− | − | − | +/− | − | − |
| Enterobacter agglomerans | 1490 | 29916 | − | − | − | +/− | − | − | − | − | − |
| Enterobacter agglomerans | 1474 | 27998 | − | − | − | +/− | − | − | − | − | − |
| Enterobacter amnigenus | 1482 | 33072 | − | − | − | +/− | − | − | − | − | − |
| Enterobacter cloacae | 0052 | | − | − | − | +/− | − | − | + | − | − |

TABLE 7B-continued

HYBRIDIZATION OF SHIGELLA PROBES TO MISC. ENTEROBACTERIACEAE

| Genus species | GT # | ATCC # | NT 18-1a | 1712 | 1713 | NT 19-2 | 1684 1685 | ompA 1707 | 1706 | CR3 437 | 1864 |
|---|---|---|---|---|---|---|---|---|---|---|---|
| Enterobacter cloacae | 3042 | | – | – | – | +/– | – | – | – | – | – |
| Enterobacter cloacae | 0050 | | – | – | – | +/– | – | – | – | – | – |
| Enterobacter cloacae | 3041 | | – | – | – | +/– | – | – | – | – | – |
| Enterobacter cloacae | 1159 | | – | – | – | +/– | – | – | – | – | – |
| Enterobacter cloacae | 1337 | | – | – | – | +/– | – | – | – | – | – |
| Enterobacter cloacae | 1481 | 29941 | – | – | – | +/– | – | – | – | – | – |
| Enterobacter cloacae | 1492 | 13047 | – | – | – | +/– | – | – | – | – | – |
| Enterobacter cloacae | 3043 | | – | – | – | +/– | – | – | – | – | – |
| Enterobacter gergoviae | 1486 | 33028 | – | – | – | +/– | – | – | – | – | – |
| Enterobacter intermedium | 0677 | 33110 | – | – | – | +/– | – | – | – | – | – |
| Enterobacter sakazakii | 0063 | | – | – | – | +/– | – | – | – | – | – |
| Enterobacter sakazakii | 1483 | 29544 | – | – | – | +/– | – | – | – | – | – |
| Enterobacter taylorae | 1497 | 35317 | – | – | – | +/– | – | – | – | – | – |
| Enterobacter taylorae | 0065 | | – | – | – | +/– | – | – | – | – | – |
| Escherichia blattae | 1460 | | – | – | – | +/– | – | – | ++++ | – | – |
| Escherichia fergusonii | 1453 | | – | – | – | +/– | – | + | + | – | – |
| Escherichia fergusonii | 1459 | | – | – | – | +/– | – | ++ | +++ | – | – |
| Escherichia hermanii | 1216 | 33650 | – | ND | ND | +/– | – | – | – | – | – |
| Escherichia vulneri | 1456 | | – | – | – | +/– | – | – | – | – | – |
| Escherichia vulneri | 1217 | 33821 | – | – | – | +/– | – | – | – | – | – |
| Hafnia alvei | 0241 | 29927 | – | – | – | +/– | – | – | – | – | – |
| Hafnia alvei | 1153 | | – | – | – | +/– | – | – | – | – | – |
| Klebsiella oxytoca | 1606 | | – | – | – | +/– | – | – | – | ND | – |
| Klebsiella oxytoca | 1605 | | – | – | ND | +/– | – | – | – | ND | – |
| Klebsiella oxytoca | 1503 | 13182 | – | – | – | +/– | – | – | – | – | – |
| Klebsiella ozaenae | 1499 | 11296 | – | – | – | +/– | – | – | – | – | – |
| Klebsiella planticola | 1478 | 33531 | – | – | – | +/– | – | – | – | – | – |
| Klebsiella pneumoniae | 1150 | | – | – | – | +/– | – | – | – | – | – |
| Klebsiella pneumoniae | 1500 | 13883 | – | – | – | +/– | – | – | – | – | – |
| Klebsiella pneumoniae | 1502 | 29939 | – | – | – | +/– | – | – | – | – | – |
| Klebsiella pneumoniae | 0252 | | – | – | – | +/– | – | – | – | – | – |
| Klebsiella pneumoniae | 1177 | | – | – | – | +/– | – | – | – | – | – |
| Klebsiella terrigena | 1479 | 33257 | – | – | – | +/– | – | – | – | – | – |
| Morganella morganii | 1147 | | – | – | – | +/– | – | – | – | – | – |
| Proteus mirabilis | 1148 | | – | ND | ND | +/– | – | – | – | – | – |
| Proteus mirabilis | 1208 | | – | ND | ND | +/– | – | – | – | – | – |
| Proteus mirabilis | 1493 | 25933 | – | ND | ND | +/– | ND | ND | ND | – | – |
| Proteus mirabilis | 1496 | 29906 | – | – | – | +/– | – | – | – | – | – |
| Proteus mirabilis | 1501 | 7002 | – | – | – | +/– | – | – | – | – | – |
| Proteus vulgaris | 0370 | | – | – | – | +/– | – | – | – | – | – |
| Providencia stuartii | 3044 | | – | – | – | +/– | – | – | – | – | –/+ |
| Psuedomonas aeruginosa | 3045 | | – | – | – | +/– | – | – | – | – | – |
| Salmonella typhimurium | 0389 | 23566 | – | ND | ND | +/– | ND | ND | ND | – | – |
| Serratia marcescens | 0392 | 29937 | – | – | – | +/– | – | – | – | – | – |
| Serratia marcescens | 1151 | | – | ND | – | +/– | – | – | – | – | – |
| Yersinia enterocolitica | 0424 | | – | – | – | +/– | – | – | – | – | – |
| Yersinia enterocolitica | 3219 | | – | – | – | +/– | – | – | – | – | – |

TABLE 8

HYBRIDIZATION OF SHIGELLA PROBES TO BACTERIA COMMONLY FOUND IN STOOL

| Genus/Species | GT # | ATCC # | NT 6 1500 | 1501 | 1911 | NT 1902 1684 | 1685 | ompA 1706 | 1707 | CR3 1864 |
|---|---|---|---|---|---|---|---|---|---|---|
| Acinetobacter calcoaceticus | 0002 | 19606 | – | –/+ | – | – | – | – | – | – |
| Acinetobacter lwoffii | 0004 | 9957 | – | – | – | – | – | – | – | – |
| Aeromonas hydrophila | 0006 | 7965 | – | –/+ | – | – | – | – | – | – |
| Aeromonas sobria | 0007 | 9071 | – | – | – | – | – | – | – | – |
| Alteromonas putrefaciens | 1495 | 8071 | – | – | – | – | – | – | – | – |
| Citrobacter amalonaticus | 0690 | 25405 | – | – | – | – | – | – | – | – |
| Edwardsiella tarda | 0569 | 15947 | – | – | – | – | – | – | – | – |
| Haemophilus influenzae | 0244 | 19418 | – | +/– | – | – | – | +/– | – | – |
| Plesiomonas shigelloides | 2197 | 14029 | – | – | – | – | – | – | – | – |
| Providencia alcalifaciens | 0371 | 9886 | – | –/+ | – | – | – | – | – | – |
| Providencia rettgeri | 0373 | 9944 | – | – | – | – | – | – | – | – |
| Providencia stuartii | 0375 | 29914 | – | – | – | – | – | – | – | – |
| Salmonella arizona | 0799 | 13314 | – | – | – | – | – | – | – | – |
| Salmonella typhimurium | 0389 | 23566 | – | +/– | – | – | – | – | – | – |

TABLE 8-continued

HYBRIDIZATION OF SHIGELLA PROBES TO BACTERIA COMMONLY FOUND IN STOOL

| | | | NT 6 | | | NT 1902 | | ompA | | CR3 |
|---|---|---|---|---|---|---|---|---|---|---|
| Genus/Species | GT # | ATCC # | 1500 | 1501 | 1911 | 1684 | 1685 | 1706 | 1707 | 1864 |
| Vibrio parahemolyticus | 0568 | 17802 | – | – | – | – | – | – | – | – |
| Xanthomonas maltophila | 0417 | 13637 | – | – | – | – | – | – | – | – |
| Yersinia enterocolitica | 0419 | 9610 | – | – | – | – | – | – | – | – |
| Yersinia pseudotuberculosis | 0519 | 29833 | – | – | – | – | – | – | – | – |
| Yersinia ruckeri | 0522 | 29473 | – | +/– | – | – | – | – | – | – |
| Alcaligenes denitrificans ss xyloxidans | 0001 | 27062 | – | –/+ | – | – | – | – | – | – |
| Alcaligenes faecalis | 0610 | 875 | – | – | – | – | – | – | – | – |
| Kingella kingae | 0247 | 23330 | – | – | – | – | – | – | – | – |
| Kingella dendrificans | 0245 | 33394 | – | – | – | – | – | – | – | – |
| Kingella indologenes | 0246 | 25869 | – | – | – | – | – | – | – | – |
| Moraxella osloensis | 0301 | 19962 | – | – | – | – | – | – | – | – |
| Neisseria cinerea | 0307 | 14685 | – | – | – | – | – | – | – | – |
| Neisseria flavescens | 0310 | 13120 | – | –/+ | – | – | – | – | – | – |
| Neisseria gonorrhoeae, type | 0315 | 19424 | – | –/+ | – | – | – | – | – | – |
| Neisseria memingitidis | 0348 | | – | –/+ | – | – | – | – | – | – |
| Neisseria mucosa | 0353 | 19696 | – | – | – | – | – | – | – | – |
| Psuedomonas acidovorans, type | 0376 | 15668 | – | – | – | – | – | – | – | – |
| Achromobacter xerosis | 0810 | 14780 | – | – | – | – | – | – | – | – |
| Gardnerella vaginalis | 0240 | 1408 | – | – | – | – | – | – | – | – |
| Acidaminiococcus fermantans | 3129 | 25085 | – | – | – | – | – | – | – | – |
| Ruminococcus bromeii | 3142 | 27255 | – | – | – | – | – | – | – | – |
| Bacteroides gracilis | 0716 | 33236 | – | – | – | – | – | – | – | – |
| Bacteroides ureolyticus | 0715 | 33387 | – | –/+ | – | – | – | – | – | – |
| Campylobacter jejuni, type | 0022 | 33560 | – | – | – | – | – | – | – | – |
| Campylobacter coli | 0016 | 33559 | – | –/+ | – | – | – | – | – | – |
| Campylobacter laridis | 0024 | 35223 | – | – | – | – | – | – | – | – |
| Wolinella curva | 2224 | 35224 | – | – | – | – | – | – | – | – |
| Wolinella recta | 0718 | 33238 | – | – | – | – | – | – | – | – |
| Wolinella succinogenes | 0614 | 29543 | – | – | – | – | – | – | – | – |
| Bacillus cereus | 0008 | 14579 | – | – | – | – | – | – | – | – |
| Butyrivibrio fibrosolvens | 3139 | 19171 | – | – | – | – | – | – | – | – |
| Clostridium difficile | 0043 | 9689 | – | –/+ | – | – | – | – | – | – |
| Clostridium perfringens | 0044 | 3624 | – | –/+ | – | – | – | – | – | – |
| Clostridium sordellii | 0567 | 9714 | – | –/+ | – | – | – | – | – | – |
| Eubacterium lentum | 2196 | 25559 | – | – | – | – | – | – | – | – |
| Eubacterium rectale | 0236 | 35183 | – | –/+ | – | – | – | – | – | – |
| Lactobacillus acidophilus | 0256 | 4356 | – | – | – | – | – | – | – | – |
| Lactobacillus casei | 0805 | 393 | – | – | – | – | – | – | – | – |
| Loctobacillus minutus | 0257 | 33267 | – | –/+ | – | – | – | – | – | – |
| Lactobacillus plantarum | 0258 | 8014 | – | – | – | – | – | – | – | – |
| Listeria grayi | 0674 | | – | +/– | – | – | – | – | – | – |
| Listeria innocua | 0260 | | – | +/– | – | – | – | – | – | – |
| Listeria innocua | 0750 | | – | –/+ | – | – | – | – | – | – |
| Listeria ivanovii | 1037 | | – | +/– | – | – | – | – | – | – |
| Listeria monocytogenes | 1016 | | – | +/– | – | – | – | – | – | – |
| Listeria seeligeri | 0287 | | – | – | – | – | – | – | – | – |
| Listeria welshrimpi | 0291 | | – | +/– | – | – | – | – | – | – |
| Peptococcus asaccharolyticus | 0360 | 29743 | – | – | – | – | – | – | – | – |
| Peptococcus magnus | 0361 | 29328 | – | – | – | – | – | – | – | – |
| Peptostreptococcus anaerobius | 0359 | 27337 | – | – | – | – | – | – | – | – |
| Sarcina maxima | 0391 | 33910 | – | –/+ | – | – | – | – | – | – |
| Staphylococcus aureus | 0399 | 12600 | – | –/+ | – | – | – | – | – | – |
| Staphylococcus epidermiodis | 0401 | 14990 | – | –/+ | – | – | – | – | – | – |
| Streptococcus agalactiae | 0405 | 13813 | – | –/+ | – | – | – | – | – | – |
| Streptococcus faecalis | 0406 | 19433 | – | –/+ | – | – | – | – | – | – |
| Streptococcus faecium | 0407 | 6056 | – | –/+ | – | – | – | – | – | – |
| Streptococcus mutans | 0412 | 25175 | – | –/+ | – | – | – | – | – | – |
| Streptococcus salivarius | 0410 | 13419 | – | –/+ | – | – | – | – | – | – |
| Streptococcus sanguis | 0411 | 10556 | – | +/– | – | – | – | – | – | – |
| Actinomyces israelii | 0005 | 10049 | – | – | – | – | – | – | – | – |
| Bifidobacterium dentium | 0012 | 27534 | – | – | – | – | – | – | – | – |
| Bifidobacterium bifidum | 0571 | 35914 | – | – | – | – | – | – | – | – |
| Corynebacterium smegmatis | 0306 | 6919 | – | – | – | – | – | – | – | – |
| Mycobacterium smegmatis | 0306 | 14468 | – | – | – | – | – | – | – | – |
| Propionibacterium acnes | 0363 | 6919 | – | – | – | – | – | – | – | – |
| Fusobacterium mortiferum | 0573 | 9817 | – | –/+ | – | – | – | – | – | – |
| Fusobacterium necrophorum | 0238 | 25286 | – | – | – | – | – | – | – | – |
| Mobiluncus mulieris | 0300 | 35243 | – | – | – | – | – | – | – | – |
| Veionella atypica | 0413 | 14894 | – | – | – | – | – | – | – | – |
| Bacteroides fragilis | 0010 | 23745 | – | –/+ | – | – | – | – | – | – |
| Bacteroides thetaiotaomicron | 0572 | 29741 | – | –/+ | – | – | – | – | – | – |
| Bacteroides melaninogenicus | 0011 | 25845 | – | – | – | – | – | – | – | – |
| Flavobacterium meningosepticum | 0237 | 13253 | – | –/+ | – | – | – | – | – | – |

TABLE 8-continued

HYBRIDIZATION OF SHIGELLA PROBES TO BACTERIA COMMONLY FOUND IN STOOL

| Genus/Species | GT # | ATCC # | NT 6 | | | NT 1902 | | ompA | | CR3 |
|---|---|---|---|---|---|---|---|---|---|---|
| | | | 1500 | 1501 | 1911 | 1684 | 1685 | 1706 | 1707 | 1864 |
| *Candida albicans* | 0028 | 18804 | — | — | — | — | — | — | +/− | — |
| *Candida glabrata* | 0029 | 2001 | — | — | — | — | — | — | — | — |
| *Candida strellatoidae* | 0609 | 36232 | — | — | — | — | — | — | — | — |
| *Candida tropicalis* | 0570 | 750 | — | — | — | — | — | — | — | — |

TABLE 9

LIST OF OLIGONUCLEOTIDE PROBES DESIGNED FROM SHIGELLA SPECIFIC FRAGMENTS

| Parental DNA fragment | Oligonucleotide Probe No. | Length of probes (bases) | Sequence of oligonucleotide probes |
|---|---|---|---|
| NT 6 (124 b) | 1500 | 35 | 5' TTGCAGCGCCTCTACTACCGGATACAGCCTCCATT 3' |
| | 1501 | 35 | 5' CCTCCTTCAGGGCGGATTCCAGCCGTTCACATTGT 3' |
| | 1911 | 40 | 5' CCGATCTTCTATTGTACGACGGTGTTCGTCAAAAGCTAAT 3' |
| NT 11-2 (900 b) | 1682 | 41 | 5' CTGGTGAACAACGTCTTACAAAGATGGTTCCTGGATGGATT 3' |
| | 1683 | 41 | 5' AGTCTTTCCGTGTTTCTCAGAAATGGGGGCAACGTGCAAAA 3' |
| | 1708 | 35 | 5' CCACCGTTGAAGCGTAAACCGTTTGACCGATGGAT 3' |
| | 1709 | 36 | 5' GCTGGGGTCTACAGGTGCAATAACCACTTAGACGGT 3' |
| NT 14 (800 b) | 437 | 49 | 5' CGATGATGCCATTCTCTGCCAGCTCCGTCTGGGAGCCGCCGGGTTTCC 3' |
| NT 15 (600 b) | 1864 | 17 | 5' GGAGCAGTCTGGTCTGA 3' |
| NT18-1a (631 b) | 1712 | 37 | 5' CCTGTGGCTCTCGGTTCTGATGGTATAGCAACTAAAT 3' |
| | 1713 | 37 | 5' CAAGGATGTTTCGGAATTGAGTGGGGAGTTGCGAAAT 3' |
| NT 19-2 (389 b) | 1684 | 35 | 5' CAGGCAATCGAAGCATATCGCGGTTCTCCACAACT 3' |
| | 1685 | 35 | 5' TGAATGCGCTGACCGAAAACCAGCGCTGGGTATCT 3' |
| ompA | 1706 | 35 | 5' GTGATGGCCCATTCAACACCACCTGCGAATACCGG 3' |
| | 1707 | 35 | 5' CTCAGATTCACCTGTCACATTGTTGTGAGCTTTGG 3' |

TABLE 10

Summary of Probe Hybridization Results to Shigella Serotypes
(+ signal used as a cut-off for detectability)

| SERO-TYPE | TEST ED | NT-5 | 1911 1500 1501 | NT11-2 | 1682 | 1683 | 1708 | 1709 | NT18-1a | 1712 | 1713 | nt19-2 | 1684 | 1685 | 1707 | 1706 | 437 | 1864 |
|---|---|---|---|---|---|---|---|---|---|---|---|---|---|---|---|---|---|---|
| *S. Dysenteriae* | | | | | | | | | | | | | | | | | | |
| 1 | 8 | — | — | — | — | — | — | — | 6 | 6 | 6 | — | — | — | 8 | 8 | 8 | 7 |
| 2 | 2 | 1 | 1 | 2 | 2 | 2 | — | — | — | — | — | — | — | — | 2 | 2 | 2 | 2 |
| 3 | 3 | 3 | 3 | — | — | — | — | — | — | — | — | — | — | — | — | — | 3 | 3 |
| 4 | 3 | 3 | 3 | — | — | — | — | — | — | — | — | — | — | — | — | — | 3 | 3 |
| 5 | 1 | 1 | 1 | — | — | — | — | — | — | — | — | — | — | — | — | — | 1 | 1 |
| 6 | 1 | 1 | 1 | — | — | — | — | — | — | — | — | — | — | — | — | — | 1 | 1 |
| 7 | 1 | 1 | 1 | — | — | — | — | — | — | — | — | — | — | — | — | — | 1 | 1 |
| 8 | 1 | 1 | 1 | — | — | — | — | — | — | — | — | — | — | — | — | — | 1 | 1 |
| 9 | 3 | 3 | 3 | 2 | 2 | — | 1 | — | — | — | — | — | — | — | — | — | 3 | 3 |
| 10 | 1 | — | — | 1 | 1 | — | 1 | — | — | — | — | — | — | — | — | — | 1 | 1 |
| untyped | 1 | 1 | 1 | — | — | — | — | — | — | — | — | — | — | — | — | — | 1 | 1 |
| | 25 | | | | | | | | | | | | | | | | | |
| *S. flexneri* | | | | | | | | | | | | | | | | | | |
| 1 | 5 | — | — | — | — | — | — | — | 5 | 5 | 5 | 5 | 5 | 5 | — | — | 5 | 5 |
| 2 | 2 | 1 | — | — | — | — | — | — | 2 | 2 | 2 | 2 | 2 | 2 | — | — | 2 | 2 |
| 3 | 5 | 2 | 2 | 3 | — | 3 | 3 | 3 | 5 | 5 | 5 | 5 | 5 | 5 | — | — | 5 | 5 |
| 4 | 4 | — | — | — | — | — | — | — | 4 | 4 | 4 | 4 | 4 | 4 | — | — | 4 | 4 |
| 5 | 2 | 1 | 1 | — | — | — | — | — | 1 | 1 | 1 | 2 | 2 | 2 | — | — | 2 | 2 |
| 6 | 3 | 3 | 3 | — | — | — | — | — | — | — | — | — | — | — | — | — | 3 | 3 |
| untyped | 36 | 16 | 16 | 20 | 16 | 2 | 20 | 20 | 34 | 33 | 34 | 36 | 36 | 36 | — | — | 36 | 36 |
| | 57 | | | | | | | | | | | | | | | | | |

TABLE 10-continued

Summary of Probe Hybridization Results to Shigella Serotypes
(+ signal used as a cut-off for detectability)

| SERO-TYPE | TESTED | NT-5 | 1911 1500 1501 | NT11-2 | 1682 | 1683 | 1708 | 1709 | NT18-1a | 1712 | 1713 | nt19-2 | 1684 | 1685 | 1707 | 1706 | 437 | 1864 |
|---|---|---|---|---|---|---|---|---|---|---|---|---|---|---|---|---|---|---|
| *S. boydii* | | | | | | | | | | | | | | | | | | |
| 1 | 1 | 1 | 1 | — | — | — | — | — | — | — | — | — | — | — | — | — | 1 | 1 |
| 2 | 1 | 1 | 1 | — | ND | ND | ND | ND | — | ND | ND | — | ND | ND | ND | ND | 1 | 1 |
| 3 | 1 | 1 | 1 | — | — | — | — | — | — | — | — | — | — | — | — | — | 1 | 1 |
| 4 | 1 | 1 | 1 | — | — | — | — | — | — | — | — | — | — | — | — | — | 1 | 1 |
| 5 | 2 | — | — | 2 | 2 | 2 | 2 | 2 | — | — | — | 2 | 2 | 2 | 2 | 2 | 2 | 2 |
| 6 | 1 | 1 | 1 | 0 | 0 | 0 | 0 | 0 | 0 | 0 | 0 | 0 | 0 | 0 | 0 | 0 | 1 | 1 |
| 7 | 1 | 1 | — | 1 | 1 | 1 | 1 | 1 | — | — | — | 1 | 1 | 1 | 1 | 1 | 1 | — |
| 8 | 1 | 1 | 1 | 0 | 0 | 0 | 0 | 0 | 0 | 0 | 0 | 1 | 0 | 0 | 0 | 0 | 1 | 1 |
| 9 | 2 | — | — | 1 | 1 | 1 | 1 | — | — | — | — | 2 | 2 | 2 | 2 | 2 | 2 | 1 |
| 10 | 3 | 3 | 3 | — | — | — | — | — | — | — | — | — | — | — | — | — | 3 | 3 |
| 11 | 2 | — | — | 2 | 2 | 2 | 2 | 2 | — | — | — | 2 | 2 | 2 | 2 | 2 | 2 | 1 |
| 12 | 1 | 1 | — | 1 | 1 | 1 | — | — | — | — | — | — | — | — | 1 | 1 | 1 | 1 |
| 13 | 2 | — | — | — | — | — | — | — | — | — | — | — | — | — | — | — | — | — |
| 14 | 2 | 2 | 2 | — | — | — | — | — | — | — | — | — | — | — | — | — | 2 | 2 |
| 15 | 1 | — | — | — | — | — | — | — | — | — | — | — | — | — | 1 | 1 | 1 | — |
| 16 | 1 | — | — | 1 | 1 | 1 | 1 | 1 | — | — | — | 1 | 1 | 1 | 1 | 1 | 1 | 1 |
| 17 | 1 | — | — | 1 | 1 | 1 | — | 1 | — | — | — | 1 | 1 | 1 | 1 | 1 | 1 | 1 |
| 18 | 1 | 1 | 1 | — | — | — | — | — | — | — | — | — | — | — | — | — | 1 | 1 |
| untyped | 2 | 2 | 2 | — | — | — | — | — | — | — | — | — | — | — | — | — | 2 | 2 |
| | 27 | | | | | | | | | | | | | | | | | |
| *S. sonnei* | | | | | | | | | | | | | | | | | | |
| 1 | 64 | 64 | 64 | 64 | 64 | 64 | 64 | 64 | — | — | — | 33 | 33 | 33 | — | — | 64 | 64 |

TABLE 11

SUMMARY OF HYBRIDIZATION OF SHIGELLA SPECIFIC FRAGMENTS AND
OLIGONUCLEOTDIE CAPTURE/DETECTION PROBES TO SHIGELLA SEROTYPES
(++ SIGNAL USED AS CUT-OFF FOR DETECTABILITY).

| SEROTYPE | # TESTED | NT6 | 1911 1500 1501 | NT11-2 | 1682 1683 | 1708 1709 | NT18-1a | 1712 1713 | NT19-2 | 1684 1685 | ompA 1706 1707 | CR3 437c 1864 |
|---|---|---|---|---|---|---|---|---|---|---|---|---|
| *S. dysenteriae* | | | | | | | | | | | | |
| 1 | 8 | — | — | — | — | — | 6 | 6 | — | — | 8 | 7 |
| 2 | 2 | 1 | 1 | 2 | 2 | — | — | — | — | — | 2 | 2 |
| 3 | 3 | 3 | 3 | — | — | — | — | — | — | — | — | 3 |
| 4 | 3 | 3 | 3 | — | — | — | — | — | — | — | — | 3 |
| 5 | 1 | 1 | 1 | — | — | — | — | — | — | — | — | 1 |
| 6 | 1 | 1 | 1 | — | — | — | — | — | — | — | — | 1 |
| 7 | 1 | 1 | 1 | — | — | — | — | — | — | — | — | 1 |
| 8 | 1 | 1 | 1 | — | — | — | — | — | — | — | — | 1 |
| 9 | 3 | 3 | 3 | 2 | — | — | — | — | — | — | — | 3 |
| 10 | 1 | — | — | 1 | — | — | — | — | — | — | — | 1 |
| untyped | 1 | 1 | 1 | — | — | — | — | — | — | — | — | 1 |
| | 25 | | | | | | | | | | | |
| *S. flexneri* | | | | | | | | | | | | |
| 1 | 5 | — | — | — | — | — | 5 | 5 | 5 | 5 | — | 5 |
| 2 | 2 | — | — | — | — | — | 2 | 2 | 2 | 2 | — | 2 |
| 3 | 5 | 2 | 2 | 3 | — | 3 | 5 | 5 | 5 | 5 | — | 5 |
| 4 | 4 | — | — | — | — | — | 4 | 4 | 4 | 4 | — | 4 |
| 5 | 2 | 1 | 1 | — | — | — | 1 | 1 | 2 | 2 | — | 2 |
| 6 | 3 | 3 | 3 | — | — | — | — | — | — | — | — | 3 |
| untyped | 36 | 16 | 16 | 20 | — | 20 | 34 | 33 | 36 | 36 | — | 36 |
| | 57 | | | | | | | | | | | |
| *S. boydii* | | | | | | | | | | | | |
| 1 | 1 | 1 | 1 | — | — | — | — | — | — | — | — | 1 |
| 2 | 1 | 1 | 1 | — | ND | ND | — | ND | — | ND | ND | 1 |
| 3 | 1 | 1 | 1 | — | — | — | — | — | — | — | — | 1 |
| 4 | 1 | 1 | 1 | — | — | — | — | — | — | — | — | 1 |

TABLE 11-continued

SUMMARY OF HYBRIDIZATION OF SHIGELLA SPECIFIC FRAGMENTS AND OLIGONUCLEOTDIE CAPTURE/DETECTION PROBES TO SHIGELLA SEROTYPES (++ SIGNAL USED AS CUT-OFF FOR DETECTABILITY).

| SEROTYPE | # TESTED | NT6 | 1911 1500 1501 | NT11-2 | 1682 1683 | 1708 1709 | NT18-1a | 1712 1713 | NT19-2 | 1684 1685 | ompA 1706 1707 | CR3 437c 1864 |
|---|---|---|---|---|---|---|---|---|---|---|---|---|
| 5 | 2 | — | — | 2 | 2 | 2 | — | — | 2 | 2 | 2 | 2 |
| 6 | 1 | 1 | 1 | — | — | — | — | — | — | — | — | 1 |
| 7 | 1 | — | — | 1 | 1 | 1 | — | — | 1 | 1 | 1 | — |
| 8 | 1 | 1 | 1 | — | — | — | — | — | — | — | — | 1 |
| 9 | 2 | — | — | 1 | 1 | — | — | — | 2 | 2 | 2 | 1 |
| 10 | 3 | 3 | 3 | — | — | — | — | — | — | — | — | 3 |
| 11 | 2 | — | — | 2 | 2 | 2 | — | — | 2 | 2 | 2 | 1 |
| 12 | 1 | — | — | 1 | 1 | — | — | — | — | — | 1 | 1 |
| 13 | 2 | — | — | — | — | — | — | — | — | — | — | — |
| 14 | 2 | 2 | 2 | — | — | — | — | — | — | — | — | 2 |
| 14 | 2 | 2 | 2 | — | — | — | — | — | — | — | — | 2 |
| 15 | 1 | — | — | — | — | — | — | — | — | — | 1 | — |
| 16 | 1 | — | — | 1 | 1 | 1 | — | — | 1 | 1 | 1 | 1 |
| 17 | 1 | — | — | 1 | — | — | — | — | 1 | 1 | 1 | 1 |
| 18 | 1 | 1 | 1 | — | — | — | — | — | — | — | — | 1 |
| untyped | 2 | 2 | 2 | — | — | — | — | — | — | — | — | 2 |

S. sonnei

| | 27 | | | | | | | | | | | |
|---|---|---|---|---|---|---|---|---|---|---|---|---|
| 1 | 64 | 64 | 64 | 64 | 64 | 64 | — | — | 33 | 33 | — | 64 |

TABLE 12

SUMMARY OF INCLUSIVITY HYBRIDIZATION RESULTS OF SHIGELLA SPECIFIC FRAGMENTS AND CAPTURE/DETECTION OLIGONUCLEOTIDE PROBES INCLUDED IN PROBE SETS 1 AND 2 TO SHIGELLA SEROTYPES (++ SIGNAL USED AS CUT-OFF FOR DETECTABILITY). PROBE SET 1 INCLUDES OLIGONUCLEOTIDES 1911/1500/1501, 1684/1685 AND 1706/1707. PROBE SET 2 INCLUDES OLIGONUCLEOTIDES 1706/1707 AND 1864/437c.

| SEROTYPE | TESTED | NT6 | 1911 1500 1501 | NT19-2 | 1684 1685 | ompA 1706 1707 | CR3 437c 1864 | probe set I | probe set II |
|---|---|---|---|---|---|---|---|---|---|
| S. dysenteriae | | | | | | | | | |
| 1 | 8 | — | — | — | — | 8 | 7 | 8 | 8 |
| 2 | 2 | 1 | 1 | — | — | 2 | 2 | 2 | 2 |
| 3 | 3 | 3 | 3 | — | — | — | 3 | 3 | 3 |
| 4 | 3 | 3 | 3 | — | — | — | 3 | 3 | 3 |
| 5 | 1 | 1 | 1 | — | — | — | 1 | 1 | 1 |
| 6 | 1 | 1 | 1 | — | — | — | 1 | 1 | 1 |
| 7 | 1 | 1 | 1 | — | — | — | 1 | 1 | 1 |
| 8 | 1 | 1 | 1 | — | — | — | 1 | 1 | 1 |
| 9 | 3 | 3 | 3 | — | — | — | 3 | 3 | 3 |
| 10 | 1 | — | — | — | — | — | 1 | — | 1 |
| untyped | 1 | 1 | 1 | — | — | — | 1 | 1 | 1 |
| TOTAL | 25 | | | | | | | 24 | 25 |
| S. flexneri | | | | | | | | | |
| 1 | 5 | — | — | 5 | 5 | — | 5 | 5 | 5 |
| 2 | 2 | — | — | 2 | 2 | — | 2 | 2 | 2 |
| 3 | 5 | 2 | 2 | 5 | 5 | — | 5 | 5 | 5 |
| 4 | 4 | — | — | 4 | 4 | — | 4 | 4 | 4 |
| 5 | 2 | 1 | 1 | 2 | 2 | — | 2 | 2 | 2 |
| 6 | 3 | 3 | 3 | — | — | — | 3 | 3 | 3 |
| untyped | 36 | 16 | 16 | 36 | 36 | — | 36 | 36 | 36 |
| TOTAL | 57 | | | | | | | 57 | 57 |
| S. boydii | | | | | | | | | |
| 1 | 1 | 1 | 1 | — | — | — | 1 | 1 | 1 |
| 2 | 1 | 1 | 1 | — | ND | ND | 1 | 1 | 1 |
| 3 | 1 | 1 | 1 | — | — | — | 1 | 1 | 1 |
| 4 | 1 | 1 | 1 | — | — | — | 1 | 1 | 1 |
| 5 | 2 | — | — | 2 | 2 | 2 | 2 | 2 | 2 |

TABLE 12-continued

SUMMARY OF INCLUSIVITY HYBRIDIZATION RESULTS OF SHIGELLA SPECIFIC FRAGMENTS AND CAPTURE/DETECTION OLIGONUCLEOTIDE PROBES INCLUDED IN PROBE SETS 1 AND 2 TO SHIGELLA SEROTYPES (++ SIGNAL USED AS CUT-OFF FOR DETECTABILITY). PROBE SET 1 INCLUDES OLIGONUCLEOTIDES 1911/1500/1501, 1684/1685 AND 1706/1707. PROBE SET 2 INCLUDES OLIGONUCLEOTIDES 1706/1707 AND 1864/437c.

| SEROTYPE | TESTED | NT6 | 1911 1500 1501 | NT19-2 | 1684 1685 | ompA 1706 1707 | CR3 437c 1864 | probe set I | probe set II |
|---|---|---|---|---|---|---|---|---|---|
| 6 | 1 | 1 | 1 | — | — | — | 1 | 1 | 1 |
| 7 | 1 | — | — | 1 | 1 | 1 | — | 1 | 1 |
| 8 | 1 | 1 | 1 | — | — | — | 1 | 1 | 1 |
| 9 | 2 | — | — | 2 | 2 | 2 | 1 | 2 | 2 |
| 10 | 3 | 3 | 3 | — | — | — | 3 | 3 | 3 |
| 11 | 2 | — | — | 2 | 2 | 2 | 1 | 2 | 2 |
| 12 | 1 | — | — | — | — | 1 | 1 | 1 | 1 |
| 13 | 2 | — | — | — | — | — | — | — | — |
| 14 | 2 | 2 | 2 | — | — | — | 2 | 2 | 2 |
| 15 | 1 | — | — | — | — | 1 | — | 1 | 1 |
| 16 | 1 | — | — | 1 | 1 | 1 | 1 | 1 | 1 |
| 17 | 1 | — | — | 1 | 1 | 1 | 1 | 1 | 1 |
| 18 | 1 | 1 | 1 | — | — | — | 1 | 1 | 1 |
| untyped | 2 | 2 | 2 | — | — | — | 2 | 2 | 2 |
| TOTAL S. sonnei | 27 | | | | | | | 25 | 25 |
| 1 | 64 | 64 | 64 | 33 | 33 | — | 64 | 64 | 64 |

TABLE 13

SUMMARY OF HYBRIDIZATION RESULTS OF SHIGELLA PROBES, WHICH ARE INCLUDED IN PROBE SETS 1 AND 2, TO ENTEROINVASIVE E. COLI AND COMPETITOR ORGANISMS FOUND IN STOOL (+ SIGNAL USED AS CUT-OFF FOR DETECTABILITY).

| FRAGMENT (OLIGO-NUCLEOTIDES) | E. COLI (from Table 6) | | | OTHER ORGANISMS FOUND IN STOOL (from Tables 7, 8) | |
|---|---|---|---|---|---|
| | EIEC 5 | EVEC 43 | Non-EVEC 18 | Cyto-dot 91 | DNA-dot 91 |
| PROBE SET 1 | | | | | |
| NT6 (1500/1501/1911) | 5 | — | — | — | — |
| NT19-2 (1684/1685) | 1 | — | — | — | — |
| OMP A (1706/1707) | — | — | — | 2 | — |
| PROBE SET 2 | | | | | |
| OMP A (1706/1707) | — | — | — | 2 | — |
| Class 3R (1864/437c) | 3 | — | — | — | — |

Note:
EIEC - Enteroinvasive E. coli.

EVEC - Enterovirulent E. coli includes isolates of Enterotoxigenic E. coli, Enteropathogenic E. coli 0157 serotypes and non-0157 serotypes.
Non-EVEC - E. coli isolates not associated with disease. The two competitor organisms which are weakly detected by the ompA probes are both Escherichia fergusonii.

Equivalents

Those skilled in the art will recognize or be able to ascertain, using no more than routine experimentation, many equivalents to the specific embodiments of the invention described herein. Such equivalents are intended to be encompassed within the scope of this invention.

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
    ( A ) LENGTH: 164 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:1:

```
AATCCAACCG  CAGTAATAAA  CTGAATCCCT  CGCATGGCTT  GCAGCGCCTC  TACTACCGGA       60
TACAGCCTCC  ATTCGGTAAC  NGCCTCCTTC  AGGGCGGATT  CCAGCCGTTC  ACATTGTGCC      120
TGCCGATCTT  CTATTGTACG  ACGGTGTTCG  TCAAAAGCTA  ATTG                        164
```

( 2 ) INFORMATION FOR SEQ ID NO:2:

( i ) SEQUENCE CHARACTERISTICS:
        ( A ) LENGTH: 796 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CATCAGAAAT  CTAAGCAGAA  GTCTTTCCGT  GTTTCTCAGA  AATGGGGGCA  ACGTGCAAAA       60
CTTGCCCTTG  CTGGTGAACA  ACGTCTTACA  AAGATGGTTC  CTGGATGGAT  TGACCCTGAG      120
ACTTTTAAAC  TCAATGAACA  CGCTGAGACT  GTGAGATTGA  TATTCAAACT  GCTGCTAGAT      180
GGTGAAAGTC  TGCATAACAT  TGCACGTCAC  CTTCAAAGCA  ACGGTATAAA  GTCGTTTAGT      240
CGCCGTAAAG  ATGCTAATGG  GTTCTCTGTT  CACTCTGTAC  GCACATTCTA  AGGTCAGAGC      300
AACAATAGGC  ACGTTACCAG  CATCACAACG  TAATGACCGC  CCCGCTATAC  CGAACTACTA      360
CGAAGGTGTT  GTAGATATAC  CAACGTTCAA  TAAAGCTCAA  GAGATTCTCG  ACAAGAATCG      420
TAAAGGCCGT  ACACCTGCAA  GTGACAACCC  ACTAACGATT  AACATCTTCA  AAGGTCTGTT      480
TAGGTGTCAG  TGTGGGGCTA  GTGTCCATCC  TACCGGAACA  AAGAATAAGT  ATGCTGGGGT      540
CTACAGGTGC  AATAACCACT  TAGACGGTCG  CTGTGATGTT  CCACCGTTGA  AGCGTAAACC      600
GTTTGACCGA  TGGATGATTG  ATAATTTTCT  GGGGATGATT  GACGTGGGGA  ATGATGGAGA      660
ATCAGAGAGA  AAGATTGCAG  CGTTACAGCA  TGAGGTTGAA  ATTGTCACAG  CCAGAATCAA      720
GAAACGTACC  GCCCTACTTC  TTGAGATGGA  TGATATTGAT  GAACTAAAAA  TTCAGCTTAA      780
GGAACTGAAC  CAGAAG                                                         796
```

( 2 ) INFORMATION FOR SEQ ID NO:3:

( i ) SEQUENCE CHARACTERISTICS:
        ( A ) LENGTH: 587 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GATCTTTCTT  CGAAGAAGAG  AGCGCACCAA  TACCCGCGCC  CACGAGAGAG  CCCAGACCTG       60
CGCCGATAGC  AGATTTGCCT  GCTTCGCGTT  CGCCGGTGTA  AGGGTTAGTT  GTGCAGCCAG      120
ATACCGCCAG  AGCGCCACTC  ACTACGGAGG  CAATAAGATA  AACACGTTTG  TTCATTGTTA      180
ATCCTTCCTA  ACCTTTTTAT  TCTTTGCCAC  GGGTTCCGTG  GCGGGAGATT  ATGCCGCGTG      240
AACATGAAGA  TGAGGTGTAC  TGGCAATAGC  GGACACTACC  ATTTGTTCTT  TTTTAAGCA      300
GCCATCTGAT  GATATTTTTC  CCTGAAGGCT  GCCGGGGAGA  TATTCCCCAG  ACGAGAGTGA      360
CGACGCTGAC  GATTCTAGAA  AATCTCAATG  TATTCCCGTA  TTACTGAGAT  GGCTTCATCC      420
CGGTTATTAA  AACGATAGTG  GCTCAGGCTC  TCATTTTTCA  GCGTTCCCCA  CAAGCTTTCC      480
```

| | | | | | |
|---|---|---|---|---|---|
| ATCGGAGCGT | TGTCGTAACA | GTTACCTTTA | CGCGACATTG | ATGTTTTCAG | ACCAGACTGC | 540 |
| TCCTGTATGA | CCCGGTAATC | GTATGCGCAG | TACTGTGAAC | CTCGATC | | 587 |

( 2 ) INFORMATION FOR SEQ ID NO:4:

( i ) SEQUENCE CHARACTERISTICS:
        ( A ) LENGTH: 786 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

| | | | | | |
|---|---|---|---|---|---|
| GATCAGAGTG | GTGGATTAGC | CCGGCAGTGG | GCGCTGGCTC | CTGAGCGCCA | TAAACAGGGC | 60 |
| TTTACCTGTC | AGCTCTTTTG | TCATGCGCTC | TCCCATGGCG | TACGACAATT | TCGCACGTAT | 120 |
| AAACATCTTT | GATGCCAGCG | AGGTACAACC | ATCCCTCCTG | TGTGGCAACA | TACGTCAGGT | 180 |
| CCGCCACCCA | GACCTGATTT | GGTGCTGTAG | GAGCGAACGT | CTGGTTCAGC | AGATTGGCG | 240 |
| CAACTGGCAG | ATTGTGGTTC | GAGTTCGTAG | TCGCTCTGAA | CTTGCGTTCT | GCTTACAGCG | 300 |
| TAGCTTAGCT | CCTTACGAAG | ACGTGCCAGT | CGGTCACGAC | CAACGATGAT | GCCATTCTCT | 360 |
| GCCAGCTCCG | TCTGGAGCC | GCCGGGTTTC | CATATGTTTC | GCGAGTGCGG | ATATGTGCCA | 420 |
| CCTTAATCTC | CAGTTTTAGC | CGCTCATCAC | TTTGTTTTCT | GTCTGAGGGT | TCATGCTGTA | 480 |
| CCCAGTTGTA | ATAACCGCTC | CTGGATACAC | CAAATACTGA | CACATCGCTT | CAATGGGAAA | 540 |
| TTGTTGTCGC | CATTGTTCGA | TTAACGCGTA | TTTTCAGCG | ACTCCTGTGC | AAAATACGCT | 600 |
| GTTGCTTTTT | TTAATATATC | TCGCTCAAGG | CGAGCTTCAT | TTAACGCCTT | ACGCAGTCGC | 660 |
| AGAATTTCAG | ATTCCAGTTC | AGCCACCGTG | CGGGAACCAG | GAGTACCGAG | CCCTTTTCTG | 720 |
| GCGGCGGTAA | CCCATTGTCC | TAAAGTGCCT | TCAGGAAGAG | ATAATCGGGA | AGCGCCTTCA | 780 |
| CTGATC | | | | | | 786 |

( 2 ) INFORMATION FOR SEQ ID NO:5:

( i ) SEQUENCE CHARACTERISTICS:
        ( A ) LENGTH: 1174 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

| | | | | | |
|---|---|---|---|---|---|
| AGTTGGACTA | TAGGTGTACT | GGCAATACGG | ACACACCATT | TGTTCTTTTT | TTAAGCAGCA | 60 |
| TCTGATGATA | TTTTTCCCTG | AAGGCTGCCG | GGGAGATATT | CCCCAGACGA | GAGTGACGAC | 120 |
| GCTGACGATT | GTAGAAAATC | TCAATGTATT | CCCGTATTAC | TGAGATGGCT | TCATCCCGGT | 180 |
| TATTAAAACG | ATAGTGGCTC | AGGCTCTHAT | TTTTCAGCGT | TCCCCANAAG | CTTTCCATCG | 240 |
| GAGCGTTGTC | GTAACAGTTA | CCTTTACGCG | ACATTGATGT | TTTCAGACCA | AACTGCTCCT | 300 |
| GTATGACCCG | GTAATCGTAT | GCGCAGTACT | GTGAACCTCG | ATCAGAGTGG | TGGATTAGCC | 360 |
| CGGCAGGNGG | GCGCTGGCTC | CTGAGCGCCA | TAAACAGGGC | TTTACCTGTC | AGCTCTTTTG | 420 |
| TCATGCGCTC | TCCCATGCGT | AGCCGACAAT | TCGCACGTA | TAACATCTTT | GATGCCAGCG | 480 |
| AGGTACACCA | TCCCTCCTGT | GTGGCANCAT | ACGTCAGGTC | CGCCACCCAG | ACCTGATTTG | 540 |
| GTGCTGTAGG | AGTGAACGTC | TGGTTCAGCA | GATTGGCGC | AACTGGCAGA | TTGTGGTTCG | 600 |
| GGTTCGTAGT | CGCTCTGAAC | TTGCGTTTCT | GCTTACAGCG | TASCTTAGCT | CCTTACGAAG | 660 |
| ACGTGCCAGT | CGGTCACGCC | AACGATGATG | CCATTCTCTG | CCAGCTCCGT | CTGGAGCCGC | 720 |
| CGGGTTCCAT | ATGTTDCGCR | AGTGCGGATA | TGTGCCACCT | TAATCTCCAG | TTTDAGCCGC | 780 |

| | | | | | |
|---|---|---|---|---|---|
| TCATCACTTT | GTTDTCTGTC | TGAGGGTTCA | TGCTGTACCC | AGTTGTAATA | ACCGCTCCTG | 840
| GATACACCAA | ATACCTGACA | CATCGCTTSA | ATDDDAAATT | GTTGTCGCCA | TTGTTCGATT | 900
| AACGCGNNNN | NNNCAGCGAC | TCCTGTGCAA | AATACGCTGT | TGCTTTTTTT | AATATATCTC | 960
| GCTCAAGGCG | AGCTTCATTT | AACGCTTTAC | GCAGTTGCAG | AATTTCAGAT | TCCAGTTCAG | 1020
| CCACCGTGCG | GGAACCAGGA | GTACCGAGCC | CTTTTCTGGC | GGCGGTAACC | CATTGTCCTA | 1080
| AAGTGCCTTC | AGGAAGAGAT | AATCGGGAAG | CGCCTTCGCT | GATCGAAAGT | TGATTTTCAA | 1140
| GAACCGTTCT | GACAGCTTCG | GCTTTGAACT | CTGT | | | 1174

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: double
        (D) TOPOLOGY: linear (xi) SEQUENCE DESCRIPTION: SEQ ID NO:6:

| | | | | | |
|---|---|---|---|---|---|
| TGTGGCATCA | ACAATGGTGC | GACCACCGAG | CGAGATGAGG | TGTACTGGCA | ATAGCGGACA | 60
| CAAC | | | | | | 64

(2) INFORMATION FOR SEQ ID NO:7:

(i) SEQUENCE CHARACTERISTICS:
        (A) LENGTH: 1196 base pairs
        (B) TYPE: nucleic acid
        (C) STRANDEDNESS: double
        (D) TOPOLOGY: linear (xi) SEQUENCE DESCRIPTION: SEQ ID NO:7:

| | | | | | |
|---|---|---|---|---|---|
| ATTGTAGAAA | ATCTCAATGT | ATTCCCGTAT | TACTGAGATG | GCTTCATCCC | GGTTATTAAA | 60
| ACGATAGTGG | CTCAGGCTCT | HATTTTCAG | CGTTCCCCAN | AAGCTTTCCA | TCGGAGCGTT | 120
| GTCGTAACAG | TTACCTTTAC | GCGACATTGA | TGTTTCAGA | CCAAACTGCT | CCTGTATGAC | 180
| CCGGTAATCG | TATGCGCAGT | ACTGTGAACC | TCGATCAGAG | TGGTGGATTA | GCCCGGCAGG | 240
| NGGGCGCTGG | CTCCTGAGCG | CCATAAACAG | GGCTTTACCT | GTCAGCTCTT | TTGTCATGCG | 300
| CTCTCCCATG | CGTAGCCGAC | AATTTCGCAC | GTATAACATC | TTTGATGCCA | GCGAGGTACA | 360
| CCATCCCTCC | TGTGTGGCAN | CATACGTCAG | GTCCGCCACC | CAGACCTGAT | TTGGTGCTGT | 420
| AGGAGTGAAC | GTCTGGTTCA | GCAGATTTGG | CGCAACTGGC | AGATTGTGGT | TCGGGTTCGT | 480
| AGTCGCTCTG | AACTTGCGTT | TCTGCTTACA | GCGTASCTTA | GCTCCTTACG | AAGACGTGCC | 540
| AGTCGGTCAC | GCCAACGATG | ATGCCATTCT | CTGCCAGCTC | CGTCTGGAGC | CGCCGGGTTC | 600
| CATATGTTDN | GCRAGTGCGG | ATATGTGCCA | CCTTAATCTC | CAGTTDAGC | CGCTCATCAC | 660
| TTTGTTDTCT | GTCTGAGGGT | TCATGCTGTA | CCCAGTTGTA | ATAACCGCTC | CTGGATACAC | 720
| CAAATACCTG | ACACATCGCT | TNAATGGGAA | ATTGTTGTCG | CCATTGTTCG | ATTAACGCGN | 780
| ATTTTCAGC | GACTCCTGTG | CAAAATACGC | TGTTGCTTTT | TTNATATAT | CTCGCTCAAG | 840
| GCGAGCTTCA | TTTAACGCCT | TACGCAGTTG | CAGAATTTCA | GATTCCAGTT | CAGCCACCGT | 900
| GCGGGAACCA | GGAGTACCGA | GCCCTTTTCT | GGCGGCGGTA | ACCCATTGTC | CTAAAGTGCC | 960
| TTCAGGAAGA | GNTAATCGGG | AAGCGCCTTC | GCTGATCGAA | AGTTGATTTT | CAAGAACCGT | 1020
| TCTGACAGCT | TCGGCTTTGA | ACTCTTTAGA | GTAACGTTGG | TTTTTCTGC | TCATTATTAG | 1080
| CTCCTTCTGA | TGCCATTCTA | TTTCAGGAAG | GAGTGTCCGT | TAAACTCAGG | CTACCTCAAG | 1140
| ATAAAGTTAT | TAATTTCGAA | GATCACATCT | TCAATAGGTT | TGCGGTCCAT | ATTATC | 1196

( 2 ) INFORMATION FOR SEQ ID NO:8:

( i ) SEQUENCE CHARACTERISTICS:
        ( A ) LENGTH: 64 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

```
AAAGCACAGA TTTTATAGCT AACTCGATGC TGGTGTGAGG TGTACTGGCA ATAGCGGACA        60
CTAC                                                                    64
```

( 2 ) INFORMATION FOR SEQ ID NO:9:

( i ) SEQUENCE CHARACTERISTICS:
        ( A ) LENGTH: 1188 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

```
ATTGTAGAAA ATCTCAATGT ATTCCCGTAT TACTGAGATG GCTTCATCCC GGTTATTAAA        60
ACGATAGTGG CTCAGGCTCT HATTTTTCAG CGTTCCCCAN AAGCTTTCCA TCGGAGCGTT       120
GTCGTAACAG TTACCTTTAC GCGACATTRA TGTTTTCAGA CCAGACTRCT CCTGTATGAC       180
CCGGTAATCG TATGCGCAGT ACTGTGAACC TCGATCAGAG TGGTGGATTA GCCCGGCAGG       240
NGGGCGCTGG CTCCTGAGCG CCATAAACAG GGCAAATCCT GTCAGCTCTW TTGTCATGCG       300
CTCTCCCATG CGTAGCCGAC TAATTTCGCA CGTATAACAT CTTTGATGCC AGCGAGGTAC       360
ACCATCCCTC CTGTGTGGCA NCATACGTCA GGTCCGCCAC CCAGACCTGA TTTGGTGCTG       420
TAGGAGCGAA CGTCTGGTTC AGCAGATTTG GCGCAACTGG CAGATTGTGG TTCGAGTTCG       480
TAGTCGCTCT GAACTTGCGT TTCTGCTTAC AGTGTAGCCT TAGCTCCTTA CGAAGACGTG       540
CCAGTCGGTC ACGCCAACGA TGATGCCATT CTCTGCCAGC TCCGTCTGGA GCCGCGGGT       600
TCCATATGTT NCGCRAGTGC GGATATGTGC CACCTTAATC TCCAGTTTDA GCCGCTCATC       660
ACTTTGTTDT CTGTCTGAGG GTTCATGCTG TACCCAGTTG TAATAACCGC TCCTGGATAC       720
ACCAAATACC TGACACATCG CTTSAATGGG AAATTGTTRT CGCCATTGTT CGATTAACGC       780
GACTCCTGTG CAAAATACGC TGTTGCTTTT TTNNATATAT CTCGCTCAAG GCGAGCTTCA       840
TTTAACGCCT TACGCAGTTG CAGAATTTCA GATTCCAGTT CAGCCACCGT GCGGGAACCA       900
GGAGTACCGA GCCCTTTTCT GGCGGCGGTA ACCCATTGTC CTAAAGTGCC TTCAGGAAGA       960
GATAATCGGG AAGCGCCTTC ACTGATCGAA AGTTGATTTT CAGGAACCGT TCTGACAGCT      1020
TCGGCTTTGA ACTCTTKAGA GTAACGTTGG GTTTTTCTGC TCATTATTAG CTCCTTCTGA      1080
TGCCATTCTA TTTCAGGAAG GAGTGTCCGT TAAACTCAGG CTACCTCAGT GTGATCGGCG      1140
ATAAGCCCAG AACTCCGCTC CCAGACCTCC CTGCCAAAAG CAAAACCG                   1188
```

( 2 ) INFORMATION FOR SEQ ID NO:10:

( i ) SEQUENCE CHARACTERISTICS:
        ( A ) LENGTH: 630 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

```
ATCTCCTTAT GTTATGGAGA TTATTAAAAA GAATAACATT AGCGCTCTCG AACTGCATCG        60
TGCAATTGTT GAGTTGAGTA AAAATATGAA GTCGATTGAT GATAATGCCA GTAAGAAAAA       120
```

| | | | | | |
|---|---|---|---|---|---|
| CGACAAGTCA | TCATTGTATG | TATCATGGAC | TCTGAGTTTT | ACTGCTCCAA | CAAGTAAAGA | 180 |
| AGCTCACGAT | GTGTTGTCTG | GGTATATTAA | TTATGTTTCT | TCCCTTGTTG | TAAGGGATTT | 240 |
| GATGGAAGAT | ATAAGAAATA | AACTAGAAGT | TAAAACTAAT | GTTGAAAAAG | AAATTCTTGC | 300 |
| ACTGGATGAG | ATAAAAATTA | GAAACCAGCT | GAATGCAGAT | ATTCGACNCC | TCAATTATTC | 360 |
| ACTGGAGGTT | GCTAATGCGG | CTGGAATAAA | AAAACCTGTA | TACAGCAATG | GTCAGATTAT | 420 |
| GAAGGATGAC | CCAGATTTTC | CTGTGGCTCT | CGGTTCTGAT | GGTATAGCAA | CTAAATTGAA | 480 |
| CATCAAAAAA | TCAATCAAGG | ATGTTTCGGA | ATTGAGTGGG | GAGTTGCGAA | ATCGTCAATA | 540 |
| TGTTGTGAAT | CAATTGGTTG | TGGCGAAAGN | GGGGGANGNN | GANNNNANGC | MANNNCAGNA | 600 |
| NCAANNGTGC | CCAACGNNAC | CGGNCAGAAA | | | | 630 |

( 2 ) INFORMATION FOR SEQ ID NO:11:

( i ) SEQUENCE CHARACTERISTICS:
        ( A ) LENGTH: 388 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:11:

| | | | | | |
|---|---|---|---|---|---|
| CCACCACATT | GATTGTCTGC | CTGAAATAAC | ACGAAAGGCA | CTGCGTGAAC | GCTATGTGGA | 60 |
| ACAGCTGGTG | GCTACAGAGA | ACAATGTTTC | TGAAGTGAAA | GCTGTTACCA | GAAAAACACG | 120 |
| CAATCCTGAC | GCTGTCCAGG | CAATCGAAGC | ATATCGCGGT | TCTCCACAAC | TGATGGAAGA | 180 |
| ACGCCTGAAT | GCGCTGACCG | AAAACCAGCG | CTGGGTATCT | GAAGCAAGAG | CTGCGCTGGT | 240 |
| GGTGGAAGTG | CTGAAGCTGG | AAAGCGCCGG | TAACCCCGGG | CGACTGAAAG | CCATTAACTT | 300 |
| TCTTGTTGAA | AAAGCCCCTA | AGGTGAGCT | GCCGGAGCGC | CTGCAACAGG | CCGCAGTTAA | 360 |
| CGCCAATGCA | AAACGTGGCG | CTAATCGT | | | | 388 |

( 2 ) INFORMATION FOR SEQ ID NO:12:

( i ) SEQUENCE CHARACTERISTICS:
        ( A ) LENGTH: 184 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:12:

| | | | | | |
|---|---|---|---|---|---|
| CTGACGACCT | GGACGTGTAC | ACTCGTCTGG | GTGGTATGGT | TTGGCGTGCA | GACACCAAAG | 60 |
| CTCACAACAA | TGTGACAGGT | GAATCTGAGA | AAAACCACGA | TACCGGCGTT | TCTCCGGTAT | 120 |
| TCGCAGGTGG | TGTTGAATGG | GCCATCACTC | CTGAAATCGC | TACCCGTCTG | GAATACCAGT | 180 |
| GGAC | | | | | | 184 |

( 2 ) INFORMATION FOR SEQ ID NO:13:

( i ) SEQUENCE CHARACTERISTICS:
        ( A ) LENGTH: 169 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:13:

| | | | | | |
|---|---|---|---|---|---|
| CTGACGACCT | GGACATCTAC | ACTCGTCTGG | GTGGCATGGT | ATGGCGTGCA | GACACTAAAT | 60 |
| CCAACGTTTA | TGGTAAAAAC | CACGACACCG | GCGTTTCTCC | GGTCTTCGCT | GGCGGTGTTG | 120 |
| AGTACGCGAT | CACTCCTGAA | ATCGCTACCC | GTCTGGAATA | CCAGTGGAC | | 169 |

5,648,481

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TTGCAGCGCC TCTACTACCG GATACAGCCT CCATT     35

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCTCCTTCAG GGCGGATTCC AGCCGTTCAC ATTGT     35

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCGATCTTCT ATTGTACGAC GGTGTTCGTC AAAAGCTAAT     40

( 2 ) INFORMATION FOR SEQ ID NO:17:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CTGGTGAACA ACGTCTTACA AAGATGGTTC CTGGATGGAT T     41

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AGTCTTTCCG TGTTTCTCAG AAATGGGGGC AACGTGCAAA A     41

( 2 ) INFORMATION FOR SEQ ID NO:19:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CCACCGTTGA AGCGTAAACC GTTTGACCGA TGGAT     35

( 2 ) INFORMATION FOR SEQ ID NO:20:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:20:

GCTGGGGTCT ACAGGTGCAA TAACCACTTA GACGGT    36

( 2 ) INFORMATION FOR SEQ ID NO:21:

( i ) SEQUENCE CHARACTERISTICS:
  ( A ) LENGTH: 48 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:21:

CGATGATGCC ATTCTCTGCC AGCTCCGTCT GGGAGCCGCC GGGTTTCC    48

( 2 ) INFORMATION FOR SEQ ID NO:22:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:22:

GGAGCAGTCT GGTCTGA    17

( 2 ) INFORMATION FOR SEQ ID NO:23:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:23:

CCTGTGGCTC TCGGTTCTGA TGGTATAGCA ACTAAAT    37

( 2 ) INFORMATION FOR SEQ ID NO:24:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:24:

CAAGGATGTT TCGGAATTGA GTGGGGAGTT GCGAAAT    37

( 2 ) INFORMATION FOR SEQ ID NO:25:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:25:

CAGGCAATCG AAGCATATCG CGGTTCTCCA CAACT    35

( 2 ) INFORMATION FOR SEQ ID NO:26:

( i ) SEQUENCE CHARACTERISTICS:

```
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

TGAATGCGCT  GACCGAAAAC  CAGCGCTGGG  TATCT                                    35

( 2 ) INFORMATION FOR SEQ ID NO:27:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GTGATGGCCC  ATTCAACACC  ACCTGCGAAT  ACCGG                                    35

( 2 ) INFORMATION FOR SEQ ID NO:28:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CTCAGATTCA  CCTGTCACAT  TGTTGTGAGC  TTTGG                                    35

( 2 ) INFORMATION FOR SEQ ID NO:29:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AATCCATCCA  GGAACCATCT  TTGTAAGACG  TTGTTCACCA  G                            41

( 2 ) INFORMATION FOR SEQ ID NO:30:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

TTTTGCACGT  TGCCCCCATT  TCTGAGAAAC  ACGGAAAGAC  T                            41
```

We claim:

1. A Shigella specific nucleic acid fragment wherein the fragment is selected from the group consisting of:
   a) NT-6 (nucleotides 1–124 of SEQ ID NO: 1);
   b) NT11-2 (SEQ ID NO: 2); and
   c) RNA fragments having the sequence of a) or b), wherein U is substituted for T.

2. A Shigella specific nucleic acid fragment, wherein the fragment is selected from the group consisting of:
   a) NT18-1a (SEQ ID NO: 10);
   b) NT19-2 (SEQ ID NO: 11); and
   c) RNA fragments having the sequence of a) or b), wherein U is substituted for T.

3. A nucleic acid probe for the detection of a member of the genus Shigelia wherein the probe detects at least one untyped isolate or at least one isolate of a serotype of each of the four species of the genus Shigelia and wherein the nucleotide sequence of the probe consists of a specific sequence element, optionally incorporated into a larger non-Shigella sequence for assay purposes, wherein said specific sequence element is selected from the group consisting of:
   a) SEQ ID NO: 1;
   b) fragments of SEQ ID NO: 1, which are identical over their length to a portion of SEQ ID NO: 1 or are complementary over their length to a portion of a selected strand of SEQ ID NO: 1 and wherein the fragments specifically hybridize to nucleic acid from members of the genus of Shigella and/or enteroinvasive E. coli;

c) NT11-2 (SEQ ID NO: 2);

d) fragments of NT11-2, which are identical over their length to a portion of NT11-2 or are complementary over their length to a portion of a selected strand of NT11-2 and wherein the fragments specifically hybridize to nucleic acid from members of the genus of Shigella and/or enteroinvasive E. coli; and e) an RNA sequence having the sequence of any one of a) through d), wherein U is substituted for T.

4. A nucleic acid probe of claim 3 for the detection of a member of the genus Shigella wherein said specific sequence element is selected from the group consisting of:

a) 1500 (SEQ ID NO: 14), 5'-TTGCAGCGCC-TCTACTACCGGATACAGCCTCCATT-3';

b) 1501 (SEQ ID NO: 15), 5'-CCTCCTTCAGGGC-GGATTCCAGCCGTTCACATTGT-3';

c) 1911 (SEQ ID NO: 16), 5'-CCGATCTTCTATTGT-ACGACGGTGTTCGTCAAAAGCTAAT-3';

d) 1682 (SEQ ID NO: 17), 5'-CTGGTGAACAACGTC-TTACAAAGATGGTTCCTGGATGGATT-3';

e) 1683 (SEQ ID NO: 18), 5'-AGTCTTTCCGTG-TTTCTCAGAAATGGGGGCAACGTGCAAAA-3';

f) 1708 (SEQ ID NO: 19), 5-CCACCGTTGAAGCG-TAAACCGTTTGACCGATGGAT-3';

g) an RNA sequence having the sequence of any one of a) through f), wherein U is substituted for T; and h) exact complements of any one of a) through g).

5. A nucleic acid probe wherein the probe detects at least one isolate of each of serotypes 1–5 of Shigella flexneri and the nucleotide sequence of the probe consists of a specific sequence element, optionally incorporated into a larger non-Shigella sequence for assay purposes, wherein said specific sequence element is selected from the group consisting of:

a) NT18-1a (SEQ ID NO: 10);

b) fragments of NT18-1a, which are identical over their length to a portion of NT18-1a or are complementary over their length to a portion of a selected strand of NT18-1a and wherein the fragments specifically hybridize to nucleic acid from Shigella;

c) an RNA sequence having the sequence of a) or b), wherein U is substituted for T;

d) NT19-2 (SEQ ID NO: 11);

e) fragments of NT19-2, which are identical over their length to a portion of NT19-2 or are complementary over their length to a portion of a selected strand of NT19-2 and wherein the fragments specifically hybridize to nucleic acid from Shigella and/or enteroinvasive E. coli; and f) an RNA sequence having the sequence of d) or e), wherein U is substituted for T.

6. A nucleic acid probe of claim 5 wherein said specific sequence element is selected from the group consisting of:

a) 1712 (SEQ ID NO: 23), 5'-CCTGTGGCTCTCGG-TTCTGATGGTATAGCAACTAAAT-3';

b) 1713 (SEQ ID NO: 24), 5'-CAAGGATGTTT-CGGAATTGAGTGGGGAGTTGCGAAAT-3';

c) an RNA sequence having the sequence of a) or b), wherein U is substituted for T; and d) exact complements of any one of a) through c).

7. A nucleic acid probe of claim 5 d) through f) which further detects a member of the genus Shigella selected from the group consisting of Shigella boydii serotype 5, Shigella boydii serotype 7, Shigella boydii serotype 9, Shigelia boydii serotype 11, Shigella boydii serotype 16, Shigella boydii serotype 17, and Shigella sonnei serotype 1.

8. A nucleic acid probe of claim 7 wherein said specific sequence element is selected from the group consisting of:

a) 1684 (SEQ ID NO: 25), 5'-CAGGCAATCGAAG-CATATCGCGGTTCTCCACAACT-3';

b) 1685 (SEQ ID NO: 26), 5'-TGAATGCGCTGA-CCGAAAACCAGCGCTGGGTATCT-3' c) an RNA having the sequence of a) or b), wherein U is substituted for T; and d) exact complements of any one of a) through c).

9. A nucleic acid probe for the detection of at least one isolate of Shigella selected from the group consisting of Shigella dysenteriae serotypes 1 and 2, and Shigella boydii serotypes 5, 7, 9, 11, 12, 15, 16, and 17, wherein the nucleotide sequence of the probe consists of a specific sequence element, optionally incorporated into a larger non-Shigella sequence for assay purposes, wherein said specific sequence element is selected from the group consisting of:

a) 1707 (SEQ ID NO: 28), 5'-CTCAGATTCACC-TGTCACATTGTTGTGAGCTTTGG-3';

b) 1706 (SEQ ID NO: 27), 5'-GTGATGGCCCATT-CAACACCACCTGCGAATACCGG-3';

c) an RNA sequence having the sequence of a) or b), wherein U is substituted for T; and d) exact complements of any one of a) through c).

10. A substantially inclusive nucleic acid probe for the detection of a member of the genus Shigella, the nucleotide sequence of the probe consisting of a specific sequence element, optionally incorporated into a larger non-Shigella sequence for assay purposes, wherein said specific sequence element is selected from the group consisting of:

a) 437 (SEQ ID NO: 21), 5'-CGATGATGCCATTCTCTGCCA-GCTCCGTCTGGGAGCCGCCGGGTTTCC-3';

b) 1864 (SEQ ID NO: 22), 5'-GGAGCAGTCTGGTCTGA-3';

c) an RNA sequence having the sequence of any one of a) or b), wherein U is substituted for T; and d) exact complements of a) through c).

11. A substantially inclusive nucleic acid capture/detector probe pair for the detection of a member of the genus Shigella, comprising a substantially inclusive tailed capture probe and a detector probe wherein the nucleotide sequence of the tailed capture probe consists of a first specific sequence element and a polynucleotide tail, wherein the first specific sequence element is selected from the group consisting of:

a) 1864 (SEQ ID NO: 22);

b) an RNA molecule having the sequence of a), wherein U is substituted for T; and c) exact complements of a) or b);

and wherein the first specific sequence element is complementary to a selected strand of Shigella DNA consisting of NT14 (SEQ ID NO: 4) and NT15 (SEQ ID NO: 3), and the nucleotide sequence of the detector probe consists of a second specific sequence element, optionally incorporated into a larger non-Shigella sequence for assay purposes, wherein said second specific sequence element is a fragment of a strand of Shigella sonnei DNA which comprises NT14 and NT15 and which is complementary to the selected strand, and wherein the fragment specifically hybridizes to nucleic acid from members of the genus Shigella and/or enteroinvasive *E. coli*.

12. A substantially inclusive capture/detector probe pair of claim 11, the probe pair also being exclusive of exclusivity organisms commonly found in stool and substantially exclusive of non-enteroinvasive *Escherichia coli* Enterobacteriaceae.

13. A substantially inclusive nucleic acid probe set for the detection of a member of the genus Shigella, which further detects enteroinvasive *Escherichia coli*, comprising at least three capture/detector probe pairs, each probe having a nucleotide sequence consisting of a specific sequence element, optionally incorporated into a larger non-Shigella sequence for assay purposes, wherein:
   a) each of a first pair of probes has a specific sequence element which is independently selected from the group consisting of:
      i) a fragment of a selected strand of SEQ ID NO: 1, which specifically hybridizes to nucleic acid from Shigella and/or enteroinvasive *E. coli*, and,
      ii) an RNA analog thereof wherein U is substituted for T throughout;
   b) each of a second pair of probes has a specific sequence element which is independently selected from the group consisting of:
      i) a fragment of a selected strand of fragment NT19-2 (SEQ ID NO: 11), which specifically hybridizes to nucleic acid from Shigella and/or enteroinvasive *E. coli*, and,
      ii) an RNA analog thereof wherein U is substituted for T throughout; and
   c) each of a third pair of probes has a specific sequence element which is independently selected from the group consisting of:
      i) a fragment of a selected strand of a double-stranded nucleic acid having the sequence SEQ ID NO: 12, which specifically hybridizes to nucleic acid from Shigella, and,
      ii) an RNA analog thereof wherein U is substituted for T throughout.

14. A substantially inclusive probe set of claim 13, comprising at least three capture/detector probe pairs, wherein:
   a) each of the first pair of probes has a specific sequence element which is a fragment of a selected strand of SEQ ID NO: 1 or an RNA analog thereof wherein U is substituted for T throughout, and which specifically hybridizes to nucleic acid from Shigella and/or enteroinvasive *E. coli*,
   b) each of the second pair of probes has a specific sequence element which is a fragment of a selected strand of fragment NT19-2 (SEQ ID NO: 11) or an RNA analog thereof wherein U is substituted for T throughout, and which specifically hybridizes to nucleic acid from Shigella and/or enteroinvasive *E. coli*, and
   c) each of the third pair of probes has a specific sequence element which is a fragment of a selected strand of a double-stranded nucleic acid having the sequence SEQ ID NO: 12 or an RNA analog thereof wherein U is substituted for T throughout, and which specifically hybridizes to nucleic acid from Shigella.

15. A substantially inclusive probe set of claim 14, the probe set also being exclusive of exclusivity organisms commonly found in stool and substantially exclusive of non-enteroinvasive *Escherichia coli* Enterobacteriaceae.

16. A substantially inclusive nucleic acid probe set for the detection of a member of the genus Shigella, which further detects enteroinvasive *Escherichia coli*, comprising at least three capture/detector probe pairs, each probe having a nucleotide sequence consisting of a specific sequence element, optionally incorporated into a larger non-Shigella sequence for assay purposes, wherein:
   each of a first pair of probes has a specific sequence element which is independently selected from the group consisting of:
      a) 1911 (SEQ ID NO: 16);
      b) 1500 (SEQ ID NO: 14);
      c) 1501 (SEQ ID NO: 15); and
      d) RNA analogs thereof wherein U is substituted for T throughout,
   each of a second pair of probes has a specific sequence element which is independently selected from the group consisting of:
      a) 1684 (SEQ ID NO: 25);
      b) 1685 (SEQ ID NO: 26); and
      c) RNA analogs thereof wherein U is substituted for T throughout, and
   each of a third pair of probes has a specific sequence element which is independently selected from the group consisting of:
      a) 1706 (SEQ ID NO: 27);
      b) 1707 (SEQ ID NO: 28); and
      c) RNA analogs thereof wherein U is substituted for T throughout.

17. A substantially inclusive nucleic acid probe set for the detection of a member of the genus Shigella, which further detects enteroinvasive *Escherichia coli*, comprising at least two capture/detector probe pairs, each probe having a nucleotide sequence consisting of a specific sequence element, optionally incorporated into a larger non-Shigella sequence for assay purposes, wherein:
   a) each of a first pair of probes has a specific sequence element which is independently selected from the group consisting of:
      i) a fragment of a selected strand of Shigella DNA consisting of *Shigelia sonnei* fragments NT14 (SEQ ID NO: 4) and NT15 (SEQ ID NO: 3), which specifically hybridizes to nucleic acid from Shigella and/or enteroinvasive *E. coli*, and
      ii) an RNA analog thereof wherein U is substituted for T throughout, and
   b) each of a second pair of probes has a specific sequence element which is independently selected from the group consisting of:
      i) a fragment of a selected strand of a double-stranded nucleic acid having the sequence SEQ ID NO: 12, which specifically hybridizes to nucleic acid from Shigella, and,
      ii) an RNA analog thereof wherein U is substituted for T throughout.

18. A substantially inclusive probe set of claim 17, comprising at least two capture/detector probe pairs, wherein the specific sequence elements of the first pair are fragments of a selected strand of Shigella DNA consisting of *Shigella sonnei* fragments NT14 (SEQ ID NO: 4) and NT15 (SEQ ID NO: 3), which specifically hybridize to nucleic acid from Shigella and/or enteroinvasive *E. coli*, or an RNA analog thereof wherein U is substituted for T throughout, and the specific sequence elements of the second pair are fragments of a selected strand of a double-stranded nucleic acid having the sequence SEQ ID NO: 12, which specifically hybridize to nucleic acid from Shigella, or an RNA analog thereof wherein U is substituted for T throughout.

19. A substantially inclusive probe set of claim 18, the probe set also being exclusive of exclusivity organisms commonly found in stool and substantially exclusive of non-enteroinvasive *Escherichia coli* Enterobacteriaceae.

20. A substantially inclusive probe set of claim 19 wherein the specific sequence elements of the first pair of probes are 1864 (SEQ ID NO: 22) and a sequence which is wholly complementary to the sequence of probe 437, and the specific sequence elements of the second pair of probes are 1706 (SEQ ID NO: 27) and 1707 (SEQ ID NO: 28).

21. A substantially inclusive nucleic acid probe set for the detection of a member of the genus Shigella, which further detects enteroinvasive *Escherichia coli*, comprising at least two capture/detector probe pairs, each probe having a nucleotide sequence consisting of a specific sequence element, optionally incorporated into a larger non-Shigelia sequence for assay purposes, wherein:

each of a first pair of probes has a specific sequence element which is independently selected from the group consisting of:
   a) 1864 (SEQ ID NO: 22);
   b) an oligonucleotide having a sequence wholly complementary to probe 437; and
   c) RNA analogs of a) or b) wherein U is substituted for T throughout, and each of a second pair of probes has a specific sequence element which is independently selected from the group consisting of:
   a) 1706 (SEQ ID NO: 27);
   b) 1707 (SEQ ID NO: 28); and
   c) RNA analogs of a) or b) wherein U is substituted for T throughout.

22. A nucleic acid probe wherein the nucleotide sequence of the probe consists of a specific sequence element, optionally incorporated into a larger non-Shigella sequence for assay purposes, said specific sequence element being a fragment of Shigella specific fragment NT-6 (nucleotides 1–124 of SEQ ID NO: 1), a fragment which is complementary over its length to a selected strand of NT6, or an RNA analog thereof wherein is substituted for T throughout, wherein the probe substantially retains the inclusivity behavior of NT-6.

23. A nucleic acid probe of claim 22, which has improved exclusivity behavior for non-enteroinvasive *Escherichia coli* Enterobacteriaceae as compared with NT-6 and is exclusive of the exclusivity organisms commonly found in stool.

24. A nucleic acid probe of claim 23 wherein the specific sequence element is selected from the group consisting of:
   a) 1911 (SEQ ID NO: 16), 5'-CCGATCTTCTATT-GTACGACGGTGTTCGTCAAAAGCTAAT-3';
   b) 1500 (SEQ ID NO: 14), 5'-TTGCAGCGCCTC-TACTACCGGATACAGCCTCCATT-3';
   c) 1501 (SEQ ID NO: 15), 5'-CCTCCTTCAGGGC-GGATTCCAGCCGTTCACATTGT-3';
   d) an RNA sequence having the sequence of any one of a) through c), wherein U is substituted for T; and
   e) exact complements of any one of a) through d).

25. A nucleic acid probe wherein the nucleotide sequence of the probe consists of a specific sequence element, optionally incorporated into a larger non-Shigella sequence for assay purposes, said specific sequence element being a fragment of Shigella specific fragment NT11-2 (SEQ ID NO: 2), a fragment which is complementary over its length to a selected strand of NT11-2, or an RNA analog thereof wherein U is substituted for T throughout, wherein the probe substantially retains the inclusivity behavior of NT11-2.

26. A nucleic acid probe of claim 25 which substantially retains the exclusivity behavior of NT11-2 (SEQ ID NO: 2) towards non-enteroinvasive *Escherichia coli* Enterobacteriaceae.

27. A nucleic acid probe of claim 26 wherein the specific sequence element is selected from the group consisting of:
   a) 1682 (SEQ ID NO: 17), 5-CTGGTGAAC-AACGTCTTACAAAGATGGTTCCTGGATGGATT-3';
   b) complement of 1682 (SEQ ID NO: 29), 5 - A A T C C A T C C A - GGAACCATCTTTGTAAGACGTTGTTCACCAG-3'; and
   c) an RNA sequence having the sequence of (a) or (b), wherein U is substituted for T.

28. A nucleic acid probe wherein the nucleotide sequence of the probe consists of a specific sequence element, optionally incorporated into a larger non-Shigelia sequence for assay purposes, said specific sequence element being a fragment of Shigella specific fragment NT11-2 (SEQ ID NO: 2), a fragment which is complementary over its length to a selected strand of NT11-2, or an RNA analog thereof wherein U is substituted for T throughout, and wherein the probe moderately retains the inclusivity behavior of NT11-2.

29. A nucleic acid probe of claim 28 which substantially retains the exclusivity behavior of NT11-2 (SEQ ID NO: 2) towards non-enteroinvasive *Escherichia coli* Enterobacteriaceae.

30. A nucleic acid probe of claim 29 wherein the specific sequence element is selected from the group consisting of:
   a) 1683 (SEQ ID NO: 18), 5'-AGTCTTTCCGT-GTTTCTCAGAAATGGGGGCAACGTGCAAAA-3';
   b) complement of 1683 (SEQ ID NO: 30), 5 ' - T T T T G C A C G T T - GCCCCCATTTCTGAGAAACACGGAAAGACT-3'; and
   c) an RNA sequence having the sequence of a) or b), wherein U is substituted for T.

31. A nucleic acid probe wherein the nucleotide sequence of the probe consists of a specific sequence element, optionally incorporated into a larger non-Shigella sequence for assay purposes, said specific sequence element being a fragment of Shigella specific fragment NT11-2 (SEQ ID NO: 2), a fragment which is complementary over its length to a selected strand of NT11-2, or an RNA analog thereof wherein U is substituted for T throughout, and wherein the probe partially retains the inclusivity behavior of NT11-2.

32. A nucleic acid probe of claim 31 which substantially retains the exclusivity behavior of NT11-2 (SEQ ID NO: 2) towards non-enteroinvasive *Escherichia coli* Enterobacteriaceae.

33. A nucleic acid probe of claim 32 wherein the specific sequence element is selected from the group consisting of:
   a) 1708 (SEQ ID NO: 19), 5'-CCACCGTTGAAG-CGTAAACCGTTTGACCGATGGAT-3';
   b) 1709 (SEQ ID NO: 20), 5'-GCTGGGGTCTACA-GGTGCAATAACCACTTAGACGGT'-3';
   c) an RNA sequence having the sequence of a) or b), wherein U is substituted for T; and
   d) exact complements of any one of a) through c).

34. A nucleic acid probe wherein the nucleotide sequence of the probe consists of a specific sequence element, optionally incorporated into a larger non-Shigella sequence for assay purposes, said specific sequence element being a fragment of Shigella specific fragment NT18-1a (SEQ ID NO: 10), a fragment which is complementary over its length to a selected strand of NT18-1a, or an RNA analog thereof wherein U is substituted for T throughout, wherein the probe substantially retains the inclusivity behavior of NT18-1a.

35. A nucleic acid probe of claim 34 which substantially retains the exclusivity behavior of NT18-1a (SEQ ID NO: 10) towards non-enteroinvasive *Escherichia coli* Enterobacteriaceae.

36. A nucleic acid probe of claim 33 wherein the specific sequence element is selected from the group consisting of:
   a) 1712 (SEQ ID NO: 23), 5'-CCTGTGGCTCTC-GGTTCTGATGGTATAGCAACTAAAT-3';
   b) 1713 (SEQ ID NO: 24) 5'-CAAGGATGTTTC-GGAATTGAGTGGGGAGTTGCGAAAT-3';
   c) an RNA sequence having the sequence of a) or b), wherein U is substituted for T; and
   d) exact complements of any one of a) through c).

37. A nucleic acid probe wherein the nucleotide sequence of the probe consists of a specific sequence element, optionally incorporated into a larger non-Shigella sequence for assay purposes, said specific sequence element being a fragment of Shigella specific fragment NT19-2 (SEQ ID NO: 11), a fragment which is complementary over its length to a selected strand of NT19-2, or an RNA analog thereof wherein U is substituted for T throughout, wherein the probe substantially retains the inclusivity behavior of NT19-2.

38. A nucleic acid probe of claim 37 which substantially retains the exclusivity behavior of NT19-2 (SEQ ID NO: 11) towards non-enteroinvasive *Escherichia coli* Enterobacteriaceae.

39. A nucleic acid probe of claim 38 wherein the specific sequence element is selected from the group consisting of:
   a) 1684 (SEQ ID NO: 25), 5'-CAGGCAATCGAAG-CATATCGCGGTTCTCCACAACT-3';
   b) 1685 (SEQ ID NO: 26), 5'-TGAATGCGCTG-ACCGAAAACGAGCGCTGGGTATCT-3';
   c) an RNA sequence having the sequence of a) or b), wherein U is substituted for T; and
   d) exact complements of any one of a) through c).

40. A substantially inclusive nucleic acid probe for the detection of a member of the genus Shigella, wherein the nucleotide sequence of said probe consists of a specific sequence element, optionally incorporated into a larger non-Shigella sequence for assay purposes, said specific sequence element being a fragment of Shigella DNA consisting of NT14 (SEQ ID NO: 4) and NT15 (SEQ ID NO: 3), a fragment which is complementary over its length to a selected strand of NT14 and NT15, or an RNA analog thereof wherein U is substituted for T throughout.

41. A nucleic acid probe of claim 40 wherein said probe is moderately exclusive of non-enteroinvasive *Escherichia coli* exclusivity organisms.

42. A nucleic acid probe of claim 41 wherein said probe is substantially exclusive of non-enteroinvasive *Escherichia coli* exclusivity organisms and is exclusive of the exclusivity organisms commonly found in stool.

43. An isolated, exclusively chromosomal, Shigella specific nucleic acid fragment identified by the steps of:
   a) providing fragmented DNA isolated from *Shigella flexneri* as target DNA;
   b) providing a competitor mix containing nucleic acid isolated from at least one species of enterovirulent *Escherichia coli* with the proviso that said enterovirulent species is not selected from the group of enteroinvasive *Escherichia coli*;
   c) conducting subtractive hybridization between said target DNA and said competitor mix;
   d) isolating the portion of target DNA remaining unhybridized in step c) to obtain a fraction enriched for Shigella specific sequences;
   e) hybridizing a portion of said fraction to nucleic acid present in said competitor mix;
   f) repeating steps c) through e) substituting said fraction as target DNA in step c), proceeding to step g) when hybridization to competitor nucleic acid in step e) is substantially reduced;
   g) using said fraction to obtain one or more clones from a *Shigella flexneri* DNA library;
   h) identifying a Shigella specific fragment present in a clone of step g) or subclone thereof by screening for:
      (i) hybridization to nucleic acid isolated from one or more organisms selected from the group consisting of *Shigella dysenteriae*, *Shigella flexneri*, *Shigella boydii*, and *Shigella sonnei*, and optionally, enteroinvasive *Escherichia coli*; and
      (ii) exclusivity towards a panel of exclusivity organisms,
   whereby a Shigella specific fragment which is substantially exclusive of non-enteroinvasive *Escherichia coli* Enterobacteriaceae is obtained.

44. An isolated chromosomal Shigella specific nucleic acid fragment identified by the steps of:
   a) providing fragmented DNA isolated from *Shigella sonnei* as target DNA;
   b) providing a competitor mix containing nucleic acid isolated from at least one species of enterovirulent *Escherichia coli* with the proviso that said enterovirulent species is not selected from the group of enteroinvasive *Escherichia coli*;
   c) conducting subtractive hybridization between said target DNA and said competitor mix;
   d) isolating the portion of target DNA remaining unhybridized in step c) to obtain a fraction enriched for Shigella specific sequences;
   e) hybridizing a portion of said fraction to nucleic acid present in said competitor mix;
   f) repeating steps c) through e) substituting said fraction as target DNA in step c), proceeding to step g) when hybridization to competitor nucleic acid in step e) is substantially reduced;
   g) using said fraction to obtain one or more clones from a *Shigella sonnei* DNA library;
   h) identifying a Shigella specific fragment present in a clone of step g) or subclone thereof by screening for:
      (i) hybridization to nucleic acid isolated from one or more organisms selected from the group consisting of *Shigelia dysenteriae*, *Shigella flexneri*, *Shigelia boydii*, and *Shigella sonnei*, and optionally, enteroinvasive *Escherichia coli*; and
      (ii) exclusivity towards a panel of exclusivity organisms,
   whereby a Shigella specific fragment which is substantially exclusive of non-enteroinvasive *Escherichia coli* Enterobacteriaceae is obtained.

45. A nucleic acid probe for the detection of a member of the genus Shigella, wherein the nucleotide sequence of said probe consists of a specific sequence element, optionally incorporated into a larger non-Shigella sequence for assay purposes, wherein said specific sequence element is selected from the group consisting of:

a) 1707 (SEQ ID NO: 28), 5'-CTCAGATTCACCT-GTCACATTGTTGTGAGCTTTGG-3';

b) 1706 (SEQ ID NO: 27), 5'-GTGATGGCCCATTC-AACACCACCTGCGAATACCGG-3';

c) an RNA sequence having the sequence of a) or b), wherein U is substituted for T; and d) exact complements of any one of a) through c).

46. A nucleic acid probe for the detection of a member of the genus Shigella, wherein the nucleotide sequence of said probe consists of a specific sequence element, optionally incorporated into a larger non-Shigella sequence for assay purposes, wherein said specific sequence element is selected from the group consisting of:

a) 437 (SEQ ID NO: 21), 5'-CGATGATGCCATTCTCTGCCA-GCTCCGTCTGGGAGCCGCCGGGTTTCC-3';

b) 1864 (SEQ ID NO: 22), 5'-GGAGCAGTCTGGTCTGA-3';

c) an RNA sequence having the sequence of any one of a) or b), wherein U is substituted for T; and d) exact complements of a) through c).

47. A substantially inclusive nucleic acid capture/detector probe pair for the detection of a member of the genus Shigella, comprising a substantially inclusive tailed capture probe and a detector probe wherein:

the nucleotide sequence of the tailed capture probe consists of a first specific sequence element and a polynucleotide tail, wherein the first specific sequence element is selected from the group consisting of:

a) 1864 (SEQ ID NO: 22);

b) an RNA molecule having the sequence of a), wherein U is substituted for T; and c) exact complements of a) or b);

and wherein the first specific sequence element is complementary to a selected strand of Shigella DNA consisting of NT14 (SEQ ID NO: 4) and NT15 (SEQ ID NO: 3), and the nucleotide sequence of the detector probe consists of a second specific sequence element, optionally incorporated into a larger non-Shigella sequence for assay purposes, wherein said second specific sequence element is a fragment of a strand which is complementary to the selected strand.

48. A substantially inclusive capture/detector probe pair of claim 47, the probe pair also being exclusive of exclusivity organisms commonly found in stool and substantially exclusive of non-enteroinvasive *Escherichia coli* Enterobacteriaceae.

49. A capture/detector probe pair of claim 47 wherein the first specific sequence element is 1864 (SEQ ID NO: 22) and the second specific sequence element has a sequence which is complementary over its length to the sequence of probe 437.

50. A capture/detector probe pair of claim 47 wherein the first specific sequence element has a sequence which is complementary over its length to the sequence of probe 1864 and the second specific sequence element is probe 437 (SEQ ID NO: 21).

* * * * *